United States Patent [19]
Menke et al.

[11] Patent Number: 6,150,303
[45] Date of Patent: Nov. 21, 2000

[54] SUBSTITUTED 3-PHENYLISOXAZOLINES

[75] Inventors: Olaf Menke, Altleiningen; Markus Menges, Bensheim; Gerhard Hamprecht, Weinheim; Robert Reinhard, Ludwigshafen; Peter Schäfer, Ottersheim; Cyrill Zagar, Ludwigshafen; Karl-Otto Westphalen, Speyer; Ulf Misslitz, Neustadt; Helmut Walter, Obrigheim, all of Germany

[73] Assignee: BASF Aktiengesellschaft, Ludwigschafen, Germany

[21] Appl. No.: 09/463,246

[22] PCT Filed: Jul. 20, 1998

[86] PCT No.: PCT/EP98/04489

§ 371 Date: Jan. 21, 2000

§ 102(e) Date: Jan. 21, 2000

[87] PCT Pub. No.: WO99/05130

PCT Pub. Date: Feb. 4, 1999

[30] Foreign Application Priority Data

Jul. 23, 1997 [DE] Germany ............... 197 31 513

[51] Int. Cl.[7] .................. A01N 43/72; C07D 261/04
[52] U.S. Cl. .................. 504/271; 548/243; 548/245
[58] Field of Search .................. 548/243, 245; 504/271

[56] References Cited

U.S. PATENT DOCUMENTS

| | | | |
|---|---|---|---|
| 4,983,210 | 1/1991 | Rheinheimer et al. | 504/248 |
| 5,262,388 | 11/1993 | Munor et al. | 504/271 |
| 5,401,763 | 3/1995 | Camaggi et al. | 514/378 |
| 5,521,143 | 5/1996 | Loeher et al. | 504/106 |

FOREIGN PATENT DOCUMENTS

| | | |
|---|---|---|
| 334120 | 9/1989 | European Pat. Off. |
| 514987 | 11/1992 | European Pat. Off. |
| 611760 | 8/1994 | European Pat. Off. |
| 6236057 | 8/1994 | Japan. |
| 741459 | 2/1995 | Japan. |
| 92/03053 | 3/1992 | WIPO. |
| 95/24398 | 9/1995 | WIPO. |

OTHER PUBLICATIONS

*Chem. Abst.*, 95(21), Nov. 23, 1981, AN 187128z.
*Chem. Abst.*, 109(17), Oct. 24, 1988, AN 149512v.
Hamper et al., *J. Agric. Food Chem.*, 43, 223, 1995.
Carr et al., *J. Med. Chem.*, 20, 935, 1977.
Martins et al., *J. Heterocyclic Chem.*, 33, 1619, 1996.

*Primary Examiner*—Fiona T. Powers
*Attorney, Agent, or Firm*—Keil & Weinkauf

[57] ABSTRACT

Substituted 3-phenylisoxazolines I, and their salts and enol ethers, are described as herbicides where $X = -O-, -S-, -N(R^9)-$;

$R^1 = CN$, $C_1-C_4$-alkyl, $C_1-C_4$-haloalkyl, $C_1-C_4$-haloalkoxy, $C_1-C_4$-alkylsulfonyl;

$R^2 = H$ or unsubstituted or substituted $C_1-C_6$-alkyl, $(C_1-C_6$-alkyl)carbonyl, $C_1-C_6$-alkylsulfonyl, $C_2-C_6$-alkenyl, $(C_2-C_6$-alkenyl)carbonyl, $C_2-C_6$-alkynyl, $(C_2-C_6$-alkynyl)carbonyl;

$R^3 = H$, halogen;

$R^4 = CN$, halogen, $C_1-C_3$-haloalkyl;

$R^5 = H$, CN, halogen, $C_1-C_3$-haloalkyl;

$R^6 = H$, CN, halogen, $C_1-C_3$-haloalkyl or unsubstituted or substituted $C_1-C_6$-alkoxy;

$R^7 = CN$, halogen;

$R^8$ in position $\alpha$, $R^7$ in this case being in position $\beta$, or in position $\beta$, $R^7$ in this case being in position $\alpha$, is 1) H, OH, SH, CN, $NO_2$, halogen, $C_1-C_6$-alkyl, $C_1-C_6$-haloalkyl, $C_1-C_6$-haloalkoxy, $C_1-C_6$-haloalkylthio, $C_1-C_6$-alkylthio-($C_1-C_6$-alkyl)carbonyl, ($C_1-C_6$-alkyl)iminooxycarbonyl, $C_1-C_6$-alkoxy-$C_1-C_6$-alkyl, $C_1-C_6$-alkoxyamino-$C_1-C_6$-alkyl, $C_1-C_6$-alkoxy-$C_1-C_6$-alkylamino-$C_1-C_6$-alkyl, 2) unsubstituted or substituted $C_1-C_6$-alkoxy, $C_1-C_6$-alkylthio, $C_3-C_6$-cycloalkoxy, $C_3-C_6$-cycloalkylthio, $C_2-C_6$-alkenyloxy, $C_2-C_6$-alkenylthio, $C_2-C_6$-alkynyloxy, $C_2-C_6$-alkynylthio, ($C_1-C_6$-alkyl)carbonyloxy, ($C_1-C_6$-alkyl)carbonylthio, ($C_1-C_6$-alkoxy)carboxyloxy, ($C_2-C_6$-alkenyl)carbonyloxy, ($C_2-C_6$-alkenyl)carbonylthio, ($C_2-C_6$-alkynyl)carbonyloxy, ($C_2-C_6$-alkynyl)carbonylthio, $C_1-C_6$-alkylsulfonyloxy or $C_1-C_6$-alkylsulfonyl, 3) 29 further radicals;

$R^9 = H$, $C_1-C_6$-alkyl, $C_3-C_6$-cycloalkyl, $C_3-C_6$-alkenyl, $C_3-C_6$-alkynyl, $C_1-C_6$-alkoxy-$C_1-C_6$-alkyl, ($C_1-C_6$-alkoxy)carbonyl-$C_1-C_6$-alkyl, ($C_3-C_6$-alkenyloxy)carbonyl-$C_1-C_6$-alkyl, unsubstituted or substituted phenyl or phenyl-$C_1-C_6$-alkyl.

5 Claims, No Drawings

SUBSTITUTED 3-PHENYLISOXAZOLINES

This application is a 371 of PCT/EP98/04489 filed Jul. 20, 1998.

The present invention relates to substituted 3-phenylisoxazolines of the formula I

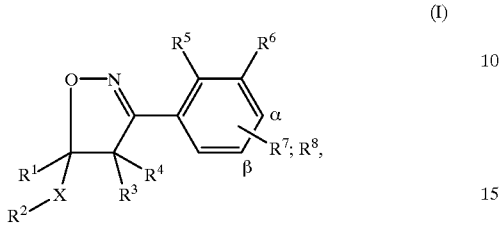

where:

X is oxygen, sulfur or —N($R^9$)—;

$R^1$ is cyano, $C_1$–$C_4$-alkyl, $C_1$–$C_4$-haloalkyl, $C_1$–$C_4$-haloalkoxy or $C_1$–$C_4$-alkylsulfonyl;

$R^2$ is hydrogen, $C_1$–$C_6$-alkyl, ($C_1$–$C_6$-alkyl)carbonyl, $C_1$–$C_6$-alkylsulfonyl, $C_2$–$C_6$-alkenyl, ($C_2$–$C_6$-alkenyl)carbonyl, $C_2$–$C_6$-alkynyl or ($C_2$–$C_6$-alkynyl)carbonyl, where the 7 last-mentioned radicals may, if desired, carry 1 to 3 radicals, in each case selected from the group consisting of halogen, $C_1$–$C_6$-alkoxy, $C_1$–$C_6$-alkylamino, di($C_1$–$C_6$-alkyl)amino, $C_1$–$C_6$-alkoxyimino, phenyl, CO—$OR^{10}$ or CO—N($R^{11}$)—$R^{12}$;

$R^3$ is hydrogen or halogen;

$R^4$ is cyano, halogen or $C_1$–$C_3$-haloalkyl;

$R^5$ is hydrogen, cyano, halogen or $C_1$–$C_3$-haloalkyl;

$R^6$ is hydrogen, cyano, halogen, $C_1$–$C_3$-haloalkyl or $C_1$–$C_6$-alkoxy which may, if desired, carry one or two substituents, in each case selected from the group consisting of $C_1$–$C_6$-alkoxyimino, CO—$OR^{13}$ and CO—N($R^{14}$)—$R^{15}$;

$R^7$ in position α or β is cyano or halogen;

$R^8$ in position α, $R^7$ in this case being in position β, or in position β, $R^7$ in this case being in position α, is
1) hydrogen, hydroxyl, mercapto, cyano, nitro, halogen, $C_1$–$C_6$-alkyl, $C_1$–$C_6$-haloalkyl, $C_1$–$C_6$-haloalkoxy, $C_1$–$C_6$-haloalkylthio, $C_1$–$C_6$-alkylthio-($C_1$–$C_6$-alkyl)carbonyl, ($C_1$–$C_6$-alkyl)iminooxycarbonyl, $C_1$–$C_6$-alkoxy-$C_1$–$C_6$-alkyl, $C_1$–$C_6$-alkoxyamino-$C_1$–$C_6$-alkyl, $C_1$–$C_6$-alkoxy-$C_1$–$C_6$-alkylamino-$C_1$–$C_6$-alkyl,
2) $C_1$–$C_6$-alkoxy, $C_1$–$C_6$-alkylthio, $C_3$–$C_6$-cycloalkoxy, $C_3$–$C_6$-cycloalkylthio, $C_2$–$C_6$-alkenyloxy, $C_2$–$C_6$-alkenylthio, $C_2$–$C_6$-alkynyloxy, $C_2$–$C_6$-alkynylthio, ($C_1$–$C_6$-alkyl)carbonyloxy, ($C_1$–$C_6$-alkyl)carbonylthio, ($C_1$–$C_6$-alkoxy) carboxyloxy, ($C_2$–$C_6$-alkenyl)carbonyloxy, ($C_2$–$C_6$-alkenyl)carbonylthio, ($C_2$–$C_6$-alkynyl)carbonyloxy, ($C_2$–$C_6$-alkynyl)carbonylthio, $C_1$–$C_6$-alkylsulfonyloxy or $C_1$–$C_6$-alkylsulfonyl, where each of the 17 last-mentioned radicals may, if desired, carry one to three substituents,
3) —CO—$R^{22}$, —CS—$R^{22}$, —C(N$R^{23}$)—$R^{22}$, —C($R^{22}$)($Z^1R^{24}$)($Z^2R^{25}$) where $Z^1$ and $Z^2$ are each oxygen or sulfur, —C($R^{22}$)=C($R^{26}$)—CN, —C($R^{22}$)=C($R^{26}$)—CO—$R^{27}$, —CH($R^{22}$)—CH($R^{26}$)—CO—$R^{27}$, —C($R^{22}$)=C($R^{26}$)—CH$_2$—CO—$R^{27}$, —C($R^{22}$)=C($R^{26}$)—C($R^{28}$)=C($R^{29}$)—CO—$R^{27}$, —C($R^{22}$)=C($R^{26}$)—CH$_2$—CH($R^{30}$)—CO—$R^{27}$, —CO—$OR^{31}$, —CO—$SR^{31}$, —CO—N($R^{31}$)—$OR^{18}$, —C≡C—CO—NH—$OR^{18}$, —C≡C—CO—N($R^{31}$)—$OR^{18}$, —C≡C—CS—NH—$OR^{18}$, —C≡C—CS—N($R^{31}$)—$OR^{18}$, —C($R^{22}$)=C($R^{26}$)—CO—NH—$OR^{18}$, —C($R^{22}$)=C($R^{26}$)—CO—N($R^{31}$)—$OR^{18}$, —C($R^{22}$)=C($R^{26}$)—CS—NH—$OR^{18}$, —C($R^{22}$)=C($R^{26}$)—CS—N($R^{31}$)—$OR^{18}$, —C($R^{22}$)=C($R^{26}$)—C($R^{21}$)=N—$OR^{18}$, —C($R^{21}$)=N—$OR^{18}$, —C≡C—C($R^{21}$)=N—$OR^{18}$, —C($Z^1R^{24}$)($Z^2R^{25}$)—$OR^{31}$, —C($Z^1R^{24}$)($Z^2R^{25}$)—$SR^{31}$, —C($Z^1R^{24}$)($Z^2R^{25}$)—N($R^{32}$)$R^{33}$, —N($R^{32}$)$R^{33}$ or —CON($R^{32}$)$R^{33}$;

$R^9$, $R^{10}$, $R^{12}$, $R^{13}$ and $R^{15}$ independently of one another are each hydrogen, $C_1$–$C_6$-alkyl, $C_3$–$C_6$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, ($C_3$–$C_6$-alkenyloxy)carbonyl-$C_1$–$C_6$-alkyl, phenyl or phenyl-$C_1$–$C_6$-alkyl, where the phenyl group and the phenyl ring of the phenylalkyl group may be unsubstituted or may carry one to three radicals, in each case selected from the group consisting of halogen, nitro, cyano, $C_1$–$C_6$-alkyl, $C_1$–$C_6$-haloalkyl, $C_1$–$C_6$-alkoxy and ($C_1$–$C_6$-alkyl)carbonyl;

$R^{11}$ and $R^{14}$ independently of one another are each hydrogen, hydroxyl, $C_1$–$C_6$-alkyl, $C_3$–$C_6$-cycloalkyl, $C_1$–$C_6$-alkoxy, ($C_1$–$C_6$-alkoxy)carbonyl-$C_1$–$C_6$-alkoxy, $C_3$–$C_6$-alkenyl or $C_3$–$C_6$-alkenyloxy;

$R^{22}$ is hydrogen, cyano, $C_1$–$C_6$-alkyl, $C_1$–$C_6$-haloalkyl, $C_2$–$C_6$-alkenyl, $C_2$–$C_6$-alkynyl, $C_3$–$C_6$-cycloalkyl, $C_1$–$C_6$-alkoxy-$C_1$–$C_6$-alkyl or ($C_1$–$C_6$-alkoxy)carbonyl;

$R^{23}$ is hydrogen, hydroxyl, $C_1$–$C_6$-alkyl, $C_3$–$C_6$-alkenyl, $C_3$–$C_6$-alkynyl, $C_3$–$C_7$-cycloalkyl, $C_1$–$C_6$-haloalkyl, $C_1$–$C_6$-alkoxy-$C_1$–$C_6$-alkyl, $C_1$–$C_6$-alkoxy, $C_3$–$C_6$-alkenyloxy, $C_3$–$C_6$-alkynyloxy, $C_3$–$C_6$-cycloalkoxy, $C_5$–$C_7$-cycloalkenyloxy, $C_1$–$C_6$-haloalkoxy, $C_3$–$C_6$-haloalkenyloxy, hydroxy-$C_1$–$C_6$-alkoxy, cyano-$C_1$–$C_6$-alkoxy, $C_3$–$C_6$-cycloalkyl-$C_1$–$C_6$-alkoxy, $C_1$–$C_6$-alkoxy-$C_1$–$C_6$-alkoxy, $C_1$–$C_6$-alkoxy-$C_3$–$C_6$-alkenyloxy, ($C_1$–$C_6$-alkyl)carbonyloxy, ($C_1$–$C_6$-haloalkyl)carbonyloxy, ($C_1$–$C_6$-alkyl)carbamoyloxy, ($C_1$–$C_6$-haloalkyl)carbamoyloxy, ($C_1$–$C_6$-alkyl) carbonyl-$C_1$–$C_6$-alkyl, ($C_1$–$C_6$-alkyl)carbonyl-$C_1$–$C_6$-alkoxy, $C_1$–$C_6$-alkoxy)carbonyl-$C_1$–$C_6$-alkyl, ($C_1$–$C_6$-alkoxy)carbonyl-$C_1$–$C_6$-alkoxy, $C_1$–$C_6$-alkylthio-$C_1$–$C_6$-alkoxy, di($C_1$–$C_6$-alkyl) amino-$C_1$–$C_6$-alkoxy, phenyl which may itself carry one to three substituents, phenyl-$C_1$–$C_6$-alkoxy, phenyl-$C_3$–$C_6$-alkenyloxy or phenyl-$C_3$–$C_6$-alkynyloxy, where in each case one or two methylene groups of the hydrocarbon chains may be replaced by —O—, —S— or —N($C_1$–$C_6$-alkyl)-, and where each phenyl ring may be unsubstituted or may carry one to three substituents, heterocyclyl, heterocyclyl-$C_1$–$C_6$-alkoxy, heterocyclyl-$C_3$–$C_6$-alkenyloxy or heterocyclyl-$C_3$–$C_6$-alkynyloxy, where in each case one or two methylene groups of the hydrocarbon chains may be replaced by —O—, —S— or —N($C_1$–$C_6$-alkyl)-, and where each heterocycle is unsubstituted or itself carries one to three substituents, or amino which may, if desired, be substituted, or an azaheterocycle;

$R^{24}$ and $R^{25}$ independently of one another are each $C_1$–$C_6$-alkyl, $C_1$–$C_6$-haloalkyl, $C_3$–$C_6$-alkenyl, $C_3$–$C_6$-alkynyl, $C_1$–$C_6$-alkoxy-$C_1$–$C_6$-alkyl or $R^{24}$ and $R^{25}$ together form a saturated or unsaturated 2- to 4-membered hydrocarbon chain which may carry an oxo substituent, where one member of this chain may be replaced by an oxygen, sulfur or nitrogen atom which is not adjacent to the variables $Z^1$ and $Z^2$, and where the hydrocarbon chain may carry one to three radicals, and where the hydrocarbon chain may also be substituted by a fused-on or spiro-linked 3- to 7-membered ring which may contain as ring members one or two hetero atoms selected from the group consisting of oxygen, sulfur, nitrogen and $C_1$–$C_6$-alkyl-substituted nitrogen, and which may, if desired, itself carry one or two substituents;

$R^{26}$ is hydrogen, cyano, halogen, $C_1$–$C_6$-alkyl, $C_1$–$C_6$-haloalkyl, $C_1$–$C_6$-alkoxy, ($C_1$–$C_6$-alkyl)carbonyl or ($C_1$–$C_6$-alkoxy)carbonyl;

$R^{27}$ is hydrogen, O—$R^{34}$, S—$R^{34}$, $C_1$–$C_6$-alkyl which may carry one or two $C_1$–$C_6$-alkoxy substituents, $C_2$–$C_6$-alkenyl, $C_2$–$C_6$-alkynyl, $C_1$–$C_6$-haloalkyl, $C_3$–$C_6$-cycloalkyl, $C_1$–$C_6$-alkylthio-$C_1$–$C_6$-alkyl, $C_1$–$C_6$-alkyliminooxy, —N($R^{32}$)$R^{33}$ or phenyl which may be unsubstituted or may carry one to three substituents, in each case selected from the group consisting of cyano, nitro, halogen, $C_1$–$C_6$-alkyl, $C_2$–$C_6$-alkenyl, $C_1$–$C_6$-haloalkyl, $C_1$–$C_6$-alkoxy and ($C_1$–$C_6$-alkoxy)carbonyl;

$R^{28}$ is hydrogen, cyano, halogen, $C_1$–$C_6$-alkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkyl)carbonyl, ($C_1$–$C_6$-alkoxy)carbonyl, —N($R^{32}$)$R^{33}$, or phenyl which may itself carry one to three substituents, in each case selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl;

$R^{29}$ is hydrogen, cyano, halogen, $C_1$–$C_6$-alkyl, $C_1$–$C_6$-alkoxy, $C_1$–$C_6$-haloalkyl, ($C_1$–$C_6$-alkyl)carbonyl or ($C_1$–$C_6$-alkoxy)carbonyl;

$R^{30}$ is hydrogen, cyano, $C_1$–$C_6$-alkyl or ($C_1$–$C_6$-alkoxy) carbonyl;

$R^{31}$ and $R^{34}$ independently of one another are each hydrogen, $C_1$–$C_6$-alkyl, $C_1$–$C_6$-haloalkyl, $C_2$–$C_6$-alkenyl or $C_2$–$C_6$-alkynyl, where the 4 last-mentioned groups may in each case carry one or two radicals, or ($C_1$–$C_6$-alkyl)carbonyl, ($C_1$–$C_6$-haloalkyl)carbonyl, ($C_1$–$C_6$-alkoxy)carbonyl, $C_1$–$C_6$-alkylaminocarbonyl, di($C_1$–$C_6$-alkyl)aminocarbonyl, $C_1$–$C_6$-alkyloximino-$C_1$–$C_6$-alkyl, $C_3$–$C_6$-cycloalkyl, phenyl or phenyl-$C_1$–$C_6$-alkyl, where the phenyl rings may be unsubstituted or may carry one to three substituents;

$R^{32}$ and $R^{33}$ independently of one another are each hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, $C_1$–$C_6$-alkoxy-$C_1$–$C_6$-alkyl, ($C_1$–$C_6$-alkyl)carbonyl, ($C_1$–$C_6$-alkoxy)carbonyl, ($C_1$–$C_6$-alkoxy)carbonyl-$C_1$–$C_6$-alkyl, ($C_1$–$C_6$-alkoxy)carbonyl-$C_2$–$C_6$-alkenyl, where the alkenyl chain may additionally carry one to three halogen and/or cyano radicals, or $C_1$–$C_6$-alkylsulfonyl, ($C_1$–$C_6$-alkoxy)carbonyl-$C_1$–$C_6$-alkylsulfonyl, phenyl or phenylsulfonyl, where the two phenyl rings may be unsubstituted or may themselves carry one to three substituents, in each case selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl, or $R^{32}$ and $R^{33}$ together with the linking nitrogen atom form a saturated or unsaturated 4- to 7-membered azaheterocycle which, in addition to carbon ring members, may, if desired, contain one of the following members: —O—, —S—, —N=, —NH— or —N($C_1$–$C_6$-alkyl)—;

and the agriculturally useful salts and enol ethers of the compounds I.

Furthermore, the invention relates to the use of the compounds I as herbicides, herbicidal compositions which comprise the compounds I as active ingredients, processes for preparing herbicidal compositions using the compounds I, and methods for controlling unwanted vegetation using the compounds I.

3-Phenylisoxazolines whose general formula formally also includes some of the present compounds I are already described as pharmaceutically active compounds in WO 95/24398.

Furthermore, JP-A 07/041459 inter alia relates to certain 3-phenylisoxazolines which differ from the present compound I in particular in position 4 and which are also said to have pharmaceutical activity.

It is an object of the present invention to provide novel herbicidally active compounds which allow better selective control of unwanted plants than previous compounds.

We have found that these objects are achieved by the substituted 3-phenylisoxazolines of the formula I defined at the outset. Furthermore, we have found herbicidal compositions which comprise the compounds I and which have very good herbicidal activity. Moreover, we have found processes for preparing these compositions and methods for controlling unwanted vegetation using the compounds I.

Depending on the substitution pattern, the compounds of the formula I can contain one or more chiral centers, in which case they can exist in the form of enantiomer and diastereomer mixtures. In the case of compounds I having at least one olefinic radical, E-/Z-isomers are, if appropriate, also possible. This invention provides both the pure enantiomers or diastereomers and mixtures thereof.

Agriculturally useful salts are in particular the salts of those cations and the acid addition salts of those acids whose cations and anions, respectively, do not adversely affect the herbicidal activity of the compounds I. Suitable cations are in particular the ions of the alkali metals, preferably sodium and potassium, of the alkaline earth metals, preferably calcium, magnesium and barium, and of the transition metals, preferably manganese, copper, zinc and iron, and the ammonium ion which, if desired, may carry one to four $C_1$–$C_4$-alkyl substituents and/or one phenyl or benzyl substituent, preferably diisopropylammonium, tetramethylammonium, tetrabutylammonium, trimethylbenzylammonium, and furthermore phosphonium ions, sulfonium ions, preferably tri($C_1$–$C_4$-alkyl) sulfonium, and sulfoxonium ions, preferably tri($C_1$–$C_4$-alkyl)sulfoxonium.

Anions of acid addition salts which may be used are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$–$C_4$-alkanoic acids, preferably formate, acetate, propionate and butyrate.

The organic moieties mentioned in the definition of $R^1$, $R^2$, $R^4$ to $R^6$, $R^8$ to $R^{15}$ and $R^{18}$ to $R^{34}$ and on phenyl, cycloalkyl and heterocyclyl rings are collective terms for individual listings of the individual group members. All hydrocarbon chains, ie. all alkyl, haloalkyl, hydroxyalkyl, cyanoalkyl, phenylalkyl, alkylideneaminooxy, alkenyl, haloalkenyl, phenylalkenyl, heterocyclylalkenyl or alkynyl moieties can be straight-chain or branched.

Halogenated substituents preferably carry one to five identical or different halogen atoms.

The term halogen represents in each case fluorine, bromine, chlorine or iodine, in particular fluorine or chlorine.

Examples of other meanings are:

$C_1$–$C_4$-alkyl: $CH_3$, $C_2H_5$, n-propyl, $CH(CH_3)_2$, n-butyl, $CH(CH_3)$—$C_2H_5$, 2-methylpropyl or $C(CH_3)_3$, in particular $CH_3$, $C_2H_5$ or $CH(CH_3)_2$;

$C_1$–$C_4$-haloalkyl: a $C_1$–$C_4$-alkyl radical as mentioned above which is partially or fully substituted by fluorine, chlorine, bromine and/or iodine, ie. for example $CH_2F$, $CHF_2$, $CF_3$, $CH_2Cl$, dichloromethyl, trichloromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl, in particular $CH_2F$, $CHF_2$, $CF_3$, $CH_2Cl$, 2-fluoroethyl, 2-chloroethyl or 2,2,2-trifluoroethyl;

$C_1$–$C_6$-alkyl: $C_1$–$C_4$-alkyl as mentioned above and, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular $CH_3$, $C_2H_5$, n-propyl, $CH(CH_3)_2$, n-butyl, $C(CH_3)_3$, n-pentyl or n-hexyl;

$C_1$–$C_6$-haloalkyl: $C_1$–$C_6$-alkyl as mentioned above which is partially or fully substituted by fluorine, chlorine, bromine and/or iodine, ie. for example one of the radicals mentioned under $C_1$–$C_4$-haloalkyl or 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl, in particular chloromethyl, fluoromethyl, difluoromethyl, trifluoromethyl, 2-fluoroethyl, 2-chloroethyl or 2,2,2-trifluoroethyl;

hydroxy-$C_1$–$C_6$-alkyl: for example hydroxymethyl, 2-hydroxyeth-1-yl, 2-hydroxyprop-1-yl, 3-hydroxyprop-1-yl, 1-hydroxyprop-2-yl, 2-hydroxybut-1-yl, 3-hydroxybut-1-yl, 4-hydroxybut-1-yl, 1-hydroxybut-2-yl, 1-hydroxybut-3-yl, 2-hydroxybut-3-yl, 1-hydroxy-2-methylprop-3-yl, 2-hydroxy-2-methylprop-3-yl or 2-hydroxymethylprop-2-yl, in particular 2-hydroxyethyl;

cyano-$C_1$–$C_6$-alkyl: for example cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl or 2-cyanomethylprop-2-yl, in particular cyanomethyl or 2-cyanoethyl;

phenyl-$C_1$–$C_6$-alkyl: for example benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(phenylmethyl)eth-1-yl 1-(phenylmethyl)-1-(methyl)eth-1-yl or 1-(phenylmethyl)prop-1-yl, in particular benzyl or 2-phenylethyl;

phenyl-($C_1$–$C_6$-alkyl)carbonyloxy: for example benzylcarbonyloxy, 1-phenylethylcarbonyloxy, 2-phenylethylcarbonyloxy, 1-phenylprop-1-ylcarbonyloxy, 2-phenylprop-1-ylcarbonyloxy, 3-phenylprop-1-ylcarbonyloxy, 1-phenylbut-1-ylcarbonyloxy, 2-phenylbut-1-ylcarbonyloxy, 3-phenylbut-1-ylcarbonyloxy, 4-phenylbut-1-ylcarbonyloxy, 1-phenylbut-2-ylcarbonyloxy, 2-phenylbut-2-ylcarbonyloxy, 3-phenylbut-2-ylcarbonyloxy, 4-phenylbut-2-ylcarbonyloxy, 1-(phenylmethyl)eth-1-ylcarbonyloxy, 1-(phenylmethyl)-1-(methyl)eth-1-ylcarbonyloxy or 1-(phenylmethyl)prop-1-ylcarbonyloxy, in particular benzylcarbonyloxy or 2-phenylethylcarbonyloxy;

phenyl-$C_1$–$C_6$-alkylsulfonyloxy: for example benzylsulfonyloxy, 1-phenylethylsulfonyloxy, 2-phenylethylsulfonyloxy, 1-phenylprop-1-ylsulfonyloxy, 2-phenylprop-1-ylsulfonyloxy, 3-phenylprop-1-ylsulfonyloxy, 1-phenylbut-1-ylsulfonyloxy, 2-phenylbut-1-ylsulfonyloxy, 3-phenylbut-1-ylsulfonyloxy, 4-phenylbut-1-ylsulfonyloxy, 1-phenylbut-2-ylsulfonyloxy, 2-phenylbut-2-ylsulfonyloxy, 3-phenylbut-2-ylsulfonyloxy, 4-phenylbut-2-ylsulfonyloxy, 1-(phenylmethyl)eth-1-ylsulfonyloxy, 1-(phenylmethyl)-1-(methyl)eth-1-ylsulfonyloxy or 1-(phenylmethyl)prop-1-ylsulfonyloxy, in particular benzylsulfonyloxy or 2-phenylethylsulfonyloxy;

($C_1$–$C_6$-alkyl)carbonyl: CO—$CH_3$, CO—$C_2H_5$, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, in particular CO—$CH_3$, CO—$C_2H_5$ or CO—$CH(CH_3)_2$;

($C_1$–$C_6$-alkyl)carbonyl-$C_1$–$C_6$-alkyl: $C_1$–$C_6$-alkyl which is substituted by ($C_1$–$C_6$-alkyl)carbonyl as mentioned above, ie. for example methylcarbonylmethyl;

($C_1$–$C_6$-haloalkyl)carbonyl: a ($C_1$–$C_6$-alkyl)carbonyl radical as mentioned above which is partially or fully substituted by fluorine, chlorine, bromine and/or iodine, ie. for example chloroacetyl, dichloroacetyl, trichloroacetyl, fluoroacetyl, difluoroacetyl, trifluoroacetyl, chlorofluoroacetyl, dichlorofluoroacetyl, chlorodifluoroacetyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, pentafluoroethylcarbonyl, 2-fluoropropylcarbonyl, 3-fluoropropylcarbonyl, 2,2-difluoropropylcarbonyl, 2,3-difluoropropylcarbonyl, 2-chloropropylcarbonyl, 3-chloropropylcarbonyl, 2,3-dichloropropylcarbonyl, 2,3-bromopropylcarbonyl, 3-bromopropylcarbonyl, 3,3,3-trifluoropropylcarbonyl, 3,3,3-trichloropropylcarbonyl, 2,2,3,3,3-pentafluoropropylcarbonyl, heptafluoropropylcarbonyl, 1-(fluoromethyl)-2-fluoroethylcarbonyl, 1-(chloromethyl)-2-chloroethylcarbonyl, 1-(bromomethyl)-2-bromoethylcarbonyl, 4-fluorobutylcarbonyl, 4-chlorobutylcarbonyl, 4-bromobutylcarbonyl, nonafluorobutylcarbonyl, (5-fluoro-1-pentyl)carbonyl, (5-chloro-1-pentyl)carbonyl, (5-bromo-1-pentyl)carbonyl, (5-iodo-1-pentyl)carbonyl, (5,5,5-trichloro-1-pentyl)carbonyl, undecafluoropentylcarbonyl, (6-fluoro-1-hexyl)carbonyl, (6-chloro-1-hexyl)carbonyl, (6-bromo-1-hexyl)carbonyl, (6-iodo-1-hexyl)carbonyl, (6,6,6-trichloro-1-hexyl)carbonyl or dodecafluorohexylcarbonyl, in particular trifluoroacetyl;

($C_1$–$C_6$-alkyl)carbonyloxy: acetyloxy, ethylcarbonyloxy, n-propylcarbonyloxy, 1-methylethylcarbonyloxy, n-butylcarbonyloxy, 1-methylpropylcarbonyloxy, 2-methylpropylcarbonyloxy, 1,1-dimethylethylcarbonyloxy, n-pentylcarbonyloxy, 1-methylbutylcarbonyloxy, 2-methylbutylcarbonyloxy, 3-methylbutylcarbonyloxy, 1,1-dimethylpropylcarbonyloxy, 1,2-dimethylpropylcarbonyloxy, 2,2-dimethylpropylcarbonyloxy, 1-ethylpropylcarbonyloxy, n-hexylcarbonyloxy, 1-methylpentylcarbonyloxy, 2-methylpentylcarbonyloxy, 3-methylpentylcarbonyloxy, 4-methylpentylcarbonyloxy, 1,1-dimethylbutylcarbonyloxy, 1,2-dimethylbutylcarbonyloxy, 1,3-dimethylbutylcarbonyloxy, 2,2-dimethylbutylcarbonyloxy, 2,3-dimethylbutylcarbonyloxy, 3,3-dimethylbutylcarbonyloxy, 1-ethylbutylcarbonyloxy, 2-ethylbutylcarbonyloxy, 1,1,2-trimethylpropylcarbonyloxy, 1,2,2-trimethylpropylcarbonyloxy, 1-ethyl-1-methylpropylcarbonyloxy or 1-ethyl-2-methylpropylcarbonyloxy, in particular acetyloxy;

($C_1$–$C_6$-haloalkyl)carbonyloxy: a ($C_1$–$C_6$-alkyl) carbonyloxy radical as mentioned above which is partially or fully substituted by fluorine, chlorine, bromine and/or iodine, ie. for example chloroacetyloxy, dichloroacetyloxy, trichloroacetyloxy, fluoroacetyloxy, difluoroacetyloxy, trifluoroacetyloxy, chlorofluoroacetyloxy, dichlorofluoroacetyloxy, chlorodifluoroacetyloxy, 2-fluoroethylcarbonyloxy, 2-chloroethylcarbonyloxy, 2-bromoethylcarbonyloxy, 2-iodoethylcarbonyloxy, 2,2-difluoroethylcarbonyloxy, 2,2,2-trifluoroethylcarbonyloxy, 2-chloro-2-fluoroethylcarbonyloxy, 2-chloro-2,2-difluoroethylcarbonyloxy, 2,2-dichloro-2-fluoroethylcarbonyloxy, 2,2,2-trichloroethylcarbonyloxy, pentafluoroethylcarbonyloxy, 2-fluoropropylcarbonyloxy, 3-fluoropropylcarbonyloxy, 2,2-difluoropropylcarbonyloxy, 2,3-difluoropropylcarbonyloxy, 2-chloropropylcarbonyloxy, 3-chloropropylcarbonyloxy, 2,3-dichloropropylcarbonyloxy, 2-bromopropylcarbonyloxy, 3-bromopropylcarbonyloxy, 3,3,3-trifluoropropylcarbonyloxy, 3,3,3-trichloropropylcarbonyloxy, 2,2,3,3,3-pentafluoropropylcarbonyloxy, heptafluoropropylcarbonyloxy, 1-(fluoromethyl)-2-fluoroethylcarbonyloxy, 1-(chloromethyl)-2-chloroethylcarbonyloxy, 1-(bromomethyl)-2-bromoethylcarbonyloxy, 4-fluorobutylcarbonyloxy, 4-chlorobutylcarbonyloxy, 4-bromobutyl or nonafluorobutyl, in particular trifluoroacetoxy;

($C_1$–$C_6$-alkyl)carbonyloxy-$C_1$–$C_6$-alkyl: $C_1$–$C_6$-alkyl which is substituted by ($C_1$–$C_6$-alkyl)carbonyloxy as mentioned above, ie. for example methylcarbonyloxymethyl, ethylcarbonyloxymethyl, 1-(methylcarbonyloxy)ethyl, 2-(methylcarbonyloxy)ethyl, 2-(ethylcarbonyloxy)ethyl, 3-(methylcarbonyloxy)propyl, 4-(methoxycarbonyloxy)butyl, 5-(methoxycarbonyloxy)pentyl or 6-(methoxycarbonyloxy)hexyl;

($C_1$–$C_6$-alkyl)carbonylthio: acetylthio, ethylcarbonylthio, n-propylcarbonylthio, 1-methylethylcarbonylthio, n-butylcarbonylthio, 1-methylpropylcarbonylthio, 2-methylpropylcarbonylthio, 1,1-dimethylethylcarbonylthio, n-pentylcarbonylthio, 1-methylbutylcarbonylthio, 2-methylbutylcarbonylthio, 3-methylbutylcarbonylthio, 1,1-dimethylpropylcarbonylthio, 1,2-dimethylpropylcarbonylthio, 2,2-dimethylpropylcarbonylthio, 1-ethylpropylcarbonylthio, n-hexylcarbonylthio, 1-methylpentylcarbonylthio, 2-methylpentylcarbonylthio, 3-methylpentylcarbonylthio, 4-methylpentylcarbonylthio, 1,1-dimethylbutylcarbonylthio, 1,2-dimethylbutylcarbonylthio, 1,3-dimethylbutylcarbonylthio, 2,2-dimethylbutylcarbonylthio, 2,3-dimethylbutylcarbonylthio, 3,3-dimethylbutylcarbonylthio, 1-ethylbutylcarbonylthio, 2-ethylbutylcarbonylthio, 1,1,2-trimethylpropylcarbonylthio, 1,2,2-trimethylpropylcarbonylthio, 1-ethyl-1-methylpropylcarbonylthio or 1-ethyl-2-methylpropylcarbonylthio, in particular acetylthio;

($C_1$–$C_6$-haloalkyl)carbonylthio: a ($C_1$–$C_6$-alkyl) carbonylthio radical as mentioned above which is partially or fully substituted by fluorine, chlorine, bromine and/or iodine, ie. for example chloroacetylthio, dichloroacetylthio, trichloroacetylthio, fluoroacetylthio, difluoroacetylthio, trifluoroacetylthio, chlorofluoroacetylthio, dichlorofluoroacetylthio, chlorodifluoroacetylthio, 2-fluoroethylcarbonylthio, 2-chloroethylcarbonylthio, 2-bromoethylcarbonylthio, 2-iodoethylcarbonylthio, 2,2-difluoroethylcarbonylthio, 2,2,2-trifluoroethylcarbonylthio, 2-chloro-2-fluoroethylcarbonylthio, 2-chloro-2,2-difluoroethylcarbonylthio, 2,2-dichloro-2-fluoroethylcarbonylthio, 2,2,2-trichloroethylcarbonylthio, pentafluoroethylcarbonylthio, 2-fluoropropylcarbonylthio, 3-fluoropropylcarbonylthio, 2,2-difluoropropylcarbonylthio, 2,3-difluoropropylcarbonylthio, 2-chloropropylcarbonylthio, 3-chloropropylcarbonylthio, 2,3-dichloropropylcarbonylthio, 2-bromopropylcarbonylthio, 3-bromopropylcarbonylthio, 3,3,3-trifluoropropylcarbonylthio, 3,3,3-trichloropropylcarbonylthio, 2,2,3,3,3-pentafluoropropylcarbonylthio, heptafluoropropylcarbonylthio, 1-(fluoromethyl)-2-fluoroethylcarbonylthio, 1-(chloromethyl)-2-chloroethylcarbonylthio, 1-(bromomethyl)-2-bromoethylcarbonylthio, 4-fluorobutylcarbonylthio, 4-chlorobutylcarbonylthio, 4-bromobutylthio or nonafluorobutylthio, in particular trifluoroacetylthio;

$C_1$–$C_4$-alkoxy: $OCH_3$, $OC_2H_5$, n-propoxy, $OCH(CH_3)_2$, n-butoxy, 1-methylpropoxy, $OCH_2$—$CH(CH_3)_2$ or $OC(CH_3)_3$, in particular $OCH_3$ or $OC_2H_5$;

$C_1$–$C_6$-alkoxy: $C_1$–$C_4$-alkoxy as mentioned above and, for example, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, in particular methoxy, ethoxy or 1-methylethoxy;

$C_1$–$C_4$-haloalkoxy: a $C_1$–$C_4$-alkoxy radical as mentioned above which is partially or fully substituted by fluorine, chlorine, bromine and/or iodine, ie. for example chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy, in particular 2-chloroethoxy or 2,2,2-trifluoroethoxy;

$C_1$–$C_6$-haloalkoxy: a $C_1$–$C_6$-alkoxy radical as mentioned above which is partially or fully substituted by fluorine, chlorine, bromine and/or iodine, ie. for example one of the radicals mentioned under $C_1$–$C_4$-haloalkoxy or 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, in particular chloromethoxy, fluoromethoxy, difluoromethoxy, trifluoromethoxy, 2-fluoroethoxy, 2-chloroethoxy or 2,2,2-trifluoroethoxy;

phenyl-$C_1$–$C_6$-alkoxy: for example benzyloxy, 1-phenylethoxy, 2-phenylethoxy, 1-phenylprop-1-yloxy, 2-phenylprop-1-yloxy, 3-phenylprop-1-yloxy, 1-phenylbut-1-yloxy, 2-phenylbut-1-yloxy, 3-phenylbut-1-yloxy, 4-phenylbut-1-yloxy, 1-phenylbut-2-yloxy, 2-phenylbut-2-yloxy, 3-phenylbut-2-yloxy, 4-phenylbut-2-yloxy, 1-(phenylmethyl)eth-1-yloxy, 1-(phenylmethyl)-1-(methyl)eth-1-yloxy or 1-(phenylmethyl)prop-1-yloxy, in particular benzyloxy or 2-phenylethoxy;

phenyl-$C_1$–$C_6$-alkylthio: for example benzylthio, 1-phenylethylthio, 2-phenylethylthio, 1-phenylprop-1-ylthio, 2-phenylprop-1-ylthio, 3-phenylprop-1-ylthio, 1-phenylbut-1-ylthio, 2-phenylbut-1-ylthio, 3-phenylbut-1-ylthio, 4-phenylbut-1-ylthio, 1-phenylbut-2-ylthio, 2-phenylbut-2-ylthio, 3-phenylbut-2-ylthio, 4-phenylbut-2-ylthio, 1-(phenylmethyl)-eth-1-ylthio, 1-(phenylmethyl)-1-(methyl)eth-1-ylthio or 1-(phenylmethyl)prop-1-ylthio, in particular benzylthio or 2-phenylethylthio;

($C_1$–$C_4$-alkoxy)carbonyl: CO—$OCH_3$, CO—$OC_2H_5$, n-propoxycarbonyl, CO—$OCH(CH_3)_2$, n-butoxycarbonyl, 1-methylpropoxycarbonyl, CO—$OCH_2$—$CH(CH_3)_2$ or CO—$OC(CH_3)_3$, in particular CO—$OCH_3$, CO—$OC_2H_5$, CO—$OCH(CH_3)_2$ or CO—$CH_2$—$CH(CH_3)_2$;

($C_1$–$C_6$-alkoxy)carbonyl: ($C_1$–$C_4$-alkoxy)carbonyl as mentioned above and, for example, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, in particular methoxycarbonyl, ethoxycarbonyl or 1-methylethoxycarbonyl;

($C_1$–$C_6$-alkoxy)carbonyloxy: methoxycarbonyloxy, ethoxycarbonyloxy, n-propoxycarbonyloxy, 1-methylethoxycarbonyloxy, n-butoxycarbonyloxy, 1-methylpropoxycarbonyloxy, 2-methylpropoxycarbonyloxy, 1,1-dimethylethoxycarbonyloxy, n-pentoxycarbonyloxy, 1-methylbutoxycarbonyloxy, 2-methylbutoxycarbonyloxy, 3-methylbutoxycarbonyloxy, 2,2-dimethylpropoxycarbonyloxy, 1-ethylpropoxycarbonyloxy, n-hexoxycarbonyloxy, 1,1-dimethylpropoxycarbonyloxy, 1,2-dimethylpropoxycarbonyloxy, 1-methylpentoxycarbonyloxy, 2-methylpentoxycarbonyloxy, 3-methylpentoxycarbonyloxy, 4-methylpentoxycarbonyloxy, 1,1-dimethylbutoxycarbonyloxy, 1,2-dimethylbutoxycarbonyloxy, 1,3-dimethylbutoxycarbonyloxy, 2,2-dimethylbutoxycarbonyloxy, 2,3-dimethylbutoxycarbonyloxy, 3,3-dimethylbutoxycarbonyloxy, 1-ethylbutoxycarbonyloxy, 2-ethylbutoxycarbonyloxy, 1,1,2-trimethylpropoxycarbonyloxy, 1,2,2-trimethylpropoxycarbonyloxy, 1-ethyl-1-methylpropoxycarbonyloxy or 1-ethyl-2-methylpropoxycarbonyloxy, in particular methoxycarbonyloxy, ethoxycarbonyloxy or 1-methylethoxycarbonyloxy;

$(C_1-C_6$-alkoxy)carbonylthio: methoxycarbonylthio, ethoxycarbonylthio, n-propoxycarbonylthio, 1-methylethoxycarbonylthio, n-butoxycarbonylthio, 1-methylpropoxycarbonylthio, 2-methylpropoxycarbonylthio, 1,1-dimethylethoxycarbonylthio, n-pentoxycarbonylthio, 1-methylbutoxycarbonylthio, 2-methylbutoxycarbonylthio, 3-methylbutoxycarbonylthio, 2,2-dimethylpropoxycarbonylthio, 1-ethylpropoxycarbonylthio, n-hexoxycarbonylthio, 1,1-dimethylpropoxycarbonylthio, 1,2-dimethylpropoxycarbonylthio, 1-methylpentoxycarbonylthio, 2-methylpentoxycarbonylthio, 3-methylpentoxycarbonylthio, 4-methylpentoxycarbonylthio, 1,1-dimethylbutoxycarbonylthio, 1,2-dimethylbutoxycarbonylthio, 1,3-dimethylbutoxycarbonylthio, 2,2-dimethylbutoxycarbonylthio, 2,3-dimethylbutoxycarbonylthio, 3,3-dimethylbutoxycarbonylthio, 1-ethylbutoxycarbonylthio, 2-ethylbutoxycarbonylthio, 1,1,2-trimethylpropoxycarbonylthio, 1,2,2-trimethylpropoxycarbonylthio, 1-ethyl-1-methylpropoxycarbonylthio or 1-ethyl-2-methylpropoxycarbonylthio, in particular methoxycarbonylthio, ethoxycarbonylthio or 1-methylethoxycarbonylthio;

$C_1-C_6$-alkylthio: $SCH_3$, $SC_2H_5$, $SCH_2-C_2H_5$, $SCH(CH_3)_2$, n-butylthio, 1-methylpropylthio, 2-methylpropylthio, $SC(CH_3)_3$, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio, in particular $SCH_3$ or $SC_2H_5$;

$C_1-C_4$-haloalkylthio: $C_1-C_4$-alkylthio such as methylthio, ethylthio, n-propylthio, 1-methylethylthio, n-butylthio, 1-methylpropylthio, 2-methylpropylthio and 1,1-dimethylethylthio, preferably methylthio or ethylthio, which is partially or fully substituted by fluorine, chlorine and/or bromine, ie. for example $SCHF_2$, $SCF_3$, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, $SC_2F_5$, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio, in particular $SCHF_2$ or $SCF_3$;

$C_1-C_6$-haloalkylthio: $C_1-C_6$-alkylthio as mentioned above which is partially or fully substituted by fluorine, chlorine and/or bromine, ie. for example one of the radicals mentioned under $C_1-C_4$-haloalkylthio or 5-fluoropentylthio, 5-chloropentylthio, 5-bromopentylthio, 5-iodopentylthio, undecafluoropentylthio, 6-fluorohexylthio or 6-chlorohexylthio, in particular $SCH_2F$, $SCHF_2$, $SCF_3$, $SCH_2Cl$, 2-fluoroethylthio, 2-chloroethylthio or 2,2,2-trifluoroethylthio;

$C_1-C_6$-alkylsulfinyl: $SO-CH_3$, $SO-C_2H_5$, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl, in particular $SO-CH_3$;

$C_1-C_6$-alkylsulfonyl: $SO_2-CH_3$, $SO_2-C_2H_5$, n-propylsulfonyl, $SO_2-CH(CH_3)_2$, n-butylsulfonyl, 1-methylpropylsulfonyl, 2-methylpropylsulfonyl, $SO_2-C(CH_3)_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl, in particular $SO_2$—$CH_3$;

$C_1$–$C_6$-alkylsulfonyloxy: O—$SO_2$—$CH_3$, O—$SO_2$—$C_2H_5$, n-propylsulfonyloxy, O—$SO_2$—$CH(CH_3)_2$, n-butylsulfonyloxy, 1-methylpropylsulfonyloxy, 2-methylpropylsulfonyloxy, O—$SO_2$—$C(CH_3)_3$, n-pentylsulfonyloxy, 1-methylbutylsulfonyloxy, 2-methylbutylsulfonyloxy, 3-methylbutylsulfonyloxy, 1,1-dimethylpropylsulfonyloxy, 1,2-dimethylpropylsulfonyloxy, 2,2-dimethylpropylsulfonyloxy, 1-ethylpropylsulfonyloxy, n-hexylsulfonyloxy, 1-methylpentylsulfonyloxy, 2-methylpentylsulfonyloxy, 3-methylpentylsulfonyloxy, 4-methylpentylsulfonyloxy 1,1-dimethylbutylsulfonyloxy, 1,2-dimethylbutylsulfonyloxy, 1,3-dimethylbutylsulfonyloxy, 2,2-dimethylbutylsulfonyloxy, 2,3-dimethylbutylsulfonyloxy, 3,3-dimethylbutylsulfonyloxy, 1-ethylbutylsulfonyloxy, 2-ethylbutylsulfonyloxy, 1,1,2-trimethylpropylsulfonyloxy, 1,2,2-trimethylpropylsulfonyloxy, 1-ethyl-1-methylpropylsulfonyloxy or 1-ethyl-2-methylpropylsulfonyloxy, in particular methylsulfonyloxy;

$C_1$–$C_6$-haloalkylsulfonyloxy: $C_1$–$C_6$-alkylsulfonyloxy as mentioned above which is partially or fully substituted by fluorine, chlorine, bromine and/or iodine, ie. for example $ClCH_2$—$SO_2$—O—, $CH(Cl)_2$—$SO_2$—O—, $C(Cl)_3$—$SO_2$—O—, $FCH_2$—$SO_2$—O—, $CHF_2$—$SO_2$—O—, $CF_3$—$SO_2$—O—, chlorofluoromethyl-$SO_2$—O—, dichlorofluoromethyl-$SO_2$—O—, chlorodifluoromethyl-$SO_2$—O—, 1-fluoroethyl-$SO_2$—O—, 2-fluoroethyl-$SO_2$—O—, 2-chloroethyl-$SO_2$—O—, 2-bromoethyl-$SO_2$—O—, 2-iodoethyl-$SO_2$—O—, 2,2-difluoroethyl-$SO_2$—O—, 2,2,2-trifluoroethyl-$SO_2$—O—, 2-chloro-2-fluoroethyl-$SO_2$—O—, 2-chloro-2,2-difluoroethyl-$SO_2$—O—, 2,2-dichloro-2-fluoroethyl-$SO_2$—O—, 2,2,2-trichloroethyl-$SO_2$—O—, $C_2F_5$—$SO_2$—O—, 2-fluoropropyl-$SO_2$—O—, 3-fluoropropyl-$SO_2$—O—, 2,2-difluoropropyl-$SO_2$—O—, 2,3-difluoropropyl-$SO_2$—O—, 2-chloropropyl-$SO_2$—O—, 3-chloropropyl-$SO_2$—O—, 2,3-dichloropropyl-$SO_2$—O—, 2-bromopropyl-$SO_2$—O—, 3-bromopropyl-$SO_2$—O—, 3,3,3-trifluoropropyl-$SO_2$—O—, 3,3,3-trichloropropyl-$SO_2$—O—, 2,2,3,3,3-pentafluoropropyl-$SO_2$—O—, $C_2F_5$—$CF_2$—$SO_2$—O—, 1-(fluoromethyl)-2-fluoroethyl-$SO_2$—O—, 1-(chloromethyl)-2-chloroethyl-$SO_2$—O—, 1-(bromomethyl)-2-bromoethyl-$SO_2$—O—, 4-fluorobutyl-$SO_2$—O—, 4-chlorobutyl-$SO_2$—O—, 4-bromobutyl-$SO_2$—O—, $C_2F_5$—$CF_2$—$CF_2$—$SO_2$—O—, 5-fluoropentyl-$SO_2$—O—, 5-chloropentyl-$SO_2$—O—, 5-bromopentyl-$SO_2$—O—, 5-iodopentyl-$SO_2$—O—, 5,5,5-trichloropentyl-$SO_2$—O—, $C_2F_5$—$CF_2$—$CF_2$—$CF_2$—$SO_2$—O—, 6-fluorohexyl-$SO_2$—O—, 6-chlorohexyl-$SO_2$—O—, 6-bromohexyl-$SO_2$—O—, 6-iodohexyl-$SO_2$—O—, 6,6,6-trichlorohexyl-$SO_2$—O— or dodecafluorohexyl-$SO_2$—O—, in particular $CF_3$—$SO_2$—O—;

$C_1$–$C_6$-alkylamino: e.g. NH—$CH_3$, NH—$C_2H_5$, NH—$CH_2$—$C_2H_5$, NH—$CH(CH_3)_2$, n-butylamino, 1-methylpropylamino, 2-methylpropylamino, NH—$C(CH_3)_3$, NH—(n—$C_5H_{11}$) or NH—(n—$C_6H_{13}$), in particular $C_1$–$C_4$-alkylamino;

($C_1$–$C_4$-alkyl)aminocarbonyl: CO—NH—$CH_3$, CO—NH—$C_2H_5$, CO—NH—$CH_2$—$C_2H_5$, CO—NH—$CH(CH_3)_2$, n-butylaminocarbonyl, CO—NH—$CH(CH_3)$—$C_2H_5$, CO—NH—$CH_2$—$CH(CH_3)_2$ or CO—NH—$C(CH_3)_3$, in particular CO—NH—$CH_3$ or CO—NH—$C_2H_5$;

($C_1$–$C_6$-alkyl)aminocarbonyl: ($C_1$–$C_4$-alkyl)aminocarbonyl as mentioned above and, for example, n-pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, n-hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl, in particular CO—NH—$CH_3$, CO—NH—$C_2H_5$ or CO—NH—$CH(CH_3)_2$;

di($C_1$–$C_6$-alkyl)aminocarbonyl: for example N,N-dimethylaminocarbonyl, N,N-diethylaminocarbonyl, N,N-dipropylaminocarbonyl, N,N-di(1-methylethyl)aminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-

(2-methylpropyl)aminocarbonyl, N-(1,1-dimethylethyl)-N-(1-methylpropyl)aminocarbonyl or N-(1,1-dimethylethyl)-N-(2-methylpropyl) aminocarbonyl, in particular N,N-dimethylaminocarbonyl or N,N-diethylaminocarbonyl;

($C_1$–$C_6$-alkyl)iminooxycarbonyl: methyliminooxycarbonyl, ethyliminooxycarbonyl, n-propyliminooxycarbonyl, 1-methylethyliminooxycarbonyl, n-Butyliminooxycarbonyl, 1-methylpropyliminooxycarbonyl, 2-methylpropyliminooxycarbonyl, 1,1-dimethylethyliminooxycarbonyl, n-pentyliminooxycarbonyl, 1-methylbutyliminooxycarbonyl, 2-methylbutyliminooxycarbonyl, 3-methylbutyliminooxycarbonyl, 1,1-dimethylpropyliminooxycarbonyl, 1,2-dimethylpropyliminooxycarbonyl, 2,2-dimethylpropyliminooxycarbonyl, 1-ethylpropyliminooxycarbonyl, n-hexyliminooxycarbonyl, 1-methylpentyliminooxycarbonyl, 2-methylpentyliminooxycarbonyl, 3-methylpentyliminooxycarbonyl, 4-methylpentyliminooxycarbonyl, 1,1-dimethylbutyliminooxycarbonyl, 1,2-dimethylbutyliminooxycarbonyl, 1,3-dimethylbutyliminooxycarbonyl, 2,2-dimethylbutyliminooxycarbonyl, 2,3-dimethylbutyliminooxycarbonyl, 3,3-dimethylbutyliminooxycarbonyl, 1-ethylbutyliminooxycarbonyl, 2-ethylbutyliminooxycarbonyl, 1,1,2-trimethylpropyliminooxycarbonyl, 1,2,2-trimethylpropyliminooxycarbonyl, 1-ethyl-1-methylpropyliminooxycarbonyl or 1-ethyl-2-methylpropyliminooxycarbonyl, in particular methyliminooxycarbonyl, ethyliminooxycarbonyl or 1-methylethyliminooxycarbonyl;

$C_1$–$C_6$-alkylideneaminooxy: acetylideneaminooxy, 1-propylideneaminooxy, 2-propylideneaminooxy, 1-butylideneaminooxy, 2-butylideneaminooxy or 2-hexylideneaminooxy, in particular acetylideneaminooxy or 2-propylideneaminooxy;

$C_1$–$C_6$-alkyliminooxy: methyliminooxy, ethyliminooxy, n-propyliminooxy, 1-methylethyliminooxy, n-butyliminooxy, 1-methylpropyliminooxy, 2-methylpropyliminooxy, n-pentyliminooxy, n-hexyliminooxy, 1-methylpentyliminooxy, 2-methylpentyliminooxy, 3-methylpentyliminooxy or 4-methylpentyliminooxy, in particular methyliminooxy, ethyliminooxy or 1-methylethyliminooxy;

$C_1$–$C_6$-alkyloximino-$C_1$–$C_6$-alkyl: $C_1$–$C_6$-alkyl which is substituted by $C_1$–$C_6$-alkyloximino such as methoxyimino, ethoxyimino, 1-propoxyimino, 2-propoxyimino, 1-methylethoxyimino, n-butoxyimino, sec-butoxyimino, tert-butoxyimino, 1-methyl-1-propoxyimino, 2-methyl-1-propoxyimino, 1-methyl-2-propoxyimino, 2-methyl-2-propoxyimino, n-pentoxyimino, 2-pentoxyimino, 3-pentoxyimino, 4-pentoxyimino, 1-methyl-1-butoxyimino, 2-methyl-1-butoxyimino, 3-methyl-1-butoxyimino, 1-methyl-2-butoxyimino, 2-methyl-2-butoxyimino, 3-methyl-2-butoxyimino, 1-methyl-3-butoxyimino, 2-methyl-3-butoxyimino, 3-methyl-3-butoxyimino, 1,1-dimethyl-2-propoxyimino, 1,2-dimethyl-1-propoxyimino, 1,2-dimethyl-2-propoxyimino, 1-ethyl-1-propoxyimino, 1-ethyl-2-propoxyimino, n-hexoxyimino, 2-hexoxyimino, 3-hexoxyimino, 4-hexoxyimino, 5-hexoxyimino, 1-methyl-1-pentoxyimino, 2-methyl-1-pentoxyimino, 3-methyl-1-pentoxyimino, 4-methyl-1-pentoxyimino, 1-methyl-2-pentoxyimino, 2-methyl-2-pentoxyimino, 3-methyl-2-pentoxyimino, 4-methyl-2-pentoxyimino, 1-methyl-3-pentoxyimino, 2-methyl-3-pentoxyimino, 3-methyl-3-pentoxyimino, 4-methyl-3-pentoxyimino, 1-methyl-4-pentoxyimino, 2-methyl-4-pentoxyimino, 3-methyl-4-pentoxyimino, 4-methyl-4-pentoxyimino, 1,1-dimethyl-2-butoxyimino, 1,1-dimethyl-3-butoxyimino, 1,2-dimethyl-1-butoxyimino, 1,2-dimethyl-2-butoxyimino, 1,2-dimethyl-3-butoxyimino, 1,3-dimethyl-1-butoxyimino, 1,3-dimethyl-2-butoxyimino, 1,3-dimethyl-3-butoxyimino, 2,2-dimethyl-3-butoxyimino, 2,3-dimethyl-1-butoxyimino, 2,3-dimethyl-2-butoxyimino, 2,3-dimethyl-3-butoxyimino, 3,3-dimethyl-1-butoxyimino, 3,3-dimethyl-2-butoxyimino, 1-ethyl-1-butoxyimino, 1-ethyl-2-butoxyimino, 1-ethyl-3-butoxyimino, 2-ethyl-1-butoxyimino, 2-ethyl-2-butoxyimino, 2-ethyl-3-butoxyimino, 1,1,2-trimethyl-2-propoxyimino, 1-ethyl-1-methyl-2-propoxyimino, 1-ethyl-2-methyl-1-propoxyimino and 1-ethyl-2-methyl-2-propoxyimino, ie. for example methoxyiminomethyl;

$C_1$–$C_6$-alkoxy-$C_1$–$C_6$-alkyl: $C_1$–$C_6$-alkyl which is substituted by $C_1$–$C_6$-alkoxy as mentioned above, ie. for example $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, in particular $CH_2$—$OCH_3$ or 2-methoxyethyl;

$C_1$–$C_6$-alkoxy-$C_1$–$C_6$-alkoxy: $C_1$–$C_6$-alkoxy which is substituted by $C_1$–$C_6$-alkoxy as mentioned above, ie. for example $OCH_2$—$OCH_3$, $OCH_2$—$OC_2H_5$, n-propoxymethoxy, $OCH_2$—$OCH(CH_3)_2$, n-butoxymethoxy, (1-methylpropoxy)methoxy, (2-methylpropoxy)methoxy, $OCH_2$—$OC(CH_3)_3$, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2- methylpropoxy)ethoxy, 2-(1,1-dimethylethoxy)ethoxy, 2-(methoxy)propoxy, 2-(ethoxy)propoxy, 2-(n-propoxy)propoxy, 2-(1-methylethoxy)propoxy, 2-(n-butoxy)propoxy, 2-(1-methylpropoxy)propoxy, 2-(2-methylpropoxy)propoxy, 2-(1,1-dimethylethoxy) propoxy, 3-(methoxy)propoxy, 3-(ethoxy)propoxy, 3-(n-propoxy)propoxy, 3-(1-methylethoxy)propoxy, 3-(n-butoxy)propoxy, 3-(1-methylpropoxy)propoxy, 3-(2-methylpropoxy)propoxy, 3-(1,1-dimethylethoxy) propoxy, 2-(methoxy)butoxy, 2-(ethoxy)butoxy, 2-(n-propoxy)butoxy, 2-(1-methylethoxy)butoxy, 2-(n-butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(n-propoxy) butoxy, 3-(1-methylethoxy)butoxy, 3-(n-butoxy) butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(n-propoxy) butoxy, 4-(1-methylethoxy)butoxy, 4-(n-butoxy) butoxy, 4-(1-methylpropoxy)butoxy, 4-(2-methylpropoxy)butoxy, 4-(1,1-dimethylethoxy)butoxy, 5-(methoxy)pentoxy, 5-(ethoxy)pentoxy, 5-(n-propoxy)pentoxy, 5-(1-methylethoxy)pentoxy, 5-(n-butoxy)pentoxy, 5-(1-methylpropoxy)pentoxy, 5-(2-methylpropoxy)pentoxy, 5-(1,1-dimethylethoxy) pentoxy, 6-(methoxy)hexoxy, 6-(ethoxy)hexoxy, 6-(n-propoxy)hexoxy, 6-(1-methylethoxy)hexoxy, 6-(n-butoxy)hexoxy, 6-(1-methylpropoxy)hexoxy, 6-(2-methylpropoxy)hexoxy or 6-(1,1-dimethylethoxy) hexoxy, in particular $OCH_2$—$OCH_3$ or $OCH_2$—$OC_2H_5$;

$(C_1-C_6$-alkoxy)carbonyl-$C_1-C_6$-alkoxy: $C_1-C_6$-alkoxy which is substituted by $(C_1-C_6$-alkoxy)carbonyl as mentioned above, ie. for example $OCH_2$—CO—$OCH_3$, $OCH_2$—CO—$OC_2H_5$, $OCH_2$—CO—$OCH_2$—$C_2H_5$, $OCH_2$—CO—$OCH(CH_3)_2$, n-butoxycarbonylmethoxy, 1-(methoxycarbonyl) ethoxy, 2-(methoxycarbonyl)ethoxy, 2-(ethoxycarbonyl)ethoxy, 2-(n-propoxycarbonyl) ethoxy, 2-(n-butoxycarbonyl)ethoxy, 3-(methoxycarbonyl)propoxy, 3-(ethoxycarbonyl) propoxy, 3-(n-propoxycarbonyl)propoxy, 3-(n-butoxycarbonyl)propoxy, 4-(methoxycarbonyl)butoxy, 4-(ethoxycarbonyl)butoxy, 4-(n-propoxycarbonyl) butoxy, 4-(n-butoxycarbonyl)butoxy, 5-(methoxycarbonyl)pentoxy, 5-(ethoxycarbonyl) pentoxy, 5-(n-propoxycarbonyl)pentoxy, 5-(n-butoxycarbonyl)butoxy, 6-(methoxycarbonyl)hexoxy, 6-(ethoxycarbonyl)hexoxy, 6-(n-propoxycarbonyl) hexoxy or 6-(n-butoxycarbonyl)hexoxy, in particular $OCH_2$—CO—$OCH_3$ or 1-(methoxycarbonyl)ethoxy;

$(C_1-C_6$-alkoxy)carbonyl-$C_1-C_6$-alkyl: $C_1-C_6$-alkyl which is substituted by $(C_1-C_6$-alkoxy)carbonyl as mentioned above, ie. for example methoxycarbonylmethyl, ethoxycarbonylmethyl, 1-(methoxycarbonyl)ethyl, 2-(methoxycarbonyl)ethyl, 2-(ethoxycarbonyl)ethyl, 3-(methoxycarbonyl)propyl, 4-(methoxycarbonyl)butyl, 5-(methoxycarbonyl)pentyl or 6-(methoxycarbonyl)hexyl;

$(C_1-C_6$-alkoxy)carbonyl-$C_1-C_6$-alkylsulfonyl: $C_1-C_6$-alkylsulfonyl which is substituted by $(C_1-C_6$-alkoxy) carbonyl as mentioned above, ie. for example methoxycarbonylmethylsulfonyl, ethoxycarbonylmethylsulfonyl, 1-(methoxycarbonyl) ethylsulfonyl, 2-(methoxycarbonyl)ethylsulfonyl, 2-(ethoxycarbonyl)ethylsulfonyl, 3-(methoxycarbonyl) propylsulfonyl, 4-(methoxycarbonyl)butylsulfonyl, 5-(methoxycarbonyl)pentylsulfonyl or 6-(methoxycarbonyl)hexylsulfonyl;

$C_1-C_6$-alkylthio-$C_1-C_6$-alkyl: $C_1-C_6$-alkyl which is substituted by $C_1-C_6$-alkylthio as mentioned above, ie. for example $CH_2$—$SCH_3$, $CH_2$—$SC_2H_5$, n-propylthiomethyl, $CH_2$—$SCH(CH_3)_2$, n-butylthiomethyl, (1-methylpropylthio)methyl, $CH_2$—$SCH_2$—$CH(CH_3)_2$, $CH_2$—$SC(CH_3)_3$, 2-methylthioethyl, 2-ethylthioethyl, 2-(n-propylthio) ethyl, 2-(1-methylethylthio)ethyl, 2-(n-butylthio)ethyl, 2-(1-methylpropylthio)ethyl, 2-(2-methylpropylthio) ethyl, 2-(1,1-dimethylethylthio)ethyl, 2-(methylthio) propyl, 3-(methylthio)propyl, 2-(ethylthio)propyl, 3-(ethylthio)propyl, 3-(propylthio)propyl, 3-(butylthio) propyl, 4-(methylthio)butyl, 4-(ethylthio)butyl, 4-(n-propylthio)butyl or 4-(n-butylthio)butyl, in particular 2-(methylthio)ethyl;

$C_1-C_6$-alkylthio-$(C_1-C_6$-alkyl)carbonyl: $(C_1-C_6$-alkyl) carbonyl which is substituted by $C_1-C_6$-alkylthio as mentioned above, preferably by $SCH_3$ or $SC_2H_5$, ie. for example methylthiomethylcarbonyl, ethylthiomethylcarbonyl, 1-(methylthio)ethylcarbonyl, 2-(methylthio)ethylcarbonyl, 3-(methylthio) propylcarbonyl, 4-(methylthio)butylcarbonyl, 5-(methylthio)pentylcarbonyl or 6-(methylthio) hexylcarbonyl, in particular CO—$CH_2$—$SCH_3$ or CO—$CH(CH_3)$—$SCH_3$;

di($C_1-C_6$-alkyl)amino-$C_1-C_6$-alkoxy: $C_1-C_6$-alkoxy which is substituted by di($C_1-C_6$-alkyl)amino such as $N(CH_3)_2$, $N(C_2H_5)_2$, N,N-dipropylamino, N,N-di(1-methylethyl)amino, N,N-dibutylamino, N,N-di(1-methylpropyl)amino, N,N-di(2-methylpropyl)amino, $N[C(CH_3)_3]_2$, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl) amino, N-(1,1-dimethylethyl)-N-methylamino, N-ethyl-N-propylamino, N-ethyl-N-(1-methylethyl) amino, N-butyl-N-ethylamino, N-ethyl-N-1-methylpropyl)amino, N-ethyl-N-(2-methylpropyl) amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl) amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino, preferably by N,N-dimethylamino or N,N-diethylamino, ie. for example $OCH_2$—$N(CH_3)_2$, $OCH_2$—$N(C_2H_5)_2$, $OCH(CH_3)$—$N(CH_3)_2$, 2-(dimethylamino)ethoxy, $OCH(CH_3)$—$N(C_2H_5)_2$, 3-(dimethylamino)propoxy, 4-(dimethylamino)butoxy, 5-(dimethylamino)pentoxy or 6-(dimethylamino)hexoxy, in particular $OCH_2$—$N(CH_3)_2$ or $OCH(CH_3)$—$N(CH_3)_2$;

$C_3-C_6$-alkenyl: for example prop-2-en-1-yl, n-buten-4-yl, 1-methylprop-2-en-1-yl, 2-methylprop-2-en-1-yl, 2-buten-1-yl, n-penten-3-yl, n-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, n-hex-3-en-1-yl, n-hex-4-en-1-yl, n-hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl, in particular prop-2-en-1-yl or n-buten-4-yl;

$C_2$–$C_6$-alkenyl: ethenyl or one of the radicals mentioned under $C_3$–$C_6$-alkenyl, in particular ethenyl or prop-2-en-1-yl;

$C_3$–$C_6$-haloalkenyl: $C_3$–$C_6$-alkenyl as mentioned above which is partially or fully substituted by fluorine, chlorine and/or bromine, ie. for example 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl, in particular 2-chloroallyl or 3,3-dichloroallyl;

phenyl-$C_3$–$C_6$-alkenyloxy: for example 3-phenylallyloxy, 4-phenylbut-2-enyloxy, 4-phenylbut-3-enyloxy or 5-phenylpent-4-enyloxy, preferably 3-phenylallyloxy or 4-phenylbut-2-enyloxy, in particular 3-phenylallyloxy;

heterocyclyl-$C_3$–$C_6$-alkenyloxy: for example 3-heterocyclylallyloxy, 4-heterocyclylbut-2-enyloxy, 4-heterocyclylbut-3-enyloxy or 5-heterocyclylpent-4-enyloxy, preferably 3-heterocyclylallyloxy or 4-heterocyclylbut-2-enyloxy, in particular 3-heterocyclylallyloxy;

$C_3$–$C_6$-alkenyloxy: prop-1-en-1-yloxy, prop-2-en-1-yloxy, 1-methylethenyloxy, n-buten-1-yloxy, n-buten-2-yloxy, n-buten-3-yloxy, 1-methylprop-1-en-1-yloxy, 2-methylprop-1-en-1-yloxy, 1-methyl-prop-2-en-1-yloxy, 2-methylprop-2-en-1-yloxy, n-penten-1-yloxy, n-penten-2-yloxy, n-penten-3-yloxy, n-penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, n-hex-1-en-1-yloxy, n-hex-2-en-1-yloxy, n-hex-3-en-1-yloxy, n-hex-4-en-1-yloxy, n-hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trim, 2-eprop-2-en-1-yloxy, 1-ethyl-1-methylprop-2-en-1-yloxy, 1-ethyl-2-methylprop-1-en-1-yloxy or 1-ethyl-2-methylprop-2-en-1-yloxy, in particular prop-2-en-1-yloxy;

$C_2$–$C_6$-alkenyloxy: ethenyloxy or one of the radicals mentioned under $C_3$–$C_6$-alkenyloxy, in particular ethenyloxy or prop-2 -en-1 -yloxy;

$C_3$–$C_6$-haloalkenyloxy: $C_3$–$C_6$-alkenyloxy as mentioned above which is partially or fully substituted by fluorine, chlorine and/or bromine, ie. for example 2-chloroallyloxy, 3-chloroallyloxy, 2,3-dichloroallyloxy, 3,3-dichloroallyloxy, 2,3,3-trichloroallyloxy, 2,3-dichlorobut-2-enyloxy, 2-bromoallyloxy, 3-bromoallyloxy, 2,3-dibromoallyloxy, 3,3-dibromoallyloxy, 2,3,3-tribromoallyloxy or 2,3-dibromobut-2-enyloxy, in particular 2-chloroallyloxy or 3,3-dichloroallyloxy;

$C_3$–$C_6$-alkenylthio: prop-1-en-1-ylthio, prop-2-en-1-ylthio, 1-methylethenylthio, n-buten-1-ylthio, n-buten-2-ylthio, n-buten-3-ylthio, 1-methylprop-1-en-1-ylthio, 2-methylprop-1-en-1-ylthio, 1-methylprop-2-en-1-ylthio, 2-methylprop-2-en-1-ylthio, n-penten-1-ylthio, n-penten-2-ylthio, n-penten-3-ylthio, n-penten-4-ylthio, 1-methylbut-1-en-1-ylthio, 2-methylbut-1-en-1-ylthio, 3-methylbut-1-en-1-ylthio, 1-methylbut-2-en-1-ylthio, 2-methylbut-2-en-1-ylthio, 3-methylbut-2-en-1-ylthio, 1-methylbut-3-en-1-ylthio, 2-methylbut-3-en-1-ylthio, 3-methylbut-3-en-1-ylthio, 1,1-dimethylprop-2-en-1-ylthio, 1,2-dimethylprop-1-en-1-ylthio, 1,2-dimethylprop-2-en-1-ylthio, 1-ethylprop-1-en-2-ylthio, 1-ethylprop-2-en-1-ylthio, n-hex-1-en-1-ylthio, n-hex-2-en-1-ylthio, n-hex-3-en-1-ylthio, n-hex-4-en-1-ylthio, n-hex-5-en-1-ylthio, 1-methylpent-1-en-1-ylthio, 2-methylpent-1-en-1-ylthio, 3-methylpent-1-en-1-ylthio, 4-methylpent-1-en-1-ylthio, 1-methylpent-2-en-1-ylthio, 2-methylpent-2-en-1-ylthio, 3-methylpent-2-en-1-ylthio, 4-methylpent-2-en-1-ylthio, 1-methylpent-3-en-1-ylthio, 2-methylpent-3-en-1-ylthio, 3-methylpent-3-en-1-ylthio, 4-methylpent-3-en-1-ylthio, 1-methylpent-4-en-1-ylthio, 2-methylpent-4-en-1-ylthio, 3-methylpent-4-en-1-ylthio, 4-methylpent-4-en-1-ylthio, 1,1-dimethylbut-2-en-1-ylthio, 1,1-dimethylbut-3-en-1-ylthio, 1,2-dimethylbut-1-en-1-ylthio, 1,2-dimethylbut-2-en-1-ylthio, 1,2-dimethylbut-3-en-1-ylthio, 1,3-dimethylbut-1-en-1-ylthio, 1,3-dimethylbut-2-en-1-ylthio, 1,3-dimethylbut-3-en-1-ylthio, 2,2-dimethylbut-3-en-1-ylthio, 2,3-dimethylbut-1-en-1-ylthio, 2,3-dimethylbut-2-en-1-ylthio, 2,3-dimethylbut-3-en-1-ylthio, 3,3-dimethylbut-1-en-1-ylthio, 3,3-dimethylbut-2-en-1-ylthio, 1-ethylbut-1-en-1-ylthio, 1-ethylbut-2-en-1-ylthio, 1-ethylbut-3-en-1-ylthio, 2-ethylbut-1-en-1-ylthio, 2-ethylbut-2-en-1-ylthio, 2-ethylbut-3-en-1-ylthio, 1,1,2-trimethylprop-2-en-1-ylthio, 1-ethyl-1-methylprop-2-en-1-ylthio, 1-ethyl-2-methylprop-1-en-1-ylthio or 1-ethyl-2-methylprop-2-en-1-ylthio, in particular prop-2-en-1-ylthio;

$C_2$–$C_6$-alkenylthio: ethenylthio or one of the radicals mentioned under $C_3$–$C_6$-alkenylthio, in particular ethenylthio or prop-2-en-1-ylthio;

C₃–C₆-alkynyl: prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, in particular prop-2-yn-1-yl;

C₂–C₆-alkynyl: ethynyl or one of the radicals mentioned under C₃–C₆-alkynyl, in particular ethynyl or prop-2-yn-1-yl;

C₃–C₆-alkynyloxy: prop-1-yn-1-yloxy, prop-2-yn-1-yloxy, n-but-1-yn-1-yloxy, n-but-1-yn-3-yloxy, n-but-1-yn-4-yloxy, n-but-2-yn-1-yloxy, n-pent-1-yn-1-yloxy, n-pent-1-yn-3-yloxy, n-pent-1-yn-4-yloxy, n-pent-1-yn-5-yloxy, n-pent-2-yn-1-yloxy, n-pent-2-yn-4-yloxy, n-pent-2-yn-5-yloxy, 3-methylbut-1-yn-3-yloxy, 3-methylbut-1-yn-4-yloxy, n-hex-1-yn-1-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yloxy, n-hex-2-yn-6-yloxy, n-hex-3-yn-1-yloxy, n-hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy or 4-methylpent-2-yn-5-yloxy, in particular prop-2-yn-1-yloxy;

C₂–C₆-alkynyloxy: ethynyloxy or one of the radicals mentioned under C₃–C₆-alkynyloxy, in particular ethynyloxy or prop-2-yn-1-yloxy;

C₃–C₆-alkynylthio: prop-1-yn-1-ylthio, prop-2-yn-1-ylthio, n-but-1-yn-1-ylthio, n-but-1-yn-3-ylthio, n-but-1-yn-4-ylthio, n-but-2-yn-1-ylthio, n-pent-1-yn-1-ylthio, n-pent-1-yn-3-ylthio, n-pent-1-yn-4-ylthio, n-pent-1-yn-5-ylthio, n-pent-2-yn-1-ylthio, n-pent-2-yn-4-ylthio, n-pent-2-yn-5-ylthio, 3-methylbut-1-yn-3-ylthio, 3-methylbut-1-yn-4-ylthio, n-hex-1-yn-1-ylthio, n-hex-1-yn-3-ylthio, n-hex-1-yn-4-ylthio, n-hex-1-yn-5-ylthio, n-hex-1-yn-6-ylthio, n-hex-2-yn-1-ylthio, n-hex-2-yn-4-ylthio, n-hex-2-yn-5-ylthio, n-hex-2-yn-6-ylthio, n-hex-3-yn-1-ylthio, n-hex-3-yn-2-ylthio, 3-methylpent-1-yn-1-ylthio, 3-methylpent-1-yn-3-ylthio, 3-methylpent-1-yn-4-ylthio, 3-methylpent-1-yn-5-ylthio, 4-methylpent-1-yn-1-ylthio, 4-methylpent-2-yn-4-ylthio or 4-methylpent-2-yn-5-ylthio, in particular prop-2-yn-1-ylthio;

C₂–C₆-alkynylthio: ethynylthio or one of the radicals mentioned under C₃–C₆-alkynylthio, in particular ethynylthio or prop-2-yn-1-ylthio;

(C₃–C₆-alkenyl)oxycarbonyl: prop-1-en-1-yloxycarbonyl, prop-2-en-1-yloxycarbonyl, 1-methylethenyloxycarbonyl, n-buten-1-yloxycarbonyl, n-buten-2-yloxycarbonyl, n-buten-3-yloxycarbonyl, 1-methylprop-1-en-1-yloxycarbonyl, 2-methylprop-1-en-1-yloxycarbonyl, 1-methylprop-2-en-1-yloxycarbonyl, 2-methylprop-2-en-1-yloxycarbonyl, n-penten-1-yloxycarbonyl, n-penten-2-yloxycarbonyl, n-penten-3-yloxycarbonyl, n-penten-4-yloxycarbonyl, 1-methylbut-1-en-1-yloxycarbonyl, 2-methylbut-1-en-1-yloxycarbonyl, 3-methylbut-1-en-1-yloxycarbonyl, 1-methylbut-2-en-1-yloxycarbonyl, 2-methylbut-2-en-1-yloxycarbonyl, 3-methylbut-2-en-1-yloxycarbonyl, 1-methylbut-3-en-1-yloxycarbonyl, 2-methylbut-3-en-1-yloxycarbonyl, 3-methylbut-3-en-1-yloxycarbonyl, 1,1-dimethylprop-2-en-1-yloxycarbonyl, 1,2-dimethylprop-1-en-1-yloxycarbonyl, 1,2-dimethylprop-2-en-1-yloxycarbonyl, 1-ethylprop-1-en-2-yloxycarbonyl, 1-ethylprop-2-en-1-yloxycarbonyl, n-hex-1-en-1-yloxycarbonyl, n-hex-2-en-1-yloxycarbonyl, n-hex-3-en-1-yloxycarbonyl, n-hex-4-en-1-yloxycarbonyl, n-hex-5-en-1-yloxycarbonyl, 1-methylpent-1-en-1-yloxycarbonyl, 2-methylpent-1-en-1-yloxycarbonyl, 3-methylpent-1-en-1-yloxycarbonyl, 4-methylpent-1-en-1-yloxycarbonyl, 1-methylpent-2-en-1-yloxycarbonyl, 2-methylpent-2-en-1-yloxycarbonyl, 3-methylpent-2-en-1-yloxycarbonyl, 4-methylpent-2-en-1-yloxycarbonyl, 1-methylpent-3-en-1-yloxycarbonyl, 2-methylpent-3-en-1-yloxycarbonyl, 3-methylpent-3-en-1-yloxycarbonyl, 4-methylpent-3-en-1-yloxycarbonyl, 1-methylpent-4-en-1-yloxycarbonyl, 2-methylpent-4-en-1-yloxycarbonyl, 3-methylpent-4-en-1-yloxycarbonyl, 4-methylpent-4-en-1-yloxycarbonyl, 1,1-dimethylbut-2-en-1-yloxycarbonyl, 1,1-dimethylbut-3-en-1-yloxycarbonyl, 1,2-dimethylbut-1-en-1-yloxycarbonyl, 1,2-dimethylbut-2-en-1-yloxycarbonyl, 1,2-dimethylbut-3-en-1-yloxycarbonyl, 1,3-dimethylbut-1-en-1-yloxycarbonyl, 1,3-dimethylbut-2-en-1-yloxycarbonyl, 1,3-dimethylbut-3-en-1-yloxycarbonyl, 2,2-dimethylbut-3-en-1-yloxycarbonyl, 2,3-dimethylbut-1-en-1-yloxycarbonyl, 2,3-dimethylbut-2-en-1-yloxycarbonyl, 2,3-dimethylbut-3-en-1-yloxycarbonyl, 3,3-dimethylbut-1-en-1-yloxycarbonyl, 3,3-dimethylbut-2-en-1-yloxycarbonyl, 1-tethylbut-1-en-1-yloxycarbonyl, 1-ethylbut-2-en-1-yloxycarbonyl, 1-ethylbut-3-en-1-yloxycarbonyl, 2-ethylbut-1-en-1-yloxycarbonyl, 2-ethylbut-2-en-1-yloxycarbonyl, 2-ethylbut-3-en-1-yloxycarbonyl, 1,1,2-trimethylprop-2-en-1-yloxycarbonyl, 1-ethyl-1-methylprop-2-en-1-yloxycarbonyl, 1-ethyl-2-methylprop-1-en-1-yloxycarbonyl or 1-ethyl-2-methylprop-2-en-1-yloxycarbonyl, in particular prop-2-en-1-yloxycarbonyl;

(C₃–C₆-alkenyloxy)carbonyl-C₁–C₆-alkyl: C₁–C₆-alkyl which is substituted by (C₃–C₆-alkenyloxy)carbonyl as mentioned above, preferably by prop-2-en-1-yloxycarbonyl, ie. for example prop-2-en-1-yloxycarbonylmethyl;

(C₃–C₆-alkenyl)carbonyloxy: prop-1-en-1-ylcarbonyloxy, prop-2-en-1-ylcarbonyloxy, 1-methylethenylcarbonyloxy, n-buten-1-ylcarbonyloxy, n-buten-2-ylcarbonyloxy, n-buten-3-ylcarbonyloxy, 1-methylprop-1-en-1-ylcarbonyloxy, 2-methylprop-1-en-1-ylcarbonyloxy, 1-methylprop-2-en-1-ylcarbonyloxy, 2-methylprop-2-en-1-ylcarbonyloxy, n-penten-1-ylcarbonyloxy, n-penten-2-ylcarbonyloxy, n-penten-3-ylcarbonyloxy, n-penten-4-ylcarbonyloxy, 1-methylbut-1-en-1-ylcarbonyloxy, 2-methylbut-1-en-1-ylcarbonyloxy, 3-methylbut-1-en-1-ylcarbonyloxy, 1-methylbut-2-en-1-ylcarbonyloxy, 2-methylbut-2-en-1-ylcarbonyloxy, 3-methylbut-2-en-1-ylcarbonyloxy, 1-methylbut-3-en-1-ylcarbonyloxy, 2-methylbut-3-en-1-ylcarbonyloxy, 3-methylbut-3-en-1-ylcarbonyloxy, 1,1-dimethylprop-2-en-1-ylcarbonyloxy, 1,2-dimethylprop-1-en-1-ylcarbonyloxy, 1,2-dimethylprop-2-en-1-ylcarbonyloxy, 1-ethylprop-1-en-2-ylcarbonyloxy, 1-ethylprop-2-en-1-ylcarbonyloxy, n-hex-1-en-1-ylcarbonyloxy, n-hex-2-en-1-ylcarbonyloxy, n-hex-3-en-1-ylcarbonyloxy, n-hex-4-en-1-ylcarbonyloxy, n-hex-5-en-1-ylcarbonyloxy, 1-methylpent-1-en-1-ylcarbonyloxy, 2-methylpent-1-en-1-ylcarbonyloxy, 3-methylpent-1-en-1-ylcarbonyloxy, 4-methylpent-1-en-1-ylcarbonyloxy, 1-methylpent-2-en-1-ylcarbonyloxy, 2-methylpent-2-en-1-ylcarbonyloxy, 3-methylpent-2-en-1-ylcarbonyloxy, 4-methylpent-2-en-1-ylcarbonyloxy, 1-methylpent-3-en-1-ylcarbonyloxy, 2-methylpent-3-en-1-ylcarbonyloxy, 3-methylpent-3-en-1-ylcarbonyloxy, 4-methylpent-3-en-1-ylcarbonyloxy, 1-methylpent-4-en-1-ylcarbonyloxy, 2-methylpent-4-en-1-ylcarbonyloxy, 3-methylpent-4-en-1-ylcarbonyloxy, 4-methylpent-4-en-1-ylcarbonyloxy, 1,1-dimethylbut-2-en-1-ylcarbonyloxy, 1,1-dimethylbut-3-en-1-ylcarbonyloxy, 1,2-dimethylbut-1-en-1-ylcarbonyloxy, 1,2-dimethylbut-2-en-1-ylcarbonyloxy, 1,2-dimethylbut-3-en-1-ylcarbonyloxy, 1,3-dimethylbut-1-en-1-ylcarbonyloxy, 1,3-dimethylbut-2-en-1-ylcarbonyloxy, 1,3-dimethylbut-3-en-1-ylcarbonyloxy, 2,2-dimethylbut-3-en-1-ylcarbonyloxy, 2,3-dimethylbut-1-en-1-ylcarbonyloxy, 2,3-dimethylbut-2-en-1-ylcarbonyloxy, 2,3-dimethylbut-3-en-1-ylcarbonyloxy, 3,3-dimethylbut-1-en-1-ylcarbonyloxy, 3,3-dimethylbut-2-en-1-ylcarbonyloxy, 1-ethylbut-1-en-1-ylcarbonyloxy, 1-ethylbut-2-en-1-ylcarbonyloxy, 1-ethylbut-3-en-1-ylcarbonyloxy, 2-ethylbut-1-en-1-ylcarbonyloxy, 2-ethylbut-2-en-1-ylcarbonyloxy, 2-ethylbut-3-en-1-ylcarbonyloxy, 1,1,2-trimethylprop-2-en-1-ylcarbonyloxy, 1-ethyl-1-methylprop-2-en-1-ylcarbonyloxy, 1-ethyl-2-methylprop-1-en-1-ylcarbonyloxy or 1-ethyl-2-methylprop-2-en-1-ylcarbonyloxy, in particular prop-2-en-1-ylcarbonyloxy;

($C_2$–$C_6$-alkenyl)carbonyloxy: ethenylcarbonyloxy or one of the radicals mentioned under ($C_3$–$C_6$-alkenyl) carbonyloxy, in particular ethenylcarbonyloxy or prop-2-en-1-ylcarbonyloxy;

($C_3$–$C_6$-alkenyl)carbonylthio: prop-1-en-1-ylcarbonylthio, prop-2-en-1-ylcarbonylthio, 1-methylethenylcarbonylthio, n-buten-1-ylcarbonylthio, n-buten-2-ylcarbonylthio, n-buten-3-ylcarbonylthio, 1-methylprop-1-en-1-ylcarbonylthio, 2-methylprop-1-en-1-ylcarbonylthio, 1-methylprop-2-en-1-ylcarbonylthio, 2-methylprop-2-en-1-ylcarbonylthio, n-penten-1-ylcarbonylthio, n-penten-2-ylcarbonylthio, n-penten-3-ylcarbonylthio, n-penten-4-ylcarbonylthio, 1-methylbut-1-en-1-ylcarbonylthio, 2-methylbut-1-en-1-ylcarbonylthio, 3-methylbut-1-en-1-ylcarbonylthio, 1-methylbut-2-en-1-ylcarbonylthio, 2-methylbut-2-en-1-ylcarbonylthio, 3-methylbut-2-en-1-ylcarbonylthio, 1-methylbut-3-en-1-ylcarbonylthio, 2-methylbut-3-en-1-ylcarbonylthio, 3-methylbut-3-en-1-ylcarbonylthio, 1,1-dimethylprop-2-en-1-ylcarbonylthio, 1,2-dimethylprop-1-en-1-ylcarbonylthio, 1,2-dimethylprop-2-en-1-ylcarbonylthio, 1-ethylprop-1-en-2-ylcarbonylthio, 1-ethylprop-2-en-1-ylcarbonylthio, n-hex-1-en-1-ylcarbonylthio, n-hex-2-en-1-ylcarbonylthio, n-hex-3-en-1-ylcarbonylthio, n-hex-4-en-1-ylcarbonylthio, n-hex-5-en-1-ylcarbonylthio, 1-methylpent-1-en-1-ylcarbonylthio, 2-methylpent-1-en-1-ylcarbonylthio, 3-methylpent-1-en-1-ylcarbonylthio, 4-methylpent-1-en-1-ylcarbonylthio, 1-methylpent-2-en-1-ylcarbonylthio, 2-methylpent-2-en-1-ylcarbonylthio, 3-methylpent-2-en-1-ylcarbonylthio, 4-methylpent-2-en-1-ylcarbonylthio, 1-methylpent-3-en-1-ylcarbonylthio, 2-methylpent-3-en-1-ylcarbonylthio, 3-methylpent-3-en-1-ylcarbonylthio, 4-methylpent-3-en-1-ylcarbonylthio, 1-methylpent-4-en-1-ylcarbonylthio, 2-methylpent-4-en-1-ylcarbonylthio, 3-methylpent-4-en-1-ylcarbonylthio, 4-methylpent-4-en-1-ylcarbonylthio, 1,1-dimethylbut-2-en-1-ylcarbonylthio, 1,1-dimethylbut-3-en-1-ylcarbonylthio, 1,2-dimethylbut-2-en-1-ylcarbonylthio, 1,2-dimethylbut-2-en-1-ylcarbonylthio, 1,2-dimethylbut-1-en-1-ylcarbonylthio, 1,3-dimethylbut-1-en-1-ylcarbonylthio, 1,3-dimethylbut-2-en-1-ylcarbonylthio, 1,3-dimethylbut-3-en-1-ylcarbonylthio, 2,3-dimethylbut-3-en-1-ylcarbonylthio, 2,3-dimethylbut-2-en-1-ylcarbonylthio, 2,3-dimethylbut-3-en-1-ylcarbonylthio, 2,3-dimethylbut-1-en-1-ylcarbonylthio, 3,3-dimethylbut-2-en-1-ylcarbonylthio, 3,3-dimethylbut-1-en-1-ylcarbonylthio, 1-ethylbut-2-en-1-ylcarbonylthio, 1-ethylbut-3-en-1-ylcarbonylthio, 1-ethylbut-3-en-1-ylcarbonylthio, 2-ethylbut-2-en-1-ylcarbonylthio, 2-ethylbut-3-en-1-ylcarbonylthio, 2-ethylbut-3-en-1-ylcarbonylthio, 1,1,2-trimethylprop-2-en-1-ylcarbonylthio, 1-ethyl-1-methylprop-2-en-1-ylcarbonylthio, 1-ethyl-2-methylprop-1-en-1-ylcarbonylthio or 1-ethyl-2-methylprop-2-en-1-ylcarbonylthio, in particular prop-2-en-1-ylcarbonylthio;

($C_2$–$C_6$-alkenyl)carbonylthio: ethenylcarbonylthio or one of the radicals mentioned under ($C_3$–$C_6$-alkenyl) carbonylthio, in particular prop-2-en-1-ylcarbonylthio;

($C_3$–$C_6$-alkynyl)carbonyloxy: prop-1-yn-1-ylcarbonyloxy, prop-2-yn-1-ylcarbonyloxy, n-but-1-yn-1-ylcarbonyloxy, n-but-1-yn-3-ylcarbonyloxy, n-but-1-yn-4-ylcarbonyloxy, n-but-2-yn-1-ylcarbonyloxy, n-pent-1-yn-1-ylcarbonyloxy, n-pent-1-yn-3-ylcarbonyloxy, n-pent-1-yn-4-ylcarbonyloxy, n-pent-1-yn-5-ylcarbonyloxy, n-pent-2-yn-1-ylcarbonyloxy, n-pent-2-yn-4-ylcarbonyloxy, n-pent-2-yn-5-ylcarbonyloxy, 3-methylbut-1-yn-3-ylcarbonyloxy, 3-methylbut-1-yn-4-ylcarbonyloxy, n-hex-1-yn-1-ylcarbonyloxy, n-hex-1-yn-3-ylcarbonyloxy, n-hex-1-yn-4-ylcarbonyloxy, n-hex-1-yn-5-ylcarbonyloxy, n-hex-1-yn-6-ylcarbonyloxy, n-hex-2-yn-1-ylcarbonyloxy, n-hex-2-yn-4-ylcarbonyloxy, n-hex-2-yn-5-ylcarbonyloxy, n-hex-2-yn-6-ylcarbonyloxy, n-hex-3-yn-1-ylcarbonyloxy, n-hex-3-yn-2-ylcarbonyloxy, 3-methylpent-1-yn-1-ylcarbonyloxy, 3-methylpent-1-yn-3-ylcarbonyloxy, 3-methylpent-1-yn-4-ylcarbonyloxy, 3-methylpent-1-yn-5-ylcarbonyloxy, 4-methylpent-1-yn-1-ylcarbonyloxy, 4-methylpent-2-yn-4-ylcarbonyloxy, or 4-methylpent-2-yn-5-ylcarbonyloxy, in particular prop-2-yn-1-ylcarbonyloxy;

($C_2$–$C_6$-alkynyl)carbonyloxy: ethynylcarbonyloxy or one of the radicals mentioned under ($C_3$–$C_6$-alkynyl) carbonyloxy, in particular ethynylcarbonyloxy or prop-2-yn-1-ylcarbonyloxy;

$C_3$–$C_6$-alkynylsulfonyloxy: prop-1-yn-1-ylsulfonyloxy, prop-2-yn-1-ylsulfonyloxy, n-but-1-yn-1-ylsulfonyloxy, n-but-1-yn-3-ylsulfonyloxy, n-but-1-yn-4-ylsulfonyloxy, n-but-2-yn-1-ylsulfonyloxy, n-pent-1-yn-1-ylsulfonyloxy, n-pent-1-yn-3-ylsulfonyloxy, n-pent-1-yn-4-ylsulfonyloxy, n-pent-1-yn-5- ylsulfonyloxy, n-pent-2-yn-1-ylsulfonyloxy, n-pent-2-yn-4-ylsulfonyloxy, n-pent-2-yn-5-ylsulfonyloxy, 3-methylbut-1-yn-3-ylsulfonyloxy, 3-methylbut-1-yn-4-ylsulfonyloxy, n-hex-1-yn-1-ylsulfonyloxy, n-hex-1-yn-3-ylsulfonyloxy, n-hex-1-yn-4-ylsulfonyloxy, n-hex-1-yn-5-ylsulfonyloxy, n-hex-1-yn-6-ylsulfonyloxy, n-hex-2-yn-1-ylsulfonyloxy, n-hex-2-yn-4-ylsulfonyloxy, n-hex-2-yn-5-ylsulfonyloxy, n-hex-2-yn-6-ylsulfonyloxy, n-hex-3-yn-1-ylsulfonyloxy, n-hex-3-yn-2-ylsulfonyloxy, 3-methylpent-1-yn-1-ylsulfonyloxy, 3-methylpent-1-yn-3-ylsulfonyloxy, 3-methylpent-1-yn-4-ylsulfonyloxy, 3-methylpent-1-yn-5-ylsulfonyloxy, 4-methylpent-1-yn-1-ylsulfonyloxy, 4-methylpent-2-yn-4-ylsulfonyloxy or 4-methylpent-2-yn-5-ylsulfonyloxy, in particular prop-2-yn-1-ylsulfonyloxy;

($C_3$–$C_6$-alkynyl)carbonylthio: prop-1-yn-1-ylcarbonylthio, prop-2-yn-1-ylcarbonylthio, n-but-1-yn-1-ylcarbonylthio, n-but-1-yn-3-ylcarbonylthio, n-but-1-yn-4-ylcarbonylthio, n-but-2-yn-1-ylcarbonylthio, n-pent-1-yn-1-ylcarbonylthio, n-pent-1-yn-3-ylcarbonylthio, n-pent-1-yn-4-ylcarbonylthio, n-pent-1-yn-5-ylcarbonylthio, n-pent-2-yn-1-ylcarbonylthio, n-pent-2-yn-4-ylcarbonylthio, n-pent-2-yn-5-ylcarbonylthio, 3-methylbut-1-yn-3-ylcarbonylthio, 3-methylbut-1-yn-4-ylcarbonylthio, n-hex-1-yn-1-ylcarbonylthio, n-hex-1-yn-3-ylcarbonylthio, n-hex-1-yn-4-ylcarbonylthio, n-hex-1-yn-5-ylcarbonylthio, n-hex-1-yn-6-ylcarbonylthio, n-hex-2-yn-1-ylcarbonylthio, n-hex-2-yn-4-ylcarbonylthio, n-hex-2-yn-5-ylcarbonylthio, n-hex-2-yn-6-ylcarbonylthio, n-hex-3-yn-1-ylcarbonylthio, n-hex-3-yn-2-ylcarbonylthio, 3-methylpent-1-yn-1-ylcarbonylthio, 3-methylpent-1-yn-3-ylcarbonylthio, 3-methylpent-1-yn-4-ylcarbonylthio, 3-methylpent-1-yn-5-ylcarbonylthio, 4-methylpent-1-yn-1-ylcarbonylthio, 4-methylpent-2-yn-4-ylcarbonylthio or 4-methylpent-2-yn-5-ylcarbonylthio, in particular prop-2-yn-1-ylcarbonylthio;

($C_2$–$C_6$-alkynyl)carbonylthio: ethynylcarbonylthio or one of the radicals mentioned under ($C_3$–$C_6$-alkynyl) carbonylthio, in particular ethynylcarbonylthio or prop-2-yn-1-ylcarbonylthio;

($C_1$–$C_6$-alkoxy)carbonyl-$C_2$–$C_6$-alkenyl: $C_2$–$C_6$-alkenyl which is substituted by ($C_1$–$C_6$-alkoxy)carbonyl as mentioned above, ie. for example methoxycarbonylprop-2-en-1-yl;

$C_3$–$C_6$-alkenyloxy-$C_1$–$C_6$-alkyl: $C_1$–$C_6$-alkyl which is substituted by $C_3$–$C_6$-alkenyloxy as mentioned above, preferably by allyloxy, 2-methylprop-2-en-1-yloxy, but-1-en-3-yloxy, but-1-en-4-yloxy or but-2-en-1-yloxy, ie. for example allyloxymethyl, 2-allyloxyethyl or but-1-en-4-yloxymethyl;

$C_3$–$C_6$-alkynyloxy-$C_1$–$C_6$-alkyl: $C_1$–$C_6$-alkyl which is substituted by $C_3$–$C_6$-alkynyloxy as mentioned above, preferably by propargyloxy, but-1-yn-3-yloxy, but-1-yn-4-yloxy or but-2-yn-1-yloxy, ie. for example propargyloxymethyl or 2-propargyloxyethyl;

$C_3$–$C_7$-cycloalkyl: cyclopropyl, cyclobutyl, cyclopentyl, cyclohexyl or cycloheptyl, in particular cyclopentyl or cyclohexyl;

$C_3$–$C_6$-cycloalkyl: cyclopropyl, cyclobutyl, cyclopentyl or cyclohexyl;

$C_3$–$C_8$-cycloalkyl: cyclopropyl, cyclobutyl, cyclopentyl, cyclohexyl, cycloheptyl or cyclooctyl, in particular cyclopentyl or cyclohexyl;

$C_3$–$C_8$-cycloalkyl-$C_1$–$C_4$-alkyl: cyclopropylmethyl, cyclobutylmethyl, cyclopentylmethyl, cyclohexylmethyl, cycloheptylmethyl, cyclooctylmethyl, 1-(cyclopropyl)ethyl, 1-(cyclobutyl)ethyl, 1-(cyclopentyl)ethyl, 1-(cyclohexyl)ethyl, 1-(cycloheptyl)ethyl, 1-(cyclooctyl)ethyl, 2-(cyclopropyl)ethyl, 2-(cyclobutyl)ethyl, 2-(cyclopentyl)ethyl, 2-(cyclohexyl)ethyl, 2-(cycloheptyl)ethyl, 2-(cyclooctyl)ethyl, 3-(cyclopropyl)propyl, 3-(cyclobutyl)propyl, 3-(cyclopentyl)propyl, 3-(cyclohexyl)propyl, 3-(cycloheptyl)propyl, 3-(cyclooctyl)propyl, 4-(cyclopropyl)butyl, 4-(cyclobutyl)butyl, 4-(cyclopentyl)butyl, 4-(cyclohexyl)butyl, 4-(cycloheptyl)butyl or 4-(cyclooctyl)butyl, in particular cyclopentylmethyl or cyclohexylmethyl;

$C_3$–$C_6$-cycloalkyloxy: cyclopropyloxy, cyclobutyloxy, cyclopentyloxy or cyclohexyloxy;

$C_3$–$C_6$-cycloalkylthio: cyclopropylthio, cyclobutylthio, cyclopentylthio or cyclohexylthio;

$C_3$–$C_6$-cycloalkylcarbonyloxy: cyclopropylcarbonyloxy, cyclobutylcarbonyloxy, cyclopentylcarbonyloxy or cyclohexylcarbonyloxy;

$C_3$–$C_6$-cycloalkylsulfonyloxy: cyclopropylsulfonyloxy, cyclobutylsulfonyloxy, cyclopentylsulfonyloxy or cyclohexylsulfonyloxy;

$C_3$–$C_6$-cycloalkyloxy-$C_1$–$C_4$-alkyl: cyclopropyloxymethyl, cyclobutyloxymethyl, cyclopentyloxymethyl, cyclohexyloxymethyl, 1-cyclopropyloxy)ethyl, 1-(cyclobutyloxy)ethyl, 1-(cyclopentyloxy)ethyl, 1-(cyclohexyloxy)ethyl, 2-(cyclopropyloxy)ethyl, 2-(cyclobutyloxy)ethyl, 2-(cyclopentyloxy)ethyl, 2-(cyclohexyloxy)ethyl, 3-(cyclopropyloxy) propyl, 3-(cyclobutyloxy)propyl, 3-(cyclopentyloxy)propyl, 3-(cyclohexyloxy)propyl, 4-(cyclopropyloxy)butyl, 4-(cyclobutyloxy)butyl, 4-(cyclopentyloxy)butyl or 4-(cyclohexyloxy)butyl, in particular cyclopentyloxymethyl, cyclohexyloxymethyl or 2-(cyclopentyloxy)ethyl;

$C_5$–$C_7$-cycloalkenyloxy: cyclopent-1-enyloxy, cyclopent-2-enyloxy, cyclopent-3-enyloxy, cyclohex-1-enyloxy, cyclohex-2-enyloxy, cyclohex-3-enyloxy, cyclohept-1-enyloxy, cyclohept-2-enyloxy, cyclohept-3-enyloxy or cyclohept-4-enyloxy;

$C_1$–$C_3$-alkylene: methylene, 1,2-ethylene or 1,3-propylene.

3 - to 7-membered heterocyclyl—which may be attached directly or via an oxygen, alkoxy, alkenyloxy or alkynyloxy bridge—is a saturated, partially or fully unsaturated or aromatic heterocycle having one to three hetero atoms selected from a group consisting of one to three nitrogen atoms, one or two oxygen atoms and one or two sulfur atoms.

Examples of saturated heterocycles which may contain a carbonyl or thiocarbonyl ring member are:

oxiranyl, thiiranyl, aziridin-1-yl, aziridin-2-yl, diaziridin-1-yl, diaziridin-3-yl, oxetan-2-yl, oxetan-3-yl, thietan-2-yl, thietan-3-yl, azetidin-1-yl, azetidin-2-yl, azetidin-3-yl, tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3- oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-y, 1,3-dithiepan-2-yl, 1,3-dithiepan-2-yl, 1,3-dithiepan-2-yl, 1,4-dioxepan-2-yl, 1,4-dioxepan-7-yl, hexahydroazepin-1-yl, hexahydroazepin-2-yl, hexahydroazepin-3-yl, hexahydroazepin-4-yl, hexahydro-1,3-diazepin-1-yl , hexahydro-1,3-diazepin-2-yl, hexahydro-1,3-diazepin-4-yl, hexahydro-1,4-diazepin-1-yl and hexahydro-1,4-diazepin-2-yl;

Examples of unsaturated heterocycles which may contain a carbonyl or thiocarbonyl ring member are: dihydrofuran-2-yl, 1,2-oxazolin-3-yl, 1,2-oxazolin-5-yl, 1,3-oxazolin-2-yl.

Preferred heteroaromatics are the 5- and 6-membered heteroaromatics, ie. for example:

furyl, such as 2-furyl and 3-furyl, thienyl, such as 2-thienyl and 3-thienyl, pyrrolyl, such as 2-pyrrolyl and 3-pyrrolyl, isoxazolyl, such as 3-isoxazolyl, 4-isoxazolyl and 5-isoxazolyl, isothiazolyl, such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-oxazolyl, 4-oxazolyl and 5-oxazolyl, thiazolyl, such as 2-thiazolyl, 4-thiazolyl and 5-thiazolyl, imidazolyl, such as 2-imidazolyl and 4-imidazolyl, oxadiazolyl, such as 1,2,4-oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazolyl, such as 1,2,4-triazol-1-yl, 1,2,4-triazol-3-yl and 1,2,4-triazol-4-yl, pyridinyl, such as 2-pyridinyl, 3-pyridinyl and 4-pyridinyl, pyridazinyl, such as 3-pyridazinyl and 4-pyridazinyl, pyrimidinyl, such as 2-pyrimidinyl, 4-pyrimidinyl and 5-pyrimidinyl, and furthermore 2-pyrazinyl, 1,3,5-triazin-2-yl and 1,2,4-triazin-3-yl, in particular pyridyl, pyrimidyl, furanyl and thienyl.

All phenyl and heterocyclic rings are preferably unsubstituted or carry one substituent.

With a view to the use of the compounds of the formula I according to the invention as herbicides, the variables preferably have the following meanings, in each case either on their own or in combination:

X is oxygen;

$R^1$ is cyano, $C_1$–$C_4$-haloalkyl or $C_1$–$C_4$-alkylsulfonyl, in particular $C_1$–$C_4$-haloalkyl, particularly preferably trifluoromethyl;

$R^3$ is hydrogen;

$R^4$ is cyano or halogen, in particular halogen, particularly preferably chlorine;

$R^5$ is hydrogen or halogen, in particular hydrogen, fluorine or chlorine, particularly preferably fluorine;

$R^6$ is hydrogen;

$R^7$ is cyano or halogen, in particular cyano or chlorine, particularly preferably chlorine;

$R^8$ is 1) hydrogen, hydroxyl, mercapto, cyano, nitro, halogen, $C_1$–$C_6$-alkyl, $C_1$–$C_6$-haloalkyl, $C_1$–$C_6$-haloalkoxy, $C_1$–$C_6$-haloalkylthio, $C_1$–$C_6$-alkylthio-$(C_1$–$C_6$-alkyl)carbonyl, $(C_1$–$C_6$-alkyl)iminooxycarbonyl, $C_1$–$C_6$-alkoxy-$C_1$–$C_6$-alkyl, $C_1$–$C_6$-alkoxyamino-$C_1$–$C_6$-alkyl, $C_1$–$C_6$-alkoxy-$C_1$–$C_6$-alkylamino-$C_1$–$C_6$-alkyl, 2) $C_1$–$C_6$-alkoxy, $C_1$–$C_6$-alkylthio, $C_3$–$C_6$-cycloalkoxy, $C_3$–$C_6$-cycloalkylthio, $C_2$–$C_6$-alkenyloxy, $C_2$–$C_6$-alkenylthio, $C_2$–$C_6$-alkynyloxy, $C_2$–$C_6$-alkynylthio, $(C_1$–$C_6$-alkyl)carbonyloxy, $(C_1$–$C_6$-alkyl)carbonylthio, $(C_1$–$C_6$-alkoxy)carboxyloxy, $(C_2$–$C_6$-alkenyl)carbonyloxy, $(C_2$–$C_6$-alkenyl)carbonylthio, $(C_2$–$C_6$-alkynyl)carbonyloxy, $(C_2$–$C_6$-alkynyl)carbonylthio, $C_1$–$C_6$-alkylsulfonyloxy or $C_1$–$C_6$-alkylsulfonyl, where each of the 17 last-mentioned radicals may, if desired, carry one to three substituents, in each case selected from the group consisting of halogen, nitro, cyano, hydroxyl, $C_3$–$C_6$-cycloalkyl, $C_1$–$C_6$-alkoxy, $C_3$–$C_6$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminooxy, oxo, $=$N—OR$^{18}$, the phenyl, phenoxy or phenylsulfonyl group, which may be unsubstituted or may carry one to three substituents, in each case selected from the group consisting of halogen, nitro, cyano, $C_1$–$C_6$-alkyl, $C_1$–$C_6$-haloalkyl, $C_1$–$C_6$-alkoxy and $(C_1$–$C_6$-alkoxy)carbonyl, a group —CO—R$^{19}$, —CO—OR$^{19}$, —CO—SR$^{19}$, —CO—N(R$^{19}$)R$^{20}$, —OCO—R$^{19}$, —OCO—OR$^{19}$, —OCO—SR$^{19}$, —OCO—N(R$^{19}$)R$^{20}$ or —N(R$^{19}$)—R$^{20}$, the group —C(R$^{21}$)=N—OR$^{18}$;

3) —CO—R$^{22}$, —CS—R$^{22}$, —C(NR$^{23}$)—R$^{22}$, —C(R$^{22}$)(Z$^1$R$^{24}$)(Z$^2$R$^{25}$), where Z$^1$ and Z$^2$ are each oxygen or sulfur, —C(R$^{22}$)=C(R$^{26}$)—CN, —C(R$^{22}$)=C(R$^{26}$)—CO—R$^{27}$, —CH(R$^{22}$)—CH(R$^{26}$)—CO—R$^{27}$, —C(R$^{22}$)=C(R$^{26}$)—CH$_2$—CO—R$^{27}$, —C(R$^{22}$)=C(R$^{26}$)—C(R$^{28}$)=C(R$^{29}$)—CO—R$^{27}$, —C(R$^{22}$)=C(R$^{26}$)—CH$_2$—CH(R$^{30}$)—CO—R$^{27}$, —CO—OR$^{31}$, —CO—SR$^{31}$, —CO—N(R$^{31}$)—OR$^{18}$, —C≡C—CO—NH—OR$^{18}$, —C≡C—CO—N(R$^{31}$)—OR$^{18}$, —C≡C—CS—NH—OR$^{18}$, —C≡C—CS—N(R$^{31}$)—OR$^{18}$, —C(R$^{22}$)=C(R$^{26}$)—CO—NH—OR$^{18}$, —C(R$^{22}$)=C(R$^{26}$)—CO—N(R$^{31}$)—OR$^{18}$, —C(R$^{22}$)=C(R$^{26}$)—CS—NH—OR$^{18}$, —C(R$^{22}$)=C(R$^{26}$)—CS—N(R$^{31}$)—OR$^{18}$, —C(R$^{22}$)=C(R$^{26}$)—C(R$^{21}$)=N—OR$^{18}$, —C(R$^{21}$)=N—OR$^{18}$, —C≡C—C(R$^{21}$)=N—OR$^{18}$, —C(Z$^1$R$^{24}$)(Z$^2$R$^{25}$)—OR$^{31}$, —C(Z$^1$R$^{24}$)(Z$^2$R$^{25}$)—SR$^{31}$, —C(Z$^1$R$^{24}$)(Z$^2$R$^{25}$)—N(R$^{32}$)R$^{33}$, —N(R$^{32}$)R$^{33}$ or —CON(R$^{32}$)R$^{33}$;

$R^8$ is in particular —CO—R$^{22}$, —CS—R$^{22}$, —C(NR$^{23}$)—R$^{22}$, —C(R$^{22}$)(Z$^1$R$^{24}$)(Z$^2$R$^{25}$), where Z$^1$ and Z$^2$ are each oxygen or sulfur, —C(R$^{22}$)=C(R$^{26}$)—CN, —C(R$^{22}$)=C(R$^{26}$)—CO—R$^{27}$, —CH(R$^{22}$)—CH(R$^{26}$)—CO—R$^{27}$, —C(R$^{22}$)=C(R$^{26}$)—CH$_2$—CO—R$^{27}$, —C(R$^{22}$)=C(R$^{26}$)—C(R$^{28}$)=C(R$^{29}$)—CO—

$R^{27}$, —C($R^{22}$)=C($R^{26}$)—CH$_2$—CH($R^{30}$)—CO—$R^{27}$, —CO—O$R^{31}$, —CO—S$R^{31}$, —CO—N($R^{31}$)—O$R^{18}$, —C≡C—CO—NH—O$R^{18}$, —C≡C—CO—N($R^{31}$)—O$R^{18}$, —C≡C—CS—NH—O$R^{18}$, —C≡C—CS—N($R^{31}$)—O$R^{18}$, —C($R^{22}$)=C($R^{26}$)—CO—NH—O$R^{18}$, —C($R^{22}$)=C($R^{26}$)—CO—N($R^{31}$)—O$R^{18}$, —C($R^{22}$)=C($R^{26}$)—CS—NH—O$R^{18}$, —C($R^{22}$)=C($R^{26}$)—CS—N($R^{31}$)—O$R^{18}$, —C($R^{22}$)=C($R^{26}$)—C($R^{21}$)=N—O$R^{18}$, —C($R^{21}$)=N—O$R^{18}$, —C≡C—C($R^{21}$)=N—O$R^{18}$, —C($Z^1R^{24}$)($Z^2R^{25}$)—O$R^{31}$, —C($Z^1R^{24}$)($Z^2R^{25}$)—S$R^{31}$, —C($Z^1R^{24}$)($Z^2R^{25}$)—N($R^{32}$)$R^{33}$, —N($R^{32}$)$R^{33}$ or —CON($R^{32}$)$R^{33}$; particularly preferably —CO—$R^{22}$, —C(N$R^{23}$)—$R^{22}$ oder —C($R^{22}$)=C($R^{26}$)—CO—$R^{27}$;

$R^{18}$ is hydrogen, $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, hydroxy-$C_1$–$C_6$-alkyl, $C_1$–$C_6$-alkoxy-$C_1$–$C_6$-alkyl, $C_1$–$C_6$-alkylthio-$C_1$–$C_6$-alkyl, cyano-$C_1$–$C_6$-alkyl, ($C_1$–$C_6$-alkyl)carbonyl-$C_1$–$C_6$-alkyl, ($C_1$–$C_6$-alkoxy)carbonyl-$C_1$–$C_6$-alkyl, ($C_1$–$C_6$-alkoxy)carbonyl-$C_2$–$C_6$-alkenyl, ($C_1$–$C_6$-alkyl)carbonyloxy-$C_1$–$C_6$-alkyl or phenyl-$C_1$–$C_6$-alkyl, where the phenyl ring may, if desired, carry one to three substituents, in each case selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

$R^{19}$ is hydrogen, $C_1$–$C_6$-alkyl, $C_3$–$C_6$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, ($C_3$–$C_6$-alkenyloxy)carbonyl-$C_1$–$C_6$-alkyl, phenyl or phenyl-$C_1$–$C_6$-alkyl, where the phenyl group and the phenyl ring of the phenylalkyl group may be unsubstituted or may carry one to three radicals, in each case selected from the group consisting of halogen, nitro, cyano, $C_1$–$C_6$-alkyl, $C_1$–$C_6$-haloalkyl, $C_1$–$C_6$-alkoxy and ($C_1$–$C_6$-alkyl)carbonyl;

$R^{20}$ is hydrogen, hydroxyl, $C_1$–$C_6$-alkyl, $C_3$–$C_6$-cycloalkyl, $C_1$–$C_6$-alkoxy, ($C_1$–$C_6$-alkoxy)carbonyl-$C_1$–$C_6$-alkoxy, $C_3$–$C_6$-alkenyl or $C_3$–$C_6$-alkenyloxy;

$R^{21}$ is
hydrogen, halogen,
$C_1$–$C_6$-alkyl, $C_1$–$C_6$-haloalkyl, $C_1$–$C_6$-alkoxy, $C_1$–$C_6$-haloalkoxy, $C_3$–$C_6$-alkenyloxy, $C_1$–$C_6$-alkylthio, $C_1$–$C_6$-haloalkylthio, ($C_1$–$C_6$-alkyl)carbonyloxy, ($C_1$–$C_6$-haloalkyl)carbonyloxy, $C_1$–$C_6$-alkylsulfonyloxy or $C_1$–$C_6$-haloalkylsulfonyloxy, where the 11 last-mentioned radicals may carry one of the following substituents: hydroxyl, cyano, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy)carbonyl, ($C_1$–$C_6$-alkyl)aminocarbonyl, di($C_1$–$C_6$-alkyl)aminocarbonyl, ($C_1$–$C_6$-alkyl)carbonyloxy, $C_1$–$C_6$-alkoxy-($C_1$–$C_6$-alkyl)aminocarbonyl;

a 3- to 7-membered azaheterocycle which is attached to the nitrogen atom via a carbonyl bridge and which may, in addition to carbon ring members, also contain one oxygen or sulfur atom as ring member;

($C_1$–$C_6$-alkyl)carbonyl, ($C_1$–$C_6$-haloalkyl)carbonyl, ($C_1$–$C_6$-alkoxy)carbonyl, ($C_1$–$C_6$-alkoxy)carbonyloxy, ($C_1$–$C_6$-alkyl)carbonylthio, ($C_1$–$C_6$-haloalkyl)carbonylthio, ($C_1$–$C_6$-alkoxy)carbonylthio, $C_2$–$C_6$-alkenyl, $C_2$–$C_6$-alkenyloxy, $C_3$–$C_6$-alkynyl, $C_3$–$C_6$-alkynyloxy, $C_3$–$C_6$-alkynylthio, ($C_2$–$C_6$-alkynyl)carbonyloxy, $C_3$–$C_6$-alkynylsulfonyloxy, $C_3$–$C_6$-cycloalkyl, $C_3$–$C_6$-cycloalkyloxy, $C_3$–$C_6$-cycloalkylthio, ($C_3$–$C_6$-cycloalkyl)carbonyloxy, $C_3$–$C_6$-cycloalkylsulfonyloxy;

phenyl, phenoxy, phenylthio, benzoyloxy, phenylsulfonyloxy, phenyl-$C_1$–$C_6$-alkyl, phenyl-$C_1$–$C_6$-alkoxy, phenyl-$C_1$–$C_6$-alkylthio, phenyl-($C_1$–$C_6$-alkyl)carbonyloxy or phenyl-($C_1$–$C_6$-alkyl)sulfonyloxy, where the phenyl rings of the 10 last-mentioned radicals may be unsubstituted or may themselves carry one to three substituents, in each case selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

$R^{22}$ is hydrogen, cyano, $C_1$–$C_6$-alkyl, $C_1$–$C_6$-haloalkyl, $C_2$–$C_6$-alkenyl, $C_2$–$C_6$-alkynyl, $C_3$–$C_6$-cycloalkyl, $C_1$–$C_6$-alkoxy-$C_1$–$C_6$-alkyl or ($C_1$–$C_6$-alkoxy)carbonyl;

$R^{23}$ is hydrogen, hydroxyl, $C_1$–$C_6$-alkyl, $C_3$–$C_6$-alkenyl, $C_3$–$C_6$-alkynyl, $C_3$–$C_7$-cycloalkyl, $C_1$–$C_6$-haloalkyl, $C_1$–$C_6$-alkoxy-$C_1$–$C_6$-alkyl, $C_1$–$C_6$-alkoxy, $C_3$–$C_6$-alkenyloxy, $C_3$–$C_6$-alkynyloxy, $C_3$–$C_6$-cycloalkoxy, $C_5$–$C_7$-cycloalkenyloxy, $C_1$–$C_6$-haloalkoxy, $C_3$–$C_6$-haloalkenyloxy, hydroxy-$C_1$–$C_6$-alkoxy, cyano-$C_1$–$C_6$-alkoxy, $C_3$–$C_6$-cycloalkyl-$C_1$–$C_6$-alkoxy, $C_1$–$C_6$-alkoxy-$C_1$–$C_6$-alkoxy, $C_1$–$C_6$-alkoxy-$C_3$–$C_6$-alkenyloxy, ($C_1$–$C_6$-alkyl)carbonyloxy, ($C_1$–$C_6$-haloalkyl)carbonyloxy, ($C_1$–$C_6$-alkyl)carbamoyloxy, ($C_1$–$C_6$-haloalkyl)carbamoyloxy, ($C_1$–$C_6$-alkyl)carbonyl-$C_1$–$C_6$-alkyl, ($C_1$–$C_6$-alkyl)carbonyl-$C_1$–$C_6$-alkoxy, ($C_1$–$C_6$-alkoxy)carbonyl-$C_1$–$C_6$-alkyl, ($C_1$–$C_6$-alkoxy)carbonyl-$C_1$–$C_6$-alkoxy, $C_1$–$C_6$-alkylthio-$C_1$–$C_6$-alkoxy, di($C_1$–$C_6$-alkyl)amino-$C_1$–$C_6$-alkoxy, phenyl which may itself carry one to three substituents, in each case selected from the group consisting of cyano, nitro, halogen, $C_1$–$C_6$-alkyl, $C_1$–$C_6$-haloalkyl, $C_2$–$C_6$-alkenyl, $C_1$–$C_6$-alkoxy and ($C_1$–$C_6$-alkoxy)carbonyl, phenyl-$C_1$–$C_6$-alkoxy, phenyl-$C_3$–$C_6$-alkenyloxy or phenyl-$C_3$–$C_6$-alkynyloxy, where in each case one or two methylene groups of the hydrocarbon chains may be replaced by —O—, —S— or —N($C_1$–$C_6$-alkyl)-, and where each phenyl ring may be unsubstituted or may itself carry one to three substituents, in each case selected from the group consisting of cyano, nitro, halogen, $C_1$–$C_6$-alkyl, $C_1$–$C_6$-haloalkyl, $C_2$–$C_6$-alkenyl, $C_1$–$C_6$-alkoxy and ($C_1$–$C_6$-alkoxy)carbonyl, heterocyclyl, heterocyclyl-$C_1$–$C_6$-alkoxy, heterocyclyl-$C_3$–$C_6$-alkenyloxy or heterocyclyl-$C_3$–$C_6$-alkynyloxy, where in each case one or two methylene groups of the hydrocarbon chains may be replaced by —O—, —S— or —N($C_1$–$C_6$-alkyl)-, and where each heterocycle may be 3- to 7-membered, saturated, unsaturated or aromatic and contains one to four hetero atoms selected from the group consisting of two oxygen atoms, two sulfur atoms and 4 nitrogen atoms, and is either unsubstituted or itself carries one to three substituents, in each case selected from the group consisting of cyano, nitro, halogen, $C_1$–$C_6$-alkyl, $C_1$–$C_6$-haloalkyl, $C_2$–$C_6$-alkenyl, $C_1$–$C_6$-alkoxy and ($C_1$–$C_6$-alkoxy)carbonyl, or —N($R^{35}$)$R^{36}$ where $R^{35}$ and $R^{36}$ are each hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, $C_1$–$C_6$-alkoxy-$C_1$–$C_6$-alkyl, ($C_1$–$C_6$-alkyl)carbonyl, ($C_1$–$C_6$-alkoxy)carbonyl, ($C_1$–$C_6$-alkoxy)carbonyl-$C_1$–$C_6$-alkyl, ($C_1$–$C_6$-alkoxy)carbonyl-$C_2$–$C_6$-alkenyl where the alkenyl chain may additionally carry one to three halogen and/or cyano radicals, or are phenyl which may be unsubstituted or may itself carry one to three substituents, in each case selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl, or where $R^{35}$ and $R^{36}$ together with the linking nitrogen atom form a saturated or unsaturated 4- to 7-membered azaheterocycle which, in addition to carbon ring members, may, if desired, also contain one of the following members: —O—, —S—, —N=, —NH— or —N($C_1$–$C_6$-alkyl)-;

$R^{24}$ and $R^{25}$ independently of one another are each $C_1$–$C_6$-alkyl, $C_1$–$C_6$-haloalkyl, $C_3$–$C_6$-alkenyl, $C_3$–$C_6$-alkynyl, $C_1$–$C_6$-alkoxy-$C_1$–$C_6$-alkyl or together are a saturated or unsaturated 2- to 4-membered hydrocarbon chain which may carry an oxo substituent, where one member of this chain may be replaced by a bridge —O—, —S—, —N=, —NH— or —N($C_1$–$C_6$-alkyl)- which is not adjacent to the variables $Z^1$ and $Z^2$, and where the hydrocarbon chain may carry one to three radicals, in each case selected from the group consisting of cyano, nitro, amino, halogen, $C_1$–$C_6$-alkyl, $C_2$–$C_6$-alkenyl, $C_1$–$C_6$-alkoxy, $C_2$–$C_6$-alkenyloxy, $C_2$–$C_6$-alkynyloxy, $C_1$–$C_6$-haloalkyl, cyano-$C_1$–$C_6$-alkyl, hydroxy-$C_1$–$C_6$-alkyl, $C_1$–$C_6$-alkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_3$–$C_6$-cycloalkyl, $C_3$–$C_6$-cycloalkoxy, carboxyl, ($C_1$–$C_6$-alkoxy)carbonyl, ($C_1$–$C_6$-alkyl)carbonyloxy-$C_1$–$C_6$-alkyl and phenyl which may itself be unsubstituted or may carry one to three substituents, in each case selected from the group consisting of cyano, nitro, amino, halogen, $C_1$–$C_6$-alkyl, $C_1$–$C_6$-haloalkyl, $C_1$–$C_6$-alkoxy and ($C_1$–$C_6$-alkoxy)carbonyl, and where the hydrocarbon chain may also be substituted by a fused-on or spiro-linked 3- to 7-membered ring which may contain as ring members one or two hetero atoms selected from the group consisting of oxygen, sulfur, nitrogen and $C_1$–$C_6$-alkyl-substituted nitrogen, and which may, if desired, itself carry one or two of the following substituents: cyano, $C_1$–$C_6$-alkyl, $C_2$–$C_6$-alkenyl, $C_1$–$C_6$-alkoxy, cyano-$C_1$–$C_6$-alkyl, $C_1$–$C_6$-haloalkyl and ($C_1$–$C_6$-alkoxy)carbonyl;

$R^{26}$ is hydrogen, cyano, halogen, $C_1$–$C_6$-alkyl, $C_1$–$C_6$-haloalkyl, $C_1$–$C_6$-alkoxy, ($C_1$–$C_6$-alkyl)carbonyl or ($C_1$–$C_6$-alkoxy)carbonyl;

$R^{27}$ is hydrogen, O—$R^{34}$, S—$R^{34}$, $C_1$–$C_6$-alkyl which may carry one or two $C_1$–$C_6$-alkoxy substituents, $C_2$–$C_6$-alkenyl, $C_2$–$C_6$-alkynyl, $C_1$–$C_6$-haloalkyl, $C_3$–$C_6$-cycloalkyl, $C_1$–$C_6$-alkylthio-$C_1$–$C_6$-alkyl, $C_1$–$C_6$-alkyliminooxy, —N($R^{32}$)$R^{33}$ or phenyl which may be unsubstituted or may carry one to three substituents, in each case selected from the group consisting of cyano, nitro, halogen, $C_1$–$C_6$-alkyl, $C_2$–$C_6$-alkenyl, $C_1$–$C_6$-haloalkyl, $C_1$–$C_6$-alkoxy and ($C_1$–$C_6$-alkoxy)carbonyl;

$R^{28}$ is hydrogen, cyano, halogen, $C_1$–$C_6$-alkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkyl)carbonyl, ($C_1$–$C_6$-alkoxy)carbonyl, —N($R^{32}$)$R^{33}$ or phenyl which may itself carry one to three substituents, in each case selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl;

$R^{29}$ is hydrogen, cyano, halogen, $C_1$–$C_6$-alkyl, $C_1$–$C_6$-alkoxy, $C_1$–$C_6$-haloalkyl, ($C_1$–$C_6$-alkyl)carbonyl or ($C_1$–$C_6$-alkoxy)carbonyl;

$R^{30}$ is hydrogen, cyano, $C_1$–$C_6$-alkyl or ($C_1$–$C_6$-alkoxy)carbonyl;

$R^{31}$ and $R^{34}$ independently of one another are each hydrogen, $C_1$–$C_6$-alkyl, $C_1$–$C_6$-haloalkyl, $C_2$–$C_6$-alkenyl or $C_2$–$C_6$-alkynyl, where the 4 last-mentioned groups may in each case carry one or two of the following radicals: cyano, halogen, hydroxyl, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy)carbonyl, ($C_1$–$C_6$-alkyl)carbonyloxy, ($C_3$–$C_6$-alkenyloxy)carbonyl or a 3- to 7-membered azaheterocycle which is attached to the nitrogen atom via a carbonyl bridge and which may, in addition to carbon ring members, also contain one oxygen or sulfur atom as ring member; or are ($C_1$–$C_6$-alkyl)carbonyl, ($C_1$–$C_6$-haloalkyl)carbonyl, ($C_1$–$C_6$-alkoxy)carbonyl, $C_1$–$C_6$-alkylaminocarbonyl, di($C_1$–$C_6$-alkyl)aminocarbonyl, $C_1$–$C_6$-alkyloximino-$C_1$–$C_6$-alkyl, $C_3$–$C_6$-cycloalkyl, phenyl or phenyl-$C_1$–$C_6$-alkyl, where the phenyl rings may be unsubstituted or may themselves carry one to three substituents, in each case selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

$R^{32}$ and $R^{33}$ independently of one another are each hydrogen, $C_1$–$C_6$-alkyl, $C_3$–$C_6$-alkenyl, $C_2$–$C_6$-alkynyl, $C_3$–$C_6$-cycloalkyl, $C_1$–$C_6$-haloalkyl, $C_1$–$C_6$-alkoxy-$C_1$–$C_6$-alkyl, ($C_1$–$C_6$-alkyl)carbonyl, ($C_1$–$C_6$-alkoxy)carbonyl, ($C_1$–$C_6$-alkoxy)carbonyl-$C_1$–$C_6$-alkyl, ($C_1$–$C_6$-alkoxy)carbonyl-$C_2$–$C_6$-alkenyl, where the alkenyl chain may additionally carry one to three halogen and/or cyano radicals, or are $C_1$–$C_6$-alkylsulfonyl, ($C_1$–$C_6$-alkoxy)carbonyl-$C_1$–$C_6$-alkylsulfonyl, phenyl or phenylsulfonyl, where the two phenyl rings may be unsubstituted or may themselves carry one to three substituents, in each case selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl, or $R^{32}$ and $R^{33}$ together with the linking nitrogen atom are a saturated or unsaturated 4- to 7-membered azaheterocycle which, in addition to carbon ring members, may, if desired, contain one of the following members: —O—, —S—, —N=, —NH— or —N($C_1$–$C_6$-alkyl)-.

Very generally, preference is also given to those compounds I where $R^7$ is in position α and $R^8$ is in position β.

Very particular preference is given to the substituted 3-phenylisoxazolines of the formula Ia (= I where X=oxygen; $R^1$=trifluoromethyl; $R^2$, $R^3$, $R^6$=hydrogen; $R^4$=chlorine; $R^5$=fluorine; $R^7$ is in position α; $R^8$ is in position β), in particular the compounds Ia.1 to Ia.160 listed in Table 1 below:

TABLE 1

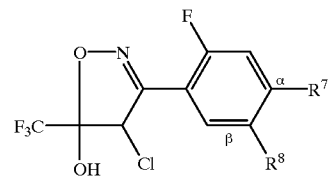

Ia

| No. | $R^7$ | $R^8$ |
|---|---|---|
| Ia.1 | CN | CO—OCH$_3$ |
| Ia.2 | Cl | CO—OCH$_3$ |
| Ia.3 | CN | CO—OC$_2$H$_5$ |
| Ia.4 | Cl | CO—OC$_2$H$_5$ |
| Ia.5 | CN | CO—OCH$_2$—CO—OCH$_3$ |

TABLE 1-continued

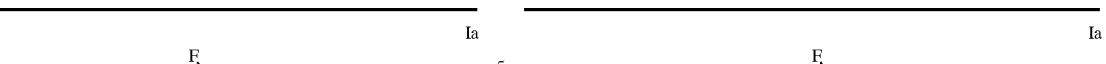

| No. | R⁷ | R⁸ |
|---|---|---|
| Ia.6 | Cl | CO—OCH₂—CO—OCH₃ |
| Ia.7 | CN | CO—OCH₂—CO—OC₂H₅ |
| Ia.8 | Cl | CO—OCH₂—CO—OC₂H₅ |
| Ia.9 | CN | CO—OCH(CH₃)—CO—OCH₃ |
| Ia.10 | Cl | CO—OCH(CH₃)—CO—OCH₃ |
| Ia.11 | CN | CO—OCH(CH₃)—CO—OC₂H₅ |
| Ia.12 | Cl | CO—OCH(CH₃)—CO—OC₂H₅ |
| Ia.13 | CN | CO—OC(CH₃)₂—CO—OCH₃ |
| Ia.14 | Cl | CO—OC(CH₃)₂—CO—OCH₃ |
| Ia.15 | CN | CO—OC(CH₃)₂—CO—OC₂H₅ |
| Ia.16 | Cl | CO—OC(CH₃)₂—CO—OC₂H₅ |
| Ia.17 | CN | CO—OC(CH₃)₂—CO—OCH₂—CH=CH₂ |
| Ia.18 | Cl | CO—OC(CH₃)₂—CO—OCH₂—CH=CH₂ |
| Ia.19 | CN | CO—NH—OCH₃ |
| Ia.20 | Cl | CO—NH—OCH₃ |
| Ia.21 | CN | CO—NH—OCH₂—C₆H₅ |
| Ia.22 | Cl | CO—NH—OCH₂—C₆H₅ |
| Ia.23 | CN | C(N—OCH₃)—OCH₂—CO—OCH₃ |
| Ia.24 | Cl | C(N—OCH₃)—OCH₂—CO—OCH₃ |
| Ia.25 | CN | C(N—OCH₃)—OCH₂—CO—OC₂H₅ |
| Ia.26 | Cl | C(N—OCH₃)—OCH₂—CO—OC₂H₅ |
| Ia.27 | CN | C(N—OCH₂—C₆H₅)—OCH₂—CO—OCH₃ |
| Ia.28 | Cl | C(N—OCH₂—C₆H₅)—OCH₂—CO—OCH₃ |
| Ia.29 | CN | C(N—OCH₂—C₆H₅)—OCH₂—CO—OC₂H₅ |
| Ia.30 | Cl | C(N—OCH₂—C₆H₅)—OCH₂—CO—OC₂H₅ |
| Ia.31 | CN | C(N—OCH₃)—OCH₂—CO—N(CH₃)₂ |
| Ia.32 | Cl | C(N—OCH₃)—OCH₂—CO—N(CH₃)₂ |
| Ia.33 | CN | C(N—OCH₂—C₆H₅)—OCH₂—CO—N(CH₃)₂ |
| Ia.34 | Cl | C(N—OCH₂—C₆H₅)—OCH₂—CO—N(CH₃)₂ |
| Ia.35 | CN | C(N—OCH₃)—OCH₂—CO—N(CH₃)—OCH₃ |
| Ia.36 | Cl | C(N—OCH₃)—OCH₂—CO—N(CH₃)—OCH₃ |
| Ia.37 | CN | C(N—OCH₂—C₆H₅)—OCH₂—CO—N(CH₃)—OCH₃ |
| Ia.38 | Cl | C(N—OCH₂—C₆H₅)—OCH₂—CO—N(CH₃)—OCH₃ |
| Ia.39 | CN | C(N—OCH₃)—OCH(CH₃)—CO—OCH₃ |
| Ia.40 | Cl | C(N—OCH₃)—OCH(CH₃)—CO—OCH₃ |
| Ia.41 | CN | C(N—OCH₃)—OCH(CH₃)—CO—OC₂H₅ |
| Ia.42 | Cl | C(N—OCH₃)—OCH(CH₃)—CO—OC₂H₅ |
| Ia.43 | CN | C(N—OCH₂—C₆H₅)—OCH(CH₃)—CO—OCH₃ |
| Ia.44 | Cl | C(N—OCH₂—C₆H₅)—OCH(CH₃)—CO—OCH₃ |
| Ia.45 | CN | C(N—OCH₂—C₆H₅)—OCH(CH₃)—CO—OC₂H₅ |
| Ia.46 | Cl | C(N—OCH₂—C₆H₅)—OCH(CH₃)—CO—OC₂H₅ |
| Ia.47 | CN | C(N—OCH₃)—OC(CH₃)₂—CO—OCH₃ |
| Ia.48 | Cl | C(N—OCH₃)—OC(CH₃)₂—CO—OCH₃ |
| Ia.49 | CN | C(N—OCH₃)—OC(CH₃)₂—CO—OC₂H₅ |
| Ia.50 | Cl | C(N—OCH₃)—OC(CH₃)₂—CO—OC₂H₅ |
| Ia.51 | CN | C(N—OCH₂—C₆H₅)—OC(CH₃)₂—CO—OCH₃ |
| Ia.52 | Cl | C(N—OCH₂—C₆H₅)—OC(CH₃)₂—CO—OCH₃ |
| Ia.53 | CN | C(N—OCH₂—C₆H₅)—OC(CH₃)₂—CO—OC₂H₅ |
| Ia.54 | Cl | C(N—OCH₂—C₆H₅)—OC(CH₃)₂—CO—OC₂H₅ |
| Ia.55 | CN | CH=N—OCH₃ |
| Ia.56 | Cl | CH=N—OCH₃ |
| Ia.57 | CN | CH=N—OC₂H₅ |
| Ia.58 | Cl | CH=N—OC₂H₅ |
| Ia.59 | CN | CH=N—OCH₂—C₆H₅ |
| Ia.60 | Cl | CH=N—OCH₂—C₆H₅ |
| Ia.61 | CN | CH=N—OCH₂—CO—OCH₃ |
| Ia.62 | Cl | CH=N—OCH₂—CO—OCH₃ |
| Ia.63 | CN | CH=N—OCH(CH₃)—CO—OCH₃ |
| Ia.64 | Cl | CH=N—OCH(CH₃)—CO—OCH₃ |
| Ia.65 | CN | CH₂—N(CH₃)—OCH₃ |
| Ia.66 | Cl | CH₂—N(CH₃)—OCH₃ |
| Ia.67 | CN | CH₂—N(CH₃)—OCH₂—C₆H₅ |
| Ia.68 | Cl | CH₂—N(CH₃)—OCH₂—C₆H₅ |
| Ia.69 | CN | CH=C(Cl)—CO—OCH₃ |
| Ia.70 | Cl | CH=C(Cl)—CO—OCH₃ |
| Ia.71 | CN | CH=C(Cl)—CO—OC₂H₅ |
| Ia.72 | Cl | CH=C(Cl)—CO—OC₂H₅ |
| Ia.73 | CN | CH=C(Cl)—CO—OCH₂—CO—OCH₃ |
| Ia.74 | Cl | CH=C(Cl)—CO—OCH₂—CO—OCH₃ |
| Ia.75 | CN | CH=C(Cl)—CO—OCH₂—CO—OC₂H₅ |
| Ia.76 | Cl | CH=C(Cl)—CO—OCH₂—CO—OC₂H₅ |
| Ia.77 | CN | CH=C(Cl)—CO—OCH(CH₃)—CO—OCH₃ |
| Ia.78 | Cl | CH=C(Cl)—CO—OCH(CH₃)—CO—OCH₃ |
| Ia.79 | CN | CH=C(Cl)—CO—OCH(CH₃)—CO—OC₂H₅ |
| Ia.80 | Cl | CH=C(Cl)—CO—OCH(CH₃)—CO—OC₂H₅ |
| Ia.81 | CN | CH=C(Cl)—CO—N(CH₃)—CH₂—CO—OCH₃ |
| Ia.82 | Cl | CH=C(Cl)—CO—N(CH₃)—CH₂—CO—OCH₃ |
| Ia.83 | CN | CH=C(Cl)—CO—N(CH₃)—CH₂—CO—OC₂H₅ |
| Ia.84 | Cl | CH=C(Cl)—CO—N(CH₃)—CH₂—CO—OC₂H₅ |
| Ia.85 | CN | CH=C(Cl)—CO—NH—CH(CH₃)—CO—OCH₃ |
| Ia.86 | Cl | CH=C(Cl)—CO—NH—CH(CH₃)—CO—OCH₃ |
| Ia.87 | CN | CH=C(Cl)—CO—NH—CH(CH₃)—CO—OC₂H₅ |
| Ia.88 | Cl | CH=C(Cl)—CO—NH—CH(CH₃)—CO—OC₂H₅ |
| Ia.89 | CN | CH=C(Cl)—CO—NH—OCH₃ |
| Ia.90 | Cl | CH=C(Cl)—CO—NH—OCH₃ |
| Ia.91 | CN | CH=C(Cl)—CO—N(OCH₃)—CH₃ |
| Ia.92 | Cl | CH=C(Cl)—CO—N(OCH₃)—CH₃ |
| Ia.93 | CN | CH=C(Cl)—C(N—OCH₃)—OCH₃ |
| Ia.94 | Cl | CH=C(Cl)—C(N—OCH₃)—OCH₃ |
| Ia.95 | CN | CH=C(Cl)—C(N—OCH₃)—OCH₂—CO—OCH₃ |
| Ia.96 | Cl | CH=C(Cl)—C(N—OCH₃)—OCH₂—CO—OCH₃ |
| Ia.97 | CN | CH=C(Cl)—C(N—OCH₃)—OCH₂—CO—OC₂H₅ |
| Ia.98 | Cl | CH=C(Cl)—C(N—OCH₃)—OCH₂—CO—OC₂H₅ |
| Ia.99 | CN | CH=C(Cl)—C(N—OCH₃)—OCH(CH₃)—CO—OCH₃ |
| Ia.100 | Cl | CH=C(Cl)—C(N—OCH₃)—OCH(CH₃)—CO—OCH₃ |
| Ia.101 | CN | CH=C(Cl)—C(N—OCH₃)—OCH(CH₃)—CO—OC₂H₅ |
| Ia.102 | Cl | CH=C(Cl)—C(N—OCH₃)—OCH(CH₃)—CO—OC₂H₅ |
| Ia.103 | CN | CH=C(Cl)—C(N—OCH₃)—OC(CH₃)₂—CO—OCH₃ |
| Ia.104 | Cl | CH=C(Cl)—C(N—OCH₃)—OC(CH₃)₂—CO—OCH₃ |
| Ia.105 | CN | CH=C(Cl)—C(N—OCH₃)—OC(CH₃)₂—CO—OC₂H₅ |
| Ia.106 | Cl | CH=C(Cl)—C(N—OCH₃)—OC(CH₃)₂—CO—OC₂H₅ |
| Ia.107 | CN | OCH₂—C≡CH |
| Ia.108 | Cl | OCH₂—C≡CH |
| Ia.109 | CN | OCH(CH₃)—C≡CH |
| Ia.110 | Cl | OCH(CH₃)—C≡CH |
| Ia.111 | CN | OCH₂—CH=CH₂ |
| Ia.112 | Cl | OCH₂—CH=CH₂ |
| Ia.113 | CN | OCH(CH₃)—CH=CH₂ |
| Ia.114 | Cl | OCH(CH₃)—CH=CH₂ |
| Ia.115 | CN | OCH₂—CO—OCH₃ |
| Ia.116 | Cl | OCH₂—CO—OCH₃ |
| Ia.117 | CN | OCH₂—CO—OC₂H₅ |
| Ia.118 | Cl | OCH₂—CO—OC₂H₅ |
| Ia.119 | CN | OCH₂—CO—OCH₂—CO—OCH₃ |
| Ia.120 | Cl | OCH₂—CO—OCH₂—CO—OCH₃ |
| Ia.121 | CN | OCH₂—CO—OCH₂—CO—OC₂H₅ |
| Ia.122 | Cl | OCH₂—CO—OCH₂—CO—OC₂H₅ |
| Ia.123 | CN | OCH₂—CO—OCH(CH₃)—CO—OCH₃ |
| Ia.124 | Cl | OCH₂—CO—OCH(CH₃)—CO—OCH₃ |
| Ia.125 | CN | OCH₂—CO—OCH(CH₃)—CO—OC₂H₅ |
| Ia.126 | Cl | OCH₂—CO—OCH(CH₃)—CO—OC₂H₅ |
| Ia.127 | CN | OCH₂—CO—OC(CH₃)₂—CO—OCH₃ |
| Ia.128 | Cl | OCH₂—CO—OC(CH₃)₂—CO—OCH₃ |
| Ia.129 | CN | OCH₂—CO—OC(CH₃)₂—CO—OC₂H₅ |
| Ia.130 | Cl | OCH₂—CO—OC(CH₃)₂—CO—OC₂H₅ |
| Ia.131 | CN | OCH₂—CO—OCH₂—CH₂—OCH₃ |
| Ia.132 | Cl | OCH₂—CO—OCH₂—CH₂—OCH₃ |
| Ia.133 | CN | OCH(CH₃)—CO—OCH₃ |
| Ia.134 | Cl | OCH(CH₃)—CO—OCH₃ |
| Ia.135 | CN | OCH(CH₃)—CO—OC₂H₅ |
| Ia.136 | Cl | OCH(CH₃)—CO—OC₂H₅ |
| Ia.137 | CN | OCH(CH₃)—CO—OCH₂—CO—OCH₃ |

TABLE 1-continued

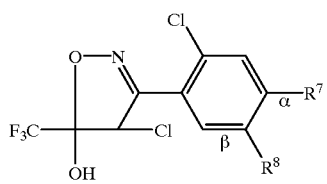

| No. | R⁷ | R⁸ |
|---|---|---|
| Ia.138 | Cl | OCH(CH₃)—CO—OCH₂—CO—OCH₃ |
| Ia.139 | CN | OCH(CH₃)—CO—OCH₂—CO—OC₂H₅ |
| Ia.140 | Cl | OCH(CH₃)—CO—OCH₂—CO—OC₂H₅ |
| Ia.141 | CN | OCH(CH₃)—CO—OCH(CH₃)—CO—OCH₃ |
| Ia.142 | Cl | OCH(CH₃)—CO—OCH(CH₃)—CO—OCH₃ |
| Ia.143 | CN | OCH(CH₃)—CO—OCH(CH₃)—CO—OC₂H₅ |
| Ia.144 | Cl | OCH(CH₃)—CO—OCH(CH₃)—CO—OC₂H₅ |
| Ia.145 | CN | OCH(CH₃)—CO—OCH₂—CH₂—OCH₃ |
| Ia.146 | Cl | OCH(CH₃)—CO—OCH₂—CH₂—OCH₃ |
| Ia.147 | CN | NH—SO₂—CH₃ |
| Ia.148 | Cl | NH—SO₂—CH₃ |
| Ia.149 | CN | NH—SO₂—C₂H₅ |
| Ia.150 | Cl | NH—SO₂—C₂H₅ |
| Ia.151 | CN | NH—SO₂—CH₂—C₆H₅ |
| Ia.152 | Cl | NH—SO₂—CH₂—C₆H₅ |
| Ia.153 | CN | N(CH₃)—SO₂—CH₃ |
| Ia.154 | Cl | N(CH₃)—SO₂—CH₃ |
| Ia.155 | CN | N(C₂H₅)—SO₂—CH₃ |
| Ia.156 | Cl | N(C₂H₅)—SO₂—CH₃ |
| Ia.157 | CN | N(CH₂—C₆H₅)—SO₂—CH₃ |
| Ia.158 | Cl | N(CH₂—C₆H₅)—SO₂—CH₃ |
| Ia.159 | CN | N(SO₂—CH₃)₂ |
| Ia.160 | Cl | N(SO₂—CH₃)₂ |

Furthermore, particular preference is given to the substituted 3-phenylisoxazolines of the formulae Ib and Ic, in particular to
the compounds Ib.1 to Ib.160, which differ from the corresponding compounds Ia.1 to Ia.160 only in that $R^5$ is chlorine:

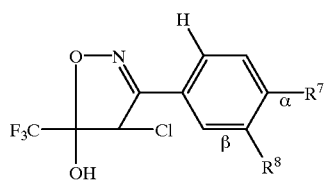

the compounds Ic.1 to Ic.160, which differ from the corresponding compounds Ia.1 to Ia.160 only in that $R^5$ is hydrogen:

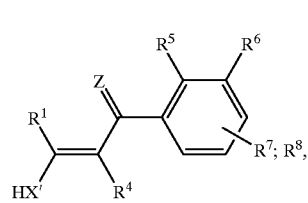

The 3-phenylisoxazolines of the formula I are obtainable in a variety of ways, in particular by one of the following processes:

A) Reaction of a phenyl derivative II with hydroxylamine or one of its salts, for example the hydrochloride or the hydrosulfate {cf. for example M. A. P. Martins et al. in J. Heterocycl. Chem. 32 (1995), 739 and 33 (1996), 1619, and Izv. Akad. Nauk, Ser. Khim. 1996 (5), p. 1306/1307}:

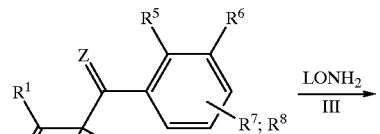

II {X' = oxygen, sulfur or
—N(R⁹)—}

I {X = O, S, —N(R⁹)—;
R² = H}

Z is oxygen, sulfur or —N(R⁹)—;
L is hydrogen or hydroxysulfonyl.
In the case of $R^3$=hydrogen, at least some of the compounds II may be present in the tautomeric form IIa in which case they may also be employed in the form of their salts, in particular of the alkali metal, alkaline earth metal or ammonium salts.

In general, the reaction is carried out in an inert organic solvent/diluent, if desired in the presence of an acid or a base.

Suitable solvent systems are for example those mentioned below:

an organic acid such as acetic acid together with 0.5 to 10 times the molar amount—based on the amount of III—of an alkali metal or ammonium salt of the acid in question, i.e. for example sodium acetate or potassium acetate;

mixtures of water and a lower alcohol such as methanol and ethanol (the mixing ratio being chosen in such a way that the starting materials dissolve) containing a base, for example potassium carbonate, or an acid such as hydrochloric acid;

mixtures of pyridine and a lower alcohol or an aromatic hydrocarbon such as toluene. However, it is also possible to carry out the reaction in pure pyridine.

The reaction is generally carried out at from (−20)°C. to the boiling point of the reaction mixture in question, in particular at from 20° C. to the boiling point of the reaction mixture in question.

The starting materials II (or IIa) and III are usually employed in approximately equimolar amounts, or one of the two components is employed in excess, up to 2 times the molar amount of the other component. Advantageously, the hydroxylamine (salt) is employed in excess.

The process products I where $R^2$=H can be converted in a manner known per se, for example by alkylation or acetylation, into the compound I where $R^2 \neq H$.

B) Reaction of a nitrile oxide of the formula V with a protected enol ether VI {cf. for example Hunig et al., Chem. Ber. 119 (1986), 699–721}:

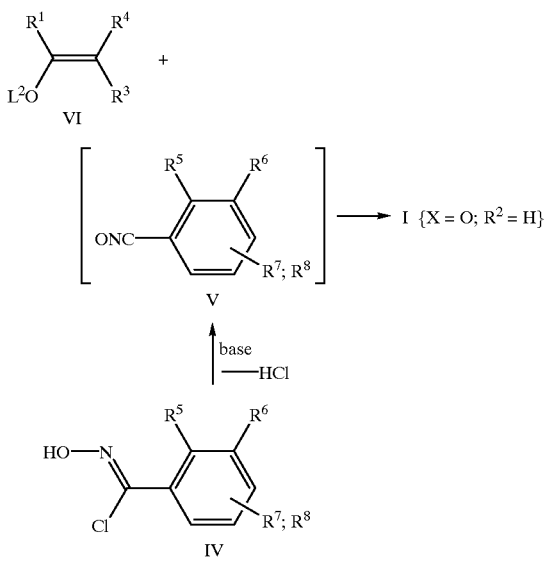

$L^2$ is a customary protecting group for hydroxyl, for example methyl, methylsulfonyl, benzyl or trimethylsilyl.

The nitrile oxides V are preferably prepared from the corresponding hydroxylamine derivatives IV (by elimination of hydrogen chloride using a base) and subsequently reacted directly with VI without prior isolation from the reaction mixture.

Suitable bases are, for example, alkali metal carbonates such as sodium carbonate and potassium carbonate, alkali metal bicarbonates such as potassium bicarbonate, alkali metal hydrides such as sodium hydride, alkali metal and alkaline earth metal hydroxides such as sodium hydroxide, alkali metal alkoxides such as sodium methoxide and potassium tert-butoxide, and amines such as triethylamine and pyridine.

The reaction can be carried out in a single phase in an organic solvent, for example in an aromatic hydrocarbon such as toluene, a halogenated hydrocarbon such as methylene chloride, an ester such as ethyl acetate, an ether such as diethyl ether and tetrahydrofuran, a ketone such as acetone or a lower alcohol such as ethanol. Mixtures of ketone and water or alcohol and water can also be employed.

However, in particular when using an alkali metal hydroxide as base, it is advantageous to carry out the reaction in a two-phase solvent mixture of water and a solvent that is only poorly miscible with water, if at all, for example an aromatic hydrocarbon such as toluene, an ester such as ethyl acetate or an ether such as diethyl ether.

The amount of base is of minor importance.

For the preparation of IV see, for example, Liu et al., J. Org. Chem. 45 (1980), 3916–3918.

Unless stated otherwise, all of the processes described above are advantageously carried out at atmospheric pressure or under the autogenous pressure of the reaction mixture in question.

Work-up of the reaction mixtures is usually carried out by methods known per se, for example by diluting the reaction solution with water and subsequently isolating the product by filtration, crystallization or solvent extraction, or by removing the solvent, partitioning the residue in a mixture of water and a suitable organic solvent and work-up of the organic phase to afford the product.

The 3-phenylisoxazolines I are usually preparable by one of the abovementioned synthesis processes. However, for economical or technical reasons it may be more advantageous to prepare some of the compounds I from similar 3-phenylisoxazolines which differ in particular in the meaning of the radicals $R^7$ and/or $R^8$, employing a procedure known per se, for example ester hydrolysis, esterification, amidation, acetalization, acetyl hydrolysis, a condensation reaction, a Wittig-reaction, Peterson-olefination, etherification, alkylation, oxidation or reduction.

The substituted 3-phenylisoxazolines I may be obtained as isomer mixtures in the preparation. If desired, these mixtures can be separated into the pure isomers using the customary methods for this purpose, such as crystallization or chromatography, including chromatography over an optically active adsorbate. Pure optically active isomers can be advantageously prepared, for example, from suitable optically active starting materials.

Agriculturally useful salts of the compounds I can be formed by reaction with a base of the appropriate cation, preferably an alkali metal hydroxide or alkali metal hydride, or by reaction with an acid of the appropriate anion, preferably hydrochloric acid, hydrobromic acid, sulfuric acid, phosphoric acid or nitric acid.

Salts of I, where the metal ion is not an alkali metal ion, can also be prepared by cation exchange of the corresponding alkali metal salt in a conventional manner, similarly ammonium, phosphonium, sulfonium and sulfoxonium salts by means of ammonia, phosphonium, sulfonium or sulfoxonium hydroxides.

The compounds I and their agriculturally useful salts are suitable, both in the form of isomer mixtures and in the form of the pure isomers, as herbicides. The herbicidal compositions comprising I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds I, or herbicidal compositions comprising them, can additionally be employed in a further number of crop plants for eliminating undesired plants. Examples of suitable crops are the following: *Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N.rustica*), *Olea europaea, oryza sativa, Phaseolus lunatus, Phaseolus vulgaris, Picea abies,*

*Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (s. *vulgare*), *Theobroma cacao, Trifolium pratense, Triticum aestivum, Triticum durum, Vicia faba, Vitis vinifera* and *Zea mays*.

In addition, the compounds I may also be used in crops which tolerate the action of herbicides owing to breeding, including genetic engineering methods.

The compounds I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for scattering, or granules, by means of spraying, atomizing, dusting, scattering or watering. The use forms depend on the intended uses; in any case, they should guarantee the finest possible distribution of the active ingredients according to the invention.

Suitable as inert auxiliaries are essentially the following: mineral oil fractions of medium to high boiling point, such as kerosene and diesel oil, furthermore coal tar oils and oils of vegetable or animal origin, aliphatic, cyclic and aromatic hydrocarbons, eg. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substituted 3-phenylisoxazolines I, either as such or dissolved in an oil or solvent, can be homogenized in water by means of a wetting agent, tackifier, dispersant or emulsifier. Alternatively, it is possible to prepare concentrates comprising active ingredient, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, ligninsulfite waste liquors or methylcellulose.

Powders, materials for scattering and dusts can be prepared by mixing or grinding the active ingredients together with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise approximately from 0.001 to 98% by weight, preferably 0.01 to 95% by weight, of at least one active compound. The active compounds are employed in a purity of from 90% to 100%, preferably 95% to 100% (according to NMR spectrum).

The following formulation examples illustrate the preparation of such preparations:

I. 20 parts by weight of the compound No. 3 are dissolved in a mixture composed of 80 parts by weight of alkylated benzene, 10 parts by weight of the adduct of from 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II. 20 parts by weight of the compound No. 4 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. 12 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. 13 are mixed thoroughly with 3 parts by weight of sodium diisobutylnaphthalene-$\alpha$-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V. 3 parts by weight of the active ingredient No. 14 are mixed with 97 parts by weight of finely divided kaolin. This gives a dust which comprises 3% by weight of the active ingredient.

VI. 20 parts by weight of the active ingredient No. 16 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. 17 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 12 is dissolved in a mixture composed of 80 parts by weight of cyclohexanone and 20 parts by weight of Wettol® EM 31 (=nonionic emulsifier based on ethoxylated castor oil; BASF AG). This gives a stable emulsion concentrate.

The active ingredients I or the herbicidal compositions can be applied pre- or post-emergence. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesired plants growing underneath, or the bare soil surface (post-directed, lay-by).

The rates of application of active ingredient I are from 0.001 to 3.0, preferably 0.01 to 1.0, kg/ha of active substance (a.s.), depending on the control target, the season, the target plants and the growth stage.

To widen the spectrum of action and to achieve synergistic effects, the substituted 3-phenylisoxazolines I may be mixed with a large number of representatives of other herbicidal or growth-regulating active ingredients and then applied concomitantly. Suitable components for mixtures are, for example, 1,2,4-thiadiazoles, 1,3,4-thiadiazoles, amides, aminophosphoric acid and its derivatives, aminotriazoles, anilides, (het) aryloxyalkanoic acids and their derivatives, benzoic acid and its derivatives, benzothiadiazinones, 2-(hetaroyl/ aroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

PREPARATION EXAMPLES

Example 1 (Compound No. 1)

4-Chloro-3-(4'-chloro-2',5'-difluorophenyl)-5-hydroxy-5-trifluoromethylisoxazoline 20.93 g of hydroxylamine-O-sulfonic acid, 55 g of sodium bicarbonate and 21 g of sodium hydrosulfide hydrate were added in succession to 50 g of 2-chloro-1-(4'-chloro-2',5'-difluorophenyl)-4,4,4-trifluorobuta-1,3-dione in 300 ml of ethanol and 80 ml of water. The reaction mixture was stirred for 17 hours and then concentrated under reduced pressure. The residue was taken up in 200 ml of water and 200 ml of ethyl acetate. The resulting mixture was subsequently mixed with 50 ml of dilute hydrochloric acid. The organic phase was then separated off, dried over sodium sulfate and finally concentrated. The oily crude product was purified by silica gel column chromatography (eluent: toluene/cyclohexane=1:1). Yield: 16 g.

Intermediate 1.1

1-(4'-Chloro-2',5'-difluorophenyl)-4,4,4-trifluorobuta-1,3-dione

At 5° C., 21.5 g of a 30% strength by weight solution of sodium methoxide in methanol was added dropwise to a mixture of 22.5 g of 2,5-difluoro-4-chloroacetophenone, 15.17 g of methyl trifluoroacetate and 200 ml of diethyl ether. The reaction mixture was stirred at about 20° C. for 17 hours, and the pH was then adjusted to 3 by the addition of 10% strength hydrochloric acid. The organic phase was subsequently separated off, dried over sodium sulfate and finally concentrated under reduced pressure. The crude product was purified by stirring with petroleum ether and filtering off the undissolved product of value. Yield: 22 g; m.p.: 61–63° C.

Intermediate 1.2

2-Chloro-1-(4'-chloro-2',5'-difluorophenyl)-4,4,4-trifluorobuta-1,3-dione

At about 20° C., 6 ml of sulfuryl chloride were added dropwise to 18 g of 1-(4'-chloro-2',5'-difluorophenyl)-4,4,4-trifluorobuta-1,3-dione in 200 ml of trichloromethane. The mixture was subsequently initially stirred for 17 hours without heating and then for a further 2 hours at 40° C. The low-boiling components were finally distilled off. Yield: 22 g; oil.

Example 2 (Compound No. 2)

4-Chloro-3-(4'-chloro-2',5'-difluorophenyl)-5-(methylcarbonyloxy)-5-trifluoromethylisoxazoline One drop of concentrated sulfuric acid was added to 3.2 g of 4-chloro-3-(4'-chloro-2',5'-difluorophenyl)-5-hydroxy-5-trifluoromethylisoxazoline in 45 ml of acetic anhydride. The mixture was subsequently briefly heated to 160° C. After cooling, the reaction mixture was then concentrated under reduced pressure. The oily crude product was purified by silica gel chromatography (eluent: methylene chloride). Yield: 2.5 g; oil.

Example 3 (Compound No. 3)

4-Chloro-3-(4'-chloro-2'-fluoro-5'-methylphenyl)-5-hydroxy-5-trifluoromethylisoxazoline 30.7 g of sodium acetate and 26 g of hydroxylamine hydrochloride were added to 107.8 g of 2-chloro-1-(4'-chloro-2'-fluoro-5'-methylphenyl-4,4,4-trifluorobuta-1,3-dione in 300 ml of glacial acetic acid, and the mixture was then stirred at about 20° C. for 17 hours. The mixture was then concentrated and the residue was taken up in 500 ml of ethyl acetate. The organic phase was washed with 200 ml of water, dried over sodium sulfate and finally concentrated. For purification, the crude product was stirred with petroleum ether. The solid components were separated off. Yield: 34 g; m.p.: 90–91° C. Chromatographic separation of the filtrate over silica gel (eluent:toluene/dichloromethane=1:1) gave a further 32 g of the product of value. Total yield: 66 g.

Intermediate 3.1

4-Chloro-2-fluoro-5-methylacetophenone

At 60° C., 157 g of acetyl chloride were added dropwise to a mixture of 250 g of 2-chloro-4-fluorotoluene and 267 g of aluminum chloride. The reaction mixture was stirred at 120° C. for 2 hours and then, while still at 100° C., poured onto 2 l of an ice/water mixture. 180 ml of concentrated hydrochloric acid were subsequently stirred into the resulting mixture. The product was then extracted using three times 200 ml of dichloromethane. The organic phase was then washed with 200 ml of water, dried over sodium sulfate and finally concentrated. Yield: 290 g; oil.

Intermediate 3.2

2-Chloro-1-(4'-chloro-2'-fluoro-5'-methylphenyl-4,4,4-trifluorobuta-1,3-dione 33 ml of sulfuryl chloride were added dropwise to 96.1 g of 1-(4'-chloro-2'-fluoro-5'-methylphenyl)-4,4,4-trifluorobuta-1,3-dione (prepared similarly to intermediate 1.1) in 300 ml of dichloromethane. The mixture was subsequently stirred at about 20° C. for 17 hours. The reaction mixture was then concentrated under reduced pressure. Yield: 108 g; oil.

Example 4 (Compound No. 4)

4-Chloro-3-(5'-carboxyl-4'-chloro-2'-fluorophenyl)-5-hydroxy-5-trifluoromethylisoxazoline 2.2 g of sodium dichromate dihydrate were added to 1.7 g of 4-chloro-3-(4'-chloro-2'-fluoro-5'-methylphenyl)-5-hydroxy-5-trifluoromethylisoxazoline in 25 ml of concentrated sulfuric acid whereupon the reaction temperature rose to 40° C. The mixture was subsequently stirred for a further 5 hours at about 20° C., and a further 0.6 g of sodium dichromate dihydrate was added. Stirring was then continued for a further 14 hours at about 20° C., and the reaction mixture was then poured into 100 ml of ice-water. The product was extracted from the aqueous phase using 100 ml of methylene chloride. The organic phase was washed with 100 ml of water, dried over sodium sulfate and finally concentrated. Yield: 1.2 g; oil.

Example 5 (Compound No. 5)

4-Chloro-3-(4'-chloro-2'-fluoro-5'-methylphenyl)-5-(methylcarbonyloxy)-5-trifluoromethylisoxazoline A solution of 0.64 g of 4-chloro-3-(5'-carboxyl-4'-chloro-2'-fluorophenyl)-5-hydroxy-5-trifluoromethylisoxazoline in 25 ml of acetic anhydride was initially stirred for 18 hours at 60° C., and then for a further 3 hours at 120° C. The solvent was subsequently distilled off, giving an oily residue from which the product of value crystallized out. The crystals were filtered off and washed with petroleum ether. Yield: 400 mg.

Example 6 (Compound No. 7)

3-(4'-Chlorophenyl)-4-chloro-5-hydroxy-5-trifluoromethylisoxazoline

At 0° C., 0.87 g of hydroxylamine-O-sulfonic acid was added to a mixture of 2.2 g of 2-chloro-1-(4'-chlorophenyl)-4,4,4-trifluorobuta-1,3-dione, 10 ml of methanol and 10 ml of water. The reaction mixture was stirred for 17 hours, and initially 2 g of sodium bicarbonate and then 0.5 g of sodium hydrosulfide were added. Byproducts were precipitated by the addition of 50 ml of water and then separated off. The solution that remained was admixed with 10 ml of dilute hydrochloric acid. The product was subsequently extracted using 100 ml of ethyl acetate. The organic phase was washed with 50 ml of water, dried over sodium sulfate and finally concentrated. For purification, the crude product was stirred with a mixture of diethyl ether and cyclohexane (1:1). The resulting light-yellow solid was separated off. Yield: 0.84 g; m.p.: 126–127° C.

Intermediate 6.1

1-(4'-Chlorophenyl)-4,4,4-trifluorobuta-1,3-dione

At 5° C., 107.8 g of a 30% strength by weight solution of sodium methoxide in methanol were added dropwise to a mixture of 92 g of 4-chloroacetophenone, 800 ml of diethyl ether and 77 g of methyl trifluoroacetate. The reaction mixture was stirred at about 20° C. for 17 hours and the pH was then adjusted to 3 by the addition of 10% strength hydrochloric acid. The organic phase was subsequently separated off, dried over sodium sulfate and finally concentrated under reduced pressure. The crude product was purified by stirring with petroleum ether and filtering off the undissolved fraction. Yield: 105 g; m.p.: 56–57° C.

Intermediate 6.2

2-Chloro-1-(4'-chlorophenyl)-4,4,4-trifluorobuta-1,3-dione 0.86 ml of sulfuryl chloride was added to 2.5 g of 1-(4'-chlorophenyl)-4,4,4-trifluorobuta-1,3-dione in 15 ml of trichloromethane. The reaction mixture was stirred for 3 hours and then concentrated under reduced pressure. Yield: 2.8 g; oil.

Example 7 (Compound No. 8)

4-Chloro-3-(4'-chloro-3'-nitrophenyl)-5-hydroxy-5-trifluoromethyl isoxazoline

At 5° C., 1.81 ml of a mixture of 0.46 ml of 98% strength nitric acid and 1.35 ml of concentrated sulfuric acid were added dropwise to 2.4 g of 3-(4'-chlorophenyl)-4-chloro-5-hydroxy-5-trifluoromethylisoxazoline in 20 ml of concentrated sulfuric acid. The reaction mixture was stirred at 5° C. for 1.5 hours and then poured into 300 ml of ice-water. The organic phase was subsequently separated off, dried over sodium sulfate and finally concentrated. Yield: 2.5 g.

In addition to the physical data of the compounds I described above, further 3-phenylisoxazolines according to the invention which were also prepared or are preparable by one of the processes described are listed in Table 2 below:

TABLE 2

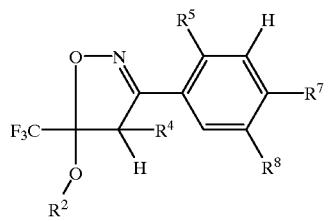

I  {X = O; R$^1$ = CF$_3$; R$^3$, R$^6$ = H;
   R$^7$ in position α;
   R$^8$ in position β}

| No. | R$^2$ | R$^4$ | R$^5$ | R$^7$ | R$^8$ | physical data |
|---|---|---|---|---|---|---|
| 1 | H | Cl | F | Cl | F | oil |
| 2 | CO—CH$_3$ | Cl | F | Cl | F | oil |
| 3 | H | Cl | F | Cl | CH$_3$ | 95–97° C. |
| 4 | H | Cl | F | Cl | COOH | oil |
| 5 | CO—CH$_3$ | Cl | F | Cl | CH$_3$ | crystalline |
| 6 | H | Cl | H | Cl | NO$_2$ | oil |
| 7 | H | Cl | H | Cl | H | 126–127° C. |
| 8 | H | Cl | F | Cl | CO—NH—OCH$_2$C$_6$H$_5$ | 71–75° C. |
| 9 | H | Cl | F | F | H | oil |
| 10 | H | Cl | H | Cl | CH$_3$ | oil |
| 11 | H | Cl | F | Cl | CH$_2$Cl | oil |
| 12 | H | Cl | F | Cl | CO—OC$_2$H$_5$ | oil |
| 13 | H | Cl | F | Cl | CHO | oil |
| 14 | H | Cl | F | Cl | CO—OCH$_3$ | 88–90° C. |
| 15 | H | Cl | F | Cl | CO—OCH(CH$_3$)$_2$ | oil |
| 16 | H | Cl | F | Cl | CO—OCH(CH$_3$)CO—OCH$_3$ | oil |
| 17 | H | Cl | F | Cl | OCH$_3$ | oil |
| 18 | CO—C$_2$H$_5$ | Cl | F | Cl | CO—OC$_2$H$_5$ | oil |
| 19 | H | Cl | F | Cl | CO—NH—OCH$_3$ | oil |
| 20 | H | Cl | Cl | Cl | CH$_3$ | 92–93° C. |
| 21 | H | Cl | Cl | Cl | CH$_2$Cl | oil |
| 22 | H | Cl | Cl | Cl | CHO | 130–131° C. |
| 23 | CO—CH$_3$ | Cl | F | Cl | CO—OC$_2$H$_5$ | oil |
| 24 | CO—CH(CH$_3$)$_2$ | Cl | F | Cl | CO—OC$_2$H$_5$ | oil |
| 25 | H | Cl | Cl | Cl | CO—OCH$_3$ | oil |
| 26 | H | Cl | Cl | Cl | CH=C(Cl)CO—OC$_2$H$_5$ | oil |
| 27 | H | Cl | Cl | Cl | CO—OC$_2$H$_5$ | oil |
| 28 | H | Cl | Cl | Cl | CH$_2$OH | 103–105° C. |
| 29 | H | Cl | Cl | Cl | CH=N—OCH$_3$ | 97–99° C. |
| 30 | H | Cl | Cl | Cl | CH=N—OC$_2$H$_5$ | 78–82° C. |

Use Examples

The herbicidal activity of the substituted 3-phenylisoxazolines I was demonstrated by the following greenhouse experiments:

The culture containers used were plastic flowerpots containing loamy sand with approximately 3.0% of humus as the substrate. The seeds of the test plants were sown separately for each species.

In the pre-emergence treatment, the active compounds, which had been suspended or emulsified in water, were applied directly after sowing by means of finely distributing nozzles. The containers were irrigated gently to promote germination and growth and subequently covered with transparent plastic hoods until the plants had rooted. This cover causes uniform germination of the test plants, unless this was adversely affected by the active compounds.

For the post-emergence treatment, the test plants were first grown to a height of 3 to 15 cm, depending on the growth habit, and only then treated with the active compounds which had been suspended or emulsified in water. For this purpose, the test plants were either sown directly and grown in the same containers, or they were first grown separately as seedlings and transplanted into the test containers a few days prior to the treatment. The rate of application for the post-emergence treatment was 31.2 or 15.6 g/ha of a.s. (active substance).

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the above-ground parts, and 0 means no damage, or normal course of growth.

The plants used in the greenhouse experiments were of the following species:

| Scientific name | Common name |
|---|---|
| *Galium aparine* | catchweed bedstraw |
| *Ipomoea species* | morning glory |
| *Setaria faberii* | giant foxtail |
| *Sinapis alba* | white mustard |
| *Solanum nigrum* | black nightshade |

At application rates of 31.2 and 15.6 g/ha of a.s., compound no. 12 showed very good herbicidal activity against the abovementioned harmful grasses or broad-leaved plants when applied by the post-emergence method.

What is claimed is:

1. A substituted 3-phenylisoxazoline of the formula I

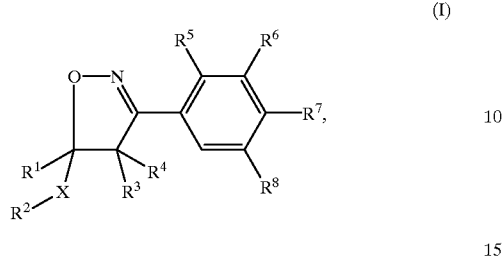

where:

X is oxygen, sulfur or —N($R^9$)—;

$R^1$ is $C_1$–$C_4$-haloalkyl;

$R^2$ is hydrogen, $C_1$–$C_6$-alkyl, ($C_1$–$C_6$-alkyl)carbonyl, $C_1$–$C_6$-alkylsulfonyl, $C_2$–$C_6$-alkenyl, ($C_2$–$C_6$-alkenyl)carbonyl, $C_2$–$C_6$-alkynyl or ($C_2$–$C_6$-alkynyl)carbonyl, where the 7 last-mentioned radicals may, optionally, carry 1 to 3 radicals, in each case selected from the group consisting of halogen, $C_1$–$C_6$-alkoxy, $C_1$–$C_6$-alkylamino, di($C_1$–$C_6$-alkyl)amino, $C_1$–$C_6$-alkoxyimino, phenyl, CO—$OR^{10}$ and CO—N($R^{11}$)—$R^{12}$;

$R^3$ is hydrogen;

$R^4$ is halogen;

$R^5$ is hydrogen or halogen;

$R^6$ is hydrogen;

$R^7$ is cyano or halogen;

$R^8$ is 1) hydrogen, hydroxyl, mercapto, cyano, nitro, halogen, $C_1$–$C_6$-alkyl, $C_1$–$C_6$-haloalkyl, $C_1$–$C_6$-haloalkoxy, $C_1$–$C_6$-haloalkylthio, $C_1$–$C_6$-alkylthio-($C_1$–$C_6$-alkyl)carbonyl, ($C_1$–$C_6$-alkyl)iminooxycarbonyl, $C_1$–$C_6$-alkoxy-$C_1$–$C_6$-alkyl, $C_1$–$C_6$-alkoxyamino-$C_1$–$C_6$-alkyl, $C_1$–$C_6$-alkoxy-$C_1$–$C_6$-alkylamino-$C_1$–$C_6$-alkyl, 2) $C_1$–$C_6$-alkoxy, $C_1$–$C_6$-alkylthio, $C_3$–$C_6$-cycloalkoxy, $C_3$–$C_6$-cycloalkylthio, $C_2$–$C_6$-alkenyloxy, $C_2$–$C_6$-alkenylthio, $C_2$–$C_6$-alkynyloxy, $C_2$–$C_6$-alkynylthio, ($C_1$–$C_6$-alkyl)carbonyloxy, ($C_1$–$C_6$-alkyl)carbonylthio, ($C_1$–$C_6$-alkoxy)carboxyloxy, ($C_2$–$C_6$-alkenyl)carbonyloxy, ($C_2$–$C_6$-alkenyl)carbonylthio, ($C_2$–$C_6$-alkynyl)carbonyloxy, ($C_2$–$C_6$-alkynyl)carbonylthio, $C_1$–$C_6$-alkylsulfonyloxy or $C_1$–$C_6$-alkylsulfonyl, where each of the 17 last-mentioned radicals may, optionally, carry one to three substituents, in each case selected from the group consisting of halogen, nitro, cyano, hydroxyl, $C_3$–$C_6$-cycloalkyl, $C_1$–$C_6$-alkoxy, $C_3$–$C_6$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminooxy, oxo, =N—$OR^{18}$, the phenyl, phenoxy or phenylsulfonyl group, which may be unsubstituted or may carry one to three substituents, in each case selected from the group consisting of halogen, nitro, cyano, $C_1$–$C_6$-alkyl, $C_1$–$C_6$-haloalkyl, $C_1$–$C_6$-alkoxy and ($C_1$–$C_6$-alkoxy)carbonyl, a group —CO—$R^{19}$, —CO—$OR^{19}$, —CO—$SR^{19}$, —CO—N($R^{19}$)$R^{20}$, —OCO—$R^{19}$, —OCO—$OR^{19}$, —OCO—$SR^{19}$, —OCO—N($R^{19}$)$R^{20}$ or —N($R^{19}$)—$R^{20}$, 3) —CO—$R^{22}$, —CS—$R^{22}$, —C(N$R^{23}$)—$R^{22}$, —C($R^{22}$)($Z^1R^{24}$)($Z^2R^{25}$), where $Z^1$ and $Z^2$ are each oxygen or sulfur, —C($R^{22}$)=C($R^{26}$)—CN, —C($R^{22}$)=C($R^{26}$)—CO—$R^{27}$, —CH($R^{22}$)—CH($R^{26}$)—CO—$R^{27}$, —C($R^{22}$)=C($R^{26}$)—$CH_2$—CO—$R^{27}$, —C($R^{22}$)=C($R^{26}$)—C($R^{28}$)=C($R^{29}$)—CO—$R^{27}$, —C($R^{22}$)=C($R^{26}$)—$CH_2$—CH($R^{30}$)—CO—$R^{27}$, —CO—$OR^{31}$, —CO—$SR^{31}$, —CO—N($R^{31}$)—$OR^{18}$, —C≡C—CO—N($R^{31}$)—$OR^{18}$, —C≡C—CS—N($R^{31}$)—$OR^{18}$, —C($R^{22}$)=C($R^{26}$)—CO—N($R^{31}$)—$OR^{18}$, —C($R^{22}$)=C($R^{26}$)—CS—N($R^{31}$)—$OR^{18}$, —C($R^{22}$)=C($R^{26}$)—C($R^{21}$)=N—$OR^{18}$, —C($R^{21}$)=N—$OR^{18}$, —C≡C—C($R^{21}$)=N—$OR^{18}$, —C($Z^1R^{24}$)($Z^2R^{25}$)—$OR^{31}$, —C($Z^1R^{24}$)($Z^2R^{25}$)—$SR^{31}$, —C($Z^1R^{24}$)($Z^2R^{25}$)—N($R^{32}$)$R^{33}$, —N($R^{32}$)$R^{33}$ or —CON($R^{32}$)$R^{33}$;

$R^9$, $R^{10}$ and $R^{12}$ independently of one another are each hydrogen, $C_1$–$C_6$-alkyl, $C_3$–$C_6$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, ($C_3$–$C_6$-alkenyloxy)carbonyl-$C_1$–$C_6$-alkyl, phenyl or phenyl-$C_1$–$C_6$-alkyl, where the phenyl group and the phenyl ring of the phenylalkyl group may be unsubstituted or may carry one to three radicals, in each case selected from the group consisting of halogen, nitro, cyano, $C_1$–$C_6$-alkyl, $C_1$–$C_6$-haloalkyl, $C_1$–$C_6$-alkoxy and ($C_1$–$C_6$-alkyl)carbonyl;

$R^{11}$ is hydrogen, hydroxyl, $C_1$–$C_6$-alkyl, $C_3$–$C_6$-cycloalkyl, $C_1$–$C_6$-alkoxy, ($C_1$–$C_6$-alkoxy)carbonyl-$C_1$–$C_6$-alkoxy, $C_3$–$C_6$-alkenyl or $C_3$–$C_6$-alkenyloxy;

$R^{22}$ is hydrogen, cyano, $C_1$–$C_6$-alkyl, $C_1$–$C_6$-haloalkyl, $C_2$–$C_6$-alkenyl, $C_2$–$C_6$-alkynyl, $C_3$–$C_6$-cycloalkyl, $C_1$–$C_6$-alkoxy-$C_1$–$C_6$-alkyl or ($C_1$–$C_6$-alkoxy)carbonyl;

$R^{23}$ is hydrogen, hydroxyl, $C_1$–$C_6$-alkyl, $C_3$–$C_6$-alkenyl, $C_3$–$C_6$-alkynyl, $C_3$–$C_7$-cycloalkyl, $C_1$–$C_6$-haloalkyl, $C_1$–$C_6$-alkoxy-$C_1$–$C_6$-alkyl, $C_1$–$C_6$-alkoxy, $C_3$–$C_6$-alkenyloxy, $C_3$–$C_6$-alkynyloxy, $C_3$–$C_6$-cycloalkoxy, $C_5$–$C_7$-cycloalkenyloxy, $C_1$–$C_6$-haloalkoxy, $C_3$–$C_6$-haloalkenyloxy, hydroxy-$C_1$–$C_6$-alkoxy, cyano-$C_1$–$C_6$-alkoxy, $C_3$–$C_6$-cycloalkyl-$C_1$–$C_6$-alkoxy, $C_1$–$C_6$-alkoxy-$C_1$–$C_6$-alkoxy, $C_1$–$C_6$-alkoxy-$C_3$–$C_6$-alkenyloxy, ($C_1$–$C_6$-alkyl)carbonyloxy, ($C_1$–$C_6$-haloalkyl)carbonyloxy, ($C_1$–$C_6$-alkyl)carbamoyloxy, ($C_1$–$C_6$-haloalkyl)carbamoyloxy, ($C_1$–$C_6$-alkyl)carbonyl-$C_1$–$C_6$-alkyl, ($C_1$–$C_6$-alkyl)carbonyl-$C_1$–$C_6$-alkoxy, ($C_1$–$C_6$-alkoxy)carbonyl-$C_1$–$C_6$-alkyl, ($C_1$–$C_6$-alkoxy)carbonyl-$C_1$–$C_6$-alkoxy, $C_1$–$C_6$-alkylthio-$C_1$–$C_6$-alkoxy, di($C_1$–$C_6$-alkyl)amino-$C_1$–$C_6$-alkoxy, phenyl which may itself carry one to three substituents, in each case selected from the group consisting of cyano, nitro, halogen, $C_1$–$C_6$-alkyl, $C_1$–$C_6$-haloalkyl, $C_2$–$C_6$-alkenyl, $C_1$–$C_6$-alkoxy and ($C_1$–$C_6$-alkoxy)carbonyl, phenyl-$C_1$–$C_6$-alkoxy, phenyl-$C_3$–$C_6$-alkenyloxy or phenyl-$C_3$–$C_6$-alkynyloxy, where in each case one or two methylene groups of the hydrocarbon chains may be replaced by —O—, —S— or —N($C_1$–$C_6$-alkyl)-, and where each phenyl ring may be unsubstituted or may carry one to three substituents, in each case selected from the group consisting of cyano, nitro, halogen, $C_1$–$C_6$-alkyl, $C_1$–$C_6$-haloalkyl, $C_2$–$C_6$-alkenyl, $C_1$–$C_6$-alkoxy and ($C_1$–$C_6$-alkoxy)carbonyl, heterocyclyl, heterocyclyl-$C_1$–$C_6$-alkoxy, heterocyclyl-$C_3$–$C_6$-alkenyloxy or heterocyclyl-$C_3$–$C_6$-alkynyloxy, where in each case one or two methylene groups of the hydrocarbon chains may be replaced by —O—, —S— or —N($C_1$–$C_6$-alkyl)-, and where each heterocycle may have 3 to 7 members and may be saturated, unsaturated or aromatic and contains 1 to 4 heteroatoms selected from the group consisting of two oxygen atoms, two sulfur atoms and 4 nitrogen atoms, and is either unsubstituted or itself carries one to three substituents, in each case selected from the group consisting of cyano, nitro, halogen, $C_1$–$C_6$-alkyl, $C_1$–$C_6$-haloalkyl, $C_2$–$C_6$-alkenyl, $C_1$–$C_6$-alkoxy and ($C_1$–$C_6$-alkoxy)carbonyl, or —N($R^{35}$)$R^{36}$, where $R^{35}$ and $R^{36}$ are each hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, $C_1$–$C_6$-alkoxy-$C_1$–$C_6$-alkyl, ($C_1$–$C_6$-alkyl)carbonyl, ($C_1$–$C_6$-alkoxy)carbonyl, ($C_1$–$C_6$-alkoxy)carbonyl-$C_1$–$C_6$-alkyl, ($C_1$–$C_6$-alkoxy)carbonyl-$C_2$–$C_6$-alkenyl, where the alkenyl chain may additionally carry one to three halogen and/or cyano radicals, or phenyl which may be unsubstituted or may itself carry one to three substituents, in each case selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl, or where $R^{35}$ and $R^{36}$ together with the common nitrogen atom form a saturated or unsaturated 4- to 7-membered azaheterocycle which in addition to carbon ring members may, optionally, also contain one of the following members: —O—, —S—, —N═, —NH— or —N($C_1$–$C_6$-alkyl)-;

$R^{24}$ and $R^{25}$ independently of one another are each $C_1$–$C_6$-alkyl, $C_1$–$C_6$-haloalkyl, $C_3$–$C_6$-alkenyl, $C_3$–$C_6$-alkynyl, $C_1$–$C_6$-alkoxy-$C_1$–$C_6$-alkyl or $R^{24}$ and $R^{25}$ together form a saturated or unsaturated 2- to 4-membered hydrocarbon chain which may carry an oxo substituent, where one member of this chain may be replaced by a bridge —O—, —S—, —N═, —NH— or —N($C_1$–$C_6$-alkyl)- which is not adjacent to the variables $Z^1$ and $Z^2$, and where the hydrocarbon chain may carry one to three radicals, in each case selected from the group consisting of cyano, nitro, amino, halogen, $C_1$–$C_6$-alkyl, $C_2$–$C_6$-alkenyl, $C_1$–$C_6$-alkoxy, $C_2$–$C_6$-alkenyloxy, $C_2$–$C_6$-alkynyloxy, $C_1$–$C_6$-haloalkyl, cyano-$C_1$–$C_6$-alkyl, hydroxy-$C_1$–$C_6$-alkyl, $C_1$–$C_6$-alkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_3$–$C_6$-cycloalkyl, $C_3$–$C_6$-cycloalkoxy, carboxyl, ($C_1$–$C_6$-alkoxy)carbonyl, ($C_1$–$C_6$-alkyl)carbonyloxy-$C_1$–$C_6$-alkyl and phenyl which itself may be unsubstituted or may carry one to three substituents, in each case selected from the group consisting of cyano, nitro, amino, halogen, $C_1$–$C_6$-alkyl, $C_1$–$C_6$-haloalkyl, $C_1$–$C_6$-alkoxy and ($C_1$–$C_6$-alkoxy)carbonyl, and where the hydrocarbon chain may also be substituted by a fused-on or spiro-linked 3- to 7-membered ring which may contain as ring members one or two hetero atoms selected from the group consisting of oxygen, sulfur, nitrogen and $C_1$–$C_6$-alkyl-substituted nitrogen, and which may, optionally, itself carry one or two of the following substituents: cyano, $C_1$–$C_6$-alkyl, $C_2$–$C_6$-alkenyl, $C_1$–$C_6$-alkoxy, cyano-$C_1$–$C_6$-alkyl, $C_1$–$C_6$-haloalkyl and ($C_1$–$C_6$-alkoxy)carbonyl;

$R^{26}$ is hydrogen, cyano, halogen, $C_1$–$C_6$-alkyl, $C_1$–$C_6$-haloalkyl, $C_1$–$C_6$-alkoxy, ($C_1$–$C_6$-alkyl)carbonyl or ($C_1$–$C_6$-alkoxy)carbonyl;

$R^{27}$ is hydrogen, O—$R^{34}$, S—$R^{34}$, $C_1$–$C_6$-alkyl which may carry one or two $C_1$–$C_6$-alkoxy substituents, $C_2$–$C_6$-alkenyl, $C_2$–$C_6$-alkynyl, $C_1$–$C_6$-haloalkyl, $C_3$–$C_6$-cycloalkyl, $C_1$–$C_6$-alkylthio-$C_1$–$C_6$-alkyl, $C_1$–$C_6$-alkyliminooxy, —N($R^{32}$)$R^{33}$ or phenyl which may be unsubstituted or may carry one to three substituents, in each case selected from the group consisting of cyano, nitro, halogen, $C_1$–$C_6$-alkyl, $C_2$–$C_6$-alkenyl, $C_1$–$C_6$-haloalkyl, $C_1$–$C_6$-alkoxy and ($C_1$–$C_6$-alkoxy)carbonyl;

$R^{28}$ is hydrogen, cyano, halogen, $C_1$–$C_6$-alkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkyl)carbonyl, ($C_1$–$C_6$-alkoxy)carbonyl, —N($R^{32}$)$R^{33}$, or phenyl which may itself carry one to three substituents, in each case selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl;

$R^{29}$ is hydrogen, cyano, halogen, $C_1$–$C_6$-alkyl, $C_1$–$C_6$-alkoxy, $C_1$–$C_6$-haloalkyl, ($C_1$–$C_6$-alkyl)carbonyl or ($C_1$–$C_6$-alkoxy)carbonyl;

$R^{30}$ is hydrogen, cyano, $C_1$–$C_6$-alkyl or ($C_1$–$C_6$-alkoxy)carbonyl;

$R^{31}$ and $R^{34}$ independently of one another are each hydrogen, $C_1$–$C_6$-alkyl, $C_1$–$C_6$-haloalkyl, $C_2$–$C_6$-alkenyl or $C_2$–$C_6$-alkynyl, where the 4 last-mentioned groups may in each case carry one or two of the following radicals: cyano, halogen, hydroxyl, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy)carbonyl, ($C_1$–$C_6$-alkyl)carbonyloxy, ($C_3$–$C_6$-alkenyloxy) carbonyl or a 3- to 7-membered azaheterocycle which is attached to the nitrogen atom via a carbonyl bridge and which may in addition to carbon ring members also contain an oxygen or sulfur atom as ring member; or ($C_1$–$C_6$-alkyl)carbonyl, ($C_1$–$C_6$-haloalkyl)carbonyl, ($C_1$–$C_6$-alkoxy)carbonyl, $C_1$–$C_6$-alkylaminocarbonyl, di($C_1$–$C_6$-alkyl)aminocarbonyl, $C_1$–$C_6$-alkyloximino-$C_1$–$C_6$-alkyl, $C_3$–$C_6$-cycloalkyl, phenyl or phenyl-$C_1$–$C_6$-alkyl, where the phenyl rings may be unsubstituted or may themselves carry one to three substituents, in each case selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

$R^{32}$ and $R^{33}$ independently of one another are each hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, $C_1$–$C_6$-alkoxy-$C_1$–$C_6$-alkyl, ($C_1$–$C_6$-alkyl)carbonyl, ($C_1$–$C_6$-alkoxy)carbonyl, ($C_1$–$C_6$-alkoxy)carbonyl-$C_1$–$C_6$-alkyl, and the agriculturally useful salts and enol ethers of the compounds I.

2. A substituted 3-phenylisoxazoline of the formula I as claimed in claim 1, where $R^8$ is:

1) hydrogen, hydroxyl, mercapto, cyano, halogen, $C_1$–$C_6$-alkyl, $C_1$–$C_6$-haloalkyl, $C_1$–$C_6$-haloalkoxy, $C_1$–$C_6$-haloalkylthio, $C_1$–$C_6$-alkylthio-($C_1$–$C_6$-alkyl)carbonyl, ($C_1$–$C_6$-alkyl)iminooxycarbonyl, $C_1$–$C_6$-alkoxy-$C_1$–$C_6$-alkyl, $C_1$–$C_6$-alkoxyamino-$C_1$–$C_6$-alkyl, $C_1$–$C_6$-alkoxy-$C_1$–$C_6$-alkylamino-$C_1$–$C_6$-alkyl, 2) $C_1$–$C_6$-alkoxy, $C_1$–$C_6$-alkylthio, $C_3$–$C_6$-cycloalkoxy, $C_3$–$C_6$-cycloalkylthio, $C_2$–$C_6$-alkenyloxy, $C_2$–$C_6$-alkenylthio, $C_2$–$C_6$-alkynyloxy, $C_2$–$C_6$-alkynylthio, ($C_1$–$C_6$-alkyl)carbonyloxy, ($C_1$–$C_6$-alkyl)carbonylthio, ($C_1$–$C_6$-alkoxy)carboxyloxy, ($C_2$–$C_6$-alkenyl)carbonyloxy, ($C_2$–$C_6$-alkenyl)carbonylthio, ($C_2$–$C_6$-alkynyl)carbonyloxy, ($C_2$–$C_6$-alkynyl)carbonylthio, $C_1$–$C_6$-alkylsulfonyloxy or $C_1$–$C_6$-alkylsulfonyl, where each of the 17 last-mentioned radicals may, optionally, carry one to three substituents, in each case selected from the group consisting of halogen, nitro, cyano, hydroxyl, $C_3-C_6$-cycloalkyl, $C_1-C_6$-alkoxy, $C_3-C_6$-cycloalkoxy, $C_3-C_6$-alkenyloxy, $C_3-C_6$-alkynyloxy, $C_1-C_6$-alkoxy-$C_1-C_6$-alkoxy, $C_1-C_6$-alkylthio, $C_1-C_6$-alkylsulfinyl, $C_1-C_6$-alkylsulfonyl, $C_1-C_6$-alkylideneaminooxy, oxo, =N—OR$^{18}$, the phenyl, phenoxy or phenylsulfonyl group, which may be unsubstituted or may carry one to three substituents, in each case selected from the group consisting of halogen, nitro, cyano, $C_1-C_6$-alkyl, $C_1-C_6$-haloalkyl, $C_1-C_6$-alkoxy and ($C_1-C_6$-alkoxy)carbonyl, a group —CO—R$^{19}$, —CO—OR$^{19}$, —CO—SR$^{19}$, —CO—N(R$^{19}$)R$^{20}$, —OCO—R$^{19}$, —OCO—OR$^{19}$, —OCO—SR$^{19}$, —OCO—N(R$^{19}$)R$^{20}$ or —N(R$^{19}$)—R$^{20}$, the group —C(R$^{21}$)=N—OR$^{18}$;

3) —CO—R$^{22}$, —CS—R$^{22}$, —C(NR$^{23}$)—R$^{22}$, —C(R$^{22}$)(Z$^1$R$^{24}$)(Z$^2$R$^{25}$), where Z$^1$ and Z$^2$ are each oxygen or sulfur, —C(R$^{22}$)=C(R$^{26}$)—CN, —C(R$^{22}$)=C(R$^{26}$)—CO—R$^{27}$, —CH(R$^{22}$)—CH(R$^{26}$)—CO—R$^{27}$, —C(R$^{22}$)=C(R$^{26}$)—CH$_2$—CO—R$^{27}$, —C(R$^{22}$)=C(R$^{26}$)—C(R$^{29}$)—CO—R$^{27}$, —C(R$^{22}$)=C(R$^{26}$)—CH$_2$—CH(R$^{30}$)—CO—R$^{27}$, —CO—OR$^{31}$, —CO—SR$^{31}$, —CO—N(R$^{31}$)—OR$^{18}$, —C≡C—CO—NH—OR$^{18}$, —C≡C—CO—N(R$^{31}$)—OR$^{18}$, —C≡C—CS—NH—OR$^{18}$, —C≡C—CS—N(R$^{31}$)—OR$^{18}$, —C(R$^{22}$)=C(R$^{26}$)—CO—NH—OR$^{18}$, —C(R$^{22}$)=C(R$^{26}$)—CO—N(R$^{31}$)—OR$^{18}$, —C(R$^{22}$)=C(R$^{26}$)—CS—NH—OR$^{18}$, —C(R$^{22}$)=C(R$^{26}$)—CS—N(R$^{31}$)—OR$^{18}$, —C(R$^{22}$)=C(R$^{26}$)—C(R$^{21}$)=N—OR$^{18}$, —C(R$^{21}$)=N—OR$^{18}$, —C≡C—C(R$^{21}$)=N—OR$^{18}$, —C(Z$^1$R$^{24}$)(Z$^2$R$^{25}$)—OR$^{31}$, —C(Z$^1$R$^{24}$)(Z$^2$R$^{25}$)—SR$^{31}$, —C(Z$^1$R$^{24}$)(Z$^2$R$^{25}$)—N(R$^{32}$)R$^{33}$, —N(R$^{32}$)R$^{33}$ or —CON(R$^{32}$)R$^{33}$;

$R^{18}$ is hydrogen, $C_1-C_6$-alkyl, $C_1-C_6$-haloalkyl, $C_3-C_6$-cycloalkyl, $C_3-C_6$-alkenyl, $C_3-C_6$-alkynyl, hydroxy-$C_1-C_6$-alkyl, $C_1-C_6$-alkoxy-$C_1-C_6$-alkyl, $C_1-C_6$-alkylthio-$C_1-C_6$-alkyl, cyano-$C_1-C_6$-alkyl, ($C_1-C_6$-alkyl)carbonyl-$C_1-C_6$-alkyl, ($C_1-C_6$-alkoxy)carbonyl-$C_1-C_6$-alkyl, ($C_1-C_6$-alkoxy)carbonyl-$C_2-C_6$-alkenyl, ($C_1-C_6$-alkyl)carbonyloxy-$C_1-C_6$-alkyl or phenyl-$C_1-C_6$-alkyl, where the phenyl ring may, optionally, carry one to three substituents, in each case selected from the group consisting of cyano, nitro, halogen, $C_1-C_6$-alkyl, $C_1-C_6$-haloalkyl, $C_1-C_6$-alkoxy and ($C_1-C_6$-alkoxy)carbonyl;

$R^{19}$ is hydrogen, $C_1-C_6$-alkyl, $C_3-C_6$-cycloalkyl, $C_3-C_6$-alkenyl, $C_3-C_6$-alkynyl, $C_1-C_6$-alkoxy-$C_1-C_6$-alkyl, ($C_1-C_6$-alkoxy)carbonyl-$C_1-C_6$-alkyl, ($C_3-C_6$-alkenyloxy)carbonyl-$C_1-C_6$-alkyl, phenyl or phenyl-$C_1-C_6$-alkyl, where the phenyl group and the phenyl ring of the phenylalkyl group may be unsubstituted or may carry one to three radicals, in each case selected from the group consisting of halogen, nitro, cyano, $C_1-C_6$-alkyl, $C_1-C_6$-haloalkyl, $C_1-C_6$-alkoxy and ($C_1-C_6$-alkyl)carbonyl;

$R^{20}$ is hydrogen, hydroxyl, $C_1-C_6$-alkyl, $C_3-C_6$-cycloalkyl, $C_1-C_6$-alkoxy, ($C_1-C_6$-alkoxy)carbonyl-$C_1-C_6$-alkoxy, $C_3-C_6$-alkenyl or $C_3-C_6$-alkenyloxy;

$R^{21}$ is
hydrogen, halogen,
$C_1-C_6$-alkyl, $C_1-C_6$-haloalkyl, $C_1-C_6$-alkoxy, $C_1-C_6$-haloalkoxy, $C_3-C_6$-alkenyloxy, $C_1-C_6$-alkylthio, $C_1-C_6$-haloalkylthio, ($C_1-C_6$-alkyl)carbonyloxy, ($C_1-C_6$-haloalkyl)carbonyloxy, $C_1-C_6$-alkylsulfonyloxy or $C_1-C_6$-haloalkylsulfonyloxy, where the 11 last-mentioned radicals may carry one of the following substituents: hydroxyl, cyano, hydroxycarbonyl, $C_1-C_6$-alkoxy, $C_1-C_6$-alkylthio, ($C_1-C_6$-alkyl)carbonyl, ($C_1-C_6$-alkoxy)carbonyl, ($C_1-C_6$-alkyl)aminocarbonyl, di($C_1-C_6$-alkyl)aminocarbonyl, ($C_1-C_6$-alkyl)carbonyloxy, $C_1-C_6$-alkoxy-($C_1-C_6$-alkyl)aminocarbonyl;

a 3- to 7-membered azaheterocycle which is attached to the nitrogen atom via a carbonyl bridge and which may, in addition to carbon ring members, also contain one oxygen or sulfur atom as ring member;

($C_1-C_6$-alkyl)carbonyl, ($C_1-C_6$-haloalkyl)carbonyl, ($C_1-C_6$-alkoxy)carbonyl, ($C_1-C_6$-alkoxy)carbonyloxy, ($C_1-C_6$-alkyl)carbonylthio, ($C_1-C_6$-haloalkyl)carbonylthio, ($C_1-C_6$-alkoxy)carbonylthio, $C_2-C_6$-alkenyl, $C_2-C_6$-alkenylthio, $C_3-C_6$-alkynyl, $C_3-C_6$-alkynyloxy, $C_3-C_6$-alkynylthio, ($C_2-C_6$-alkynyl)carbonyloxy, $C_3-C_6$-alkynylsulfonyloxy, $C_3-C_6$-cycloalkyl, $C_3-C_6$-cycloalkyloxy, $C_3-C_6$-cycloalkylthio, ($C_3-C_6$-cycloalkyl)carbonyloxy, $C_3-C_6$-cycloalkylsulfonyloxy;

phenyl, phenoxy, phenylthio, benzoyloxy, phenylsulfonyloxy, phenyl-$C_1-C_6$-alkyl, phenyl-$C_1-C_6$-alkoxy, phenyl-$C_1-C_6$-alkylthio, phenyl-($C_1-C_6$-alkyl)carbonyloxy or phenyl-($C_1-C_6$-alkyl)sulfonyloxy, where the phenyl rings of the 10 last-mentioned radicals may be unsubstituted or may themselves carry one to three substituents, in each case selected from the group consisting of cyano, nitro, halogen, $C_1-C_6$-alkyl, $C_1-C_6$-haloalkyl, $C_1-C_6$-alkoxy and ($C_1-C_6$-alkoxy)carbonyl;

$R^{22}$ is hydrogen, cyano, $C_1-C_6$-alkyl, $C_1-C_6$-haloalkyl, $C_2-C_6$-alkenyl, $C_2-C_6$-alkynyl, $C_3-C_6$-cycloalkyl, $C_1-C_6$-alkoxy-$C_1-C_6$-alkyl or ($C_1-C_6$-alkoxy)carbonyl;

$R^{23}$ is hydrogen, hydroxyl, $C_1-C_6$-alkyl, $C_3-C_6$-alkenyl, $C_3-C_6$-alkynyl, $C_3-C_7$-cycloalkyl, $C_1-C_6$-haloalkyl, $C_1-C_6$-alkoxy-$C_1-C_6$-alkyl, $C_1-C_6$-alkoxy, $C_3-C_6$-alkenyloxy, $C_3-C_6$-alkynyloxy, $C_3-C_6$-cycloalkyloxy, $C_5-C_7$-cycloalkenyloxy, $C_1-C_6$-haloalkoxy, $C_3-C_6$-haloalkenyloxy, hydroxy-$C_1-C_6$-alkoxy, cyano-$C_1-C_6$-alkoxy, $C_3-C_6$-cycloalkyl-$C_1-C_6$-alkoxy, $C_1-C_6$-alkoxy-$C_1-C_6$-alkoxy, $C_1-C_6$-alkoxy-$C_3-C_6$-alkenyloxy, ($C_1-C_6$-alkyl)carbonyloxy, ($C_1-C_6$-haloalkyl)carbonyloxy, ($C_1-C_6$-alkyl)carbamoyloxy, ($C_1-C_6$-haloalkyl)carbamoyloxy, ($C_1-C_6$-alkyl)carbonyl-$C_1-C_6$-alkyl, ($C_1-C_6$-alkyl)carbonyl-$C_1-C_6$-alkoxy, ($C_1-C_6$-alkoxy)carbonyl-$C_1-C_6$-alkyl, ($C_1-C_6$-alkoxy)carbonyl-$C_1-C_6$-alkoxy, $C_1-C_6$-alkylthio-$C_1-C_6$-alkoxy, di($C_1-C_6$-alkyl)amino-$C_1-C_6$-alkoxy, phenyl which may itself carry one to three substituents, in each case selected from the group consisting of cyano, nitro, halogen, $C_1-C_6$-alkyl, $C_1-C_6$-haloalkyl, $C_2-C_6$-alkenyl, $C_1-C_6$-alkoxy and ($C_1-C_6$-alkoxy)carbonyl, phenyl-$C_1-C_6$-alkoxy, phenyl-$C_3-C_6$-alkenyloxy or phenyl-$C_3-C_6$-alkynyloxy, where in each case one or two methylene groups of the hydrocarbon chains may be replaced by —O—, —S— or —N($C_1-C_6$-alkyl)-, and where each phenyl ring may be unsubstituted or may itself carry one to three substituents, in each case selected from the group consisting of cyano, nitro, halogen, $C_1-C_6$-alkyl, $C_1-C_6$-haloalkyl, $C_2-C_6$-alkenyl, $C_1-C_6$-alkoxy and ($C_1-C_6$-alkoxy)carbonyl, heterocyclyl, heterocyclyl-$C_1-C_6$-alkoxy, heterocyclyl-$C_3-C_6$-alkenyloxy or heterocyclyl-$C_3$–$C_6$-alkynyloxy, where in each case one or two methylene groups of the hydrocarbon chains may be replaced by —O—, —S— or —N($C_1$–$C_6$-alkyl)-, and where each heterocycle may be 3- to 7-membered, saturated, unsaturated or aromatic and contains one to four hetero atoms selected from the group consisting of two oxygen atoms, two sulfur atoms and 4 nitrogen atoms, and is either unsubstituted or itself carries one to three substituents, in each case selected from the group consisting of cyano, nitro, halogen, $C_1$–$C_6$-alkyl, $C_1$–$C_6$-haloalkyl, $C_2$–$C_6$-alkenyl, $C_1$–$C_6$-alkoxy and ($C_1$–$C_6$-alkoxy)carbonyl, or —N($R^{35}$)$R^{36}$ where $R^{35}$ and $R^{36}$ are each hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, $C_1$–$C_6$-alkoxy-$C_1$–$C_6$-alkyl, ($C_1$–$C_6$-alkyl)carbonyl, ($C_1$–$C_6$-alkoxy)carbonyl, ($C_1$–$C_6$-alkoxy)carbonyl-$C_1$–$C_6$-alkyl, ($C_1$–$C_6$-alkoxy)carbonyl-$C_2$–$C_6$-alkenyl where the alkenyl chain may additionally carry one to three halogen and/or cyano radicals, or are phenyl which may be unsubstituted or may itself carry one to three substituents, in each case selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl, or where $R^{35}$ and $R^{36}$ together with the linking nitrogen atom form a saturated or unsaturated 4- to 7-membered azaheterocycle which, in addition to carbon ring members, may, optionally, also contain one of the following members: —O—, —S—, —N=, —NH— or —N($C_1$–$C_6$-alkyl)-;

$R^{24}$ and $R^{25}$ independently of one another are each $C_1$–$C_6$-alkyl, $C_1$–$C_6$-haloalkyl, $C_3$–$C_6$-alkenyl, $C_3$–$C_6$-alkynyl, $C_1$–$C_6$-alkoxy-$C_1$–$C_6$-alkyl or together are a saturated or unsaturated 2- to 4-membered hydrocarbon chain which may carry an oxo substituent, where one member of this chain may be replaced by a bridge —O—, —S—, —N=, —NH— or —N($C_1$–$C_6$-alkyl)- which is not adjacent to the variables $Z^1$ and $Z^2$, and where the hydrocarbon chain may carry one to three radicals, in each case selected from the group consisting of cyano, nitro, amino, halogen, $C_1$–$C_6$-alkyl, $C_2$–$C_6$-alkenyl, $C_1$–$C_6$-alkoxy, $C_2$–$C_6$-alkenyloxy, $C_2$–$C_6$-alkynyloxy, $C_1$–$C_6$-haloalkyl, cyano-$C_1$–$C_6$-alkyl, hydroxy-$C_1$–$C_6$-alkyl, $C_1$–$C_6$-alkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_3$–$C_6$-cycloalkyl, $C_3$–$C_6$-cycloalkoxy, carboxyl, ($C_1$–$C_6$-alkoxy)carbonyl, ($C_1$–$C_6$-alkyl)carbonyloxy-$C_1$–$C_6$-alkyl and phenyl which may itself be unsubstituted or may carry one to three substituents, in each case selected from the group consisting of cyano, nitro, amino, halogen, $C_1$–$C_6$-alkyl, $C_1$–$C_6$-haloalkyl, $C_1$–$C_6$-alkoxy and ($C_1$–$C_6$-alkoxy)carbonyl, and where the hydrocarbon chain may also be substituted by a fused-on or spiro-linked 3- to 7-membered ring which may contain as ring members one or two hetero atoms selected from the group consisting of oxygen, sulfur, nitrogen and $C_1$–$C_6$-alkyl-substituted nitrogen, and which may, optionally, itself carry one or two of the following substituents: cyano, $C_1$–$C_6$-alkyl, $C_2$–$C_6$-alkenyl, $C_1$–$C_6$-alkoxy, cyano-$C_1$–$C_6$-alkyl, $C_1$–$C_6$-haloalkyl and ($C_1$–$C_6$-alkoxy)carbonyl;

$R^{26}$ is hydrogen, cyano, halogen, $C_1$–$C_6$-alkyl, $C_1$–$C_6$-haloalkyl, $C_1$–$C_6$-alkoxy, ($C_1$–$C_6$-alkyl)carbonyl or ($C_1$–$C_6$-alkoxy)carbonyl;

$R^{27}$ is hydrogen, O—$R^{34}$, S—$R^{34}$, $C_1$–$C_6$-alkyl which may carry one or two $C_1$–$C_6$-alkoxy substituents, $C_2$–$C_6$-alkenyl, $C_2$–$C_6$-alkynyl, $C_1$–$C_6$-haloalkyl, $C_3$–$C_6$-cycloalkyl, $C_1$–$C_6$-alkylthio-$C_1$–$C_6$-alkyl, $C_1$–$C_6$-alkyliminooxy, —N($R^{32}$)$R^{33}$ or phenyl which may be unsubstituted or may carry one to three substituents, in each case selected from the group consisting of cyano, nitro, halogen, $C_1$–$C_6$-alkyl, $C_2$–$C_6$-alkenyl, $C_1$–$C_6$-haloalkyl, $C_1$–$C_6$-alkoxy and ($C_1$–$C_6$-alkoxy)carbonyl;

$R^{28}$ is hydrogen, cyano, halogen, $C_1$–$C_6$-alkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkyl)carbonyl, ($C_1$–$C_6$-alkoxy)carbonyl, —N($R^{32}$)$R^{33}$ or phenyl which may itself carry one to three substituents, in each case selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl;

$R^{29}$ is hydrogen, cyano, halogen, $C_1$–$C_6$-alkyl, $C_1$–$C_6$-alkoxy, $C_1$–$C_6$-haloalkyl, ($C_1$–$C_6$-alkyl)carbonyl or ($C_1$–$C_6$-alkoxy)carbonyl;

$R^{30}$ is hydrogen, cyano, $C_1$–$C_6$-alkyl or ($C_1$–$C_6$-alkoxy)carbonyl;

$R^{31}$ and $R^{34}$ independently of one another are each hydrogen, $C_1$–$C_6$-alkyl, $C_1$–$C_6$-haloalkyl, $C_2$–$C_6$-alkenyl or $C_2$–$C_6$-alkynyl, where the 4 last-mentioned groups may in each case carry one or two of the following radicals: cyano, halogen, hydroxyl, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy)carbonyl, ($C_1$–$C_6$-alkyl)carbonyloxy, ($C_3$–$C_6$-alkenyloxy) carbonyl or a 3- to 7-membered azaheterocycle which is attached to the nitrogen atom via a carbonyl bridge and which may, in addition to carbon ring members, also contain one oxygen or sulfur atom as ring member; or are ($C_1$–$C_6$-alkyl)carbonyl, ($C_1$–$C_6$-haloalkyl) carbonyl, ($C_1$–$C_6$-alkoxy)carbonyl, $C_1$–$C_6$-alkylaminocarbonyl, di($C_1$–$C_6$-alkyl)aminocarbonyl, $C_1$–$C_6$-alkyloximino-$C_1$–$C_6$-alkyl, $C_3$–$C_6$-cycloalkyl, phenyl or phenyl-$C_1$–$C_6$-alkyl, where the phenyl rings may be unsubstituted or may themselves carry one to three substituents, in each case selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy) carbonyl;

$R^{32}$ and $R^{33}$ independently of one another are each hydrogen, $C_1$–$C_6$-alkyl, $C_3$–$C_6$-alkenyl, $C_2$–$C_6$-alkynyl, $C_3$–$C_6$-cycloalkyl, $C_1$–$C_6$-haloalkyl, $C_1$–$C_6$-alkoxy-$C_1$–$C_6$-alkyl, ($C_1$–$C_6$-alkyl)carbonyl, ($C_1$–$C_6$-alkoxy)carbonyl, ($C_1$–$C_6$-alkoxy)carbonyl-$C_1$–$C_6$-alkyl, ($C_1$–$C_6$-alkoxy)carbonyl-$C_2$–$C_6$-alkenyl, where the alkenyl chain may additionally carry one to three halogen and/or cyano radicals, or are $C_1$–$C_6$-alkylsulfonyl, ($C_1$–$C_6$-alkoxy)carbonyl-$C_1$–$C_6$-alkylsulfonyl, phenyl or phenylsulfonyl, where the two phenyl rings may be unsubstituted or may themselves carry one to three substituents, in each case selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl, or $R^{32}$ and $R^{33}$ together with the linking nitrogen atom are a saturated or unsaturated 4- to 7-membered azaheterocycle which, in addition to carbon ring members, may, optionally, contain one of the following members: —O—, —S—, —N=, —NH— or —N($C_1$–$C_6$-alkyl)-.

3. A herbicidal composition, comprising a herbicidally effective amount of at least one substituted 3-phenylisoxazoline of the formula I or an agriculturally useful salt or enol ether of I, as claimed in claim 1, and at least one inert liquid and/or solid carrier and, optionally, at least one surfactant.

4. A process for the preparation of herbicidally active compositions, which comprises mixing a herbicidally effective amount of at least one substituted 3-phenylisoxazoline of the formula I or an agriculturally useful salt or enol ether of I, as claimed in claim 1, and at least one inert liquid and/or solid carrier and, optionally, at least one surfactant.

5. A method for controlling unwanted vegetation, which comprises allowing a herbicidally effective amount of at least one substituted 3-phenylisoxazoline of the formula I or an agriculturally useful salt or enol ether of I, as claimed in claim 1, to act on plants, their habitat or on seeds.

* * * * *

UNITED STATES PATENT AND TRADEMARK OFFICE
CERTIFICATE OF CORRECTION

PATENT NO. : 6,150,303
DATED : November 21, 2000
INVENTOR(S) : Menke et al.

It is certified that error appears in the above-identified patent and that said Letters Patent is hereby corrected as shown below:

Column 50, claim 1,
Line 17, after "alkyl," insert the following missing information:

-- ($C_1$-$C_6$-alkoxy)carbonyl-$C_2$-$C_6$-alkenyl, where the alkenyl, chain may additionally carry one to three halogen and/or cyano radicals, or $C_1$-$C_6$-alkylsulfonyl, ($C_1$-$C_6$-alkoxy)carbonyl-$C_1$-$C_6$-alkylsulfonyl, phenyl or phenylsulfonyl, where the two phenyl rings may be unsubstituted or may themselves carry one to three substituents, in each case selected from the group consisting of cyano, nitro, halogen, $C_1$-$C_6$-alkyl, $C_1$-$C_6$-haloalkyl, $C_3$-$C_6$-alkenyl, $C_1$-$C_6$-alkoxy and ($C_1$-$C_6$-alkoxy)carbonyl, or $R^{32}$ and $R^{33}$ together with the linking nitrogen atom form a saturated or unsaturated 4- to 7-membered azaheterocycle which, in addition to carbon ring members, may, if desired, contain one of the following members: -O-, -S-, -N=, -NH- or -N($C_1$-$C_6$-alkyl)-; --

Signed and Sealed this

Thirteenth Day of November, 2001

Attest:

NICHOLAS P. GODICI
Attesting Officer    Acting Director of the United States Patent and Trademark Office